(12) United States Patent
Allen et al.

(10) Patent No.: US 7,952,537 B2
(45) Date of Patent: May 31, 2011

(54) MEDICAL OVERLAY MIRROR

(75) Inventors: Paul G. Allen, Seattle, WA (US);
Edward K. Y. Jung, Bellevue, WA (US);
Royce A. Levien, Lexington, MA (US);
Mark A. Malamud, Seattle, WA (US);
John D. Rinaldo, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

(21) Appl. No.: 12/660,030

(22) Filed: Feb. 17, 2010

(65) Prior Publication Data

US 2010/0214240 A1    Aug. 26, 2010

Related U.S. Application Data

(60) Division of application No. 11/639,366, filed on Dec. 13, 2006, now Pat. No. 7,679,581, and a continuation-in-part of application No. 10/910,421, filed on Aug. 2, 2004, now Pat. No. 7,283,106, and a continuation-in-part of application No. 10/912,271, filed on Aug. 5, 2004, now Pat. No. 7,133,003, and a continuation-in-part of application No. 10/941,803, filed on Sep. 15, 2004, now Pat. No. 7,714,804, and a continuation-in-part of application No. 10/951,002, filed on Sep. 27, 2004, now Pat. No. 7,259,731, and a continuation-in-part of application No. 10/972,319, filed on Oct. 22, 2004, now Pat. No. 7,657,125, and a continuation-in-part of application No. 11/478,334, filed on Jun. 28, 2006, now Pat. No. 7,259,732, and a continuation-in-part of application No. 11/540,928, filed on Sep. 28, 2006, now Pat. No. 7,429,966, and a continuation-in-part of application No. 11/638,305, filed on Dec. 12, 2006, now Pat. No. 7,679,580, and a continuation-in-part of application No. 11/982,731, filed on Nov. 1, 2007, now Pat. No. 7,692,606, and a continuation-in-part of application No. 11/726,114, filed on Mar. 20, 2007, and a continuation-in-part of application No. 11/981,805, filed on Oct. 30, 2007, now Pat. No. 7,663,571, and a continuation-in-part of application No. 11/982,326, filed on Oct. 31, 2007, now Pat. No. 7,683,858, and a continuation-in-part of application No. 11/982,396, filed on Oct. 31, 2007, now Pat. No. 7,705,800, and a continuation-in-part of application No. 12/154,694, filed on May 22, 2008, now Pat. No. 7,636,072, and a continuation-in-part of application No. 12/220,671, filed on Jul. 25, 2008, and a continuation-in-part of application No. 12/286,556, filed on Sep. 29, 2008, now Pat. No. 7,671,823, and a continuation-in-part of application No. 12/286,457, filed on Sep. 30, 2008, and a continuation-in-part of application No. 12/658,260, filed on Feb. 3, 2010.

(51) Int. Cl.
*G09G 3/00* (2006.01)
(52) U.S. Cl. .......................... 345/32; 345/156
(58) Field of Classification Search ................ 345/8, 32, 345/156; 132/301; 434/371; D28/64.1
See application file for complete search history.

(56) References Cited

U.S. PATENT DOCUMENTS 3,838,525 A    10/1974    Harvey
(Continued)

FOREIGN PATENT DOCUMENTS

BW    06055957 A2    3/1994
(Continued)

OTHER PUBLICATIONS

Azuma, Ronald; Baillot, Yohan; Behringer, Reinhold; Feiner, Steven; Julier, Simon; MacIntyre, Blair; "Recent Advances in Augmented Reality," pp. 34-47; located at www.cs.unc.edu/~azuma/cga2001.pdf; bearing a date of Nov./Dec. 2001; printed on Jul. 12, 2004.

(Continued)

*Primary Examiner* — Ricardo L Osorio

(57)    ABSTRACT

Medical overlay mirror methods and related systems.

29 Claims, 47 Drawing Sheets

U.S. PATENT DOCUMENTS

| | | | |
|---|---|---|---|
| 3,934,226 | A | 1/1976 | Stone et al. |
| 4,309,094 | A | 1/1982 | Bollen |
| 5,198,936 | A | 3/1993 | Stringfellow |
| 5,997,149 | A | 12/1999 | Chu |
| 6,032,119 | A | 2/2000 | Brown et al. |
| 6,071,236 | A | 6/2000 | Iliff |
| 6,077,225 | A | 6/2000 | Brock-Fisher |
| 6,081,611 | A | 6/2000 | Linford et al. |
| 6,095,985 | A | 8/2000 | Raymond et al. |
| 6,120,467 | A | 9/2000 | Schallhorn |
| 6,238,337 | B1 | 5/2001 | Kambhatla et al. |
| 6,272,468 | B1 | 8/2001 | Melrose |
| 6,322,502 | B1 | 11/2001 | Schoenberg et al. |
| 6,336,900 | B1 | 1/2002 | Alleckson et al. |
| 6,402,689 | B1 | 6/2002 | Scarantino et al. |
| 6,440,090 | B1 | 8/2002 | Schallhorn |
| 6,454,708 | B1 | 9/2002 | Ferguson et al. |
| 6,468,263 | B1 | 10/2002 | Fischell et al. |
| 6,477,394 | B2 | 11/2002 | Rice et al. |
| 6,516,210 | B1 | 2/2003 | Foxall |
| 6,542,204 | B1 | 4/2003 | Ohzawa et al. |
| 6,556,977 | B1 | 4/2003 | Lapointe et al. |
| 6,569,094 | B2 | 5/2003 | Suzuki et al. |
| 6,574,742 | B1 | 6/2003 | Jamroga et al. |
| 6,678,703 | B2 | 1/2004 | Rothschild et al. |
| 6,710,927 | B2 | 3/2004 | Richards |
| 6,725,200 | B1 | 4/2004 | Rost |
| 6,746,122 | B2 | 6/2004 | Knox |
| 6,755,539 | B2 | 6/2004 | Brennesholtz |
| 6,757,087 | B1 | 6/2004 | Taketomi et al. |
| 6,760,515 | B1 | 7/2004 | Wang et al. |
| 6,761,458 | B2 | 7/2004 | Sakata et al. |
| 6,762,870 | B2 | 7/2004 | De Vaan |
| 6,768,915 | B2 | 7/2004 | Brand et al. |
| 6,774,869 | B2 | 8/2004 | Biocca et al. |
| 6,869,772 | B2 | 3/2005 | Lichtman et al. |
| 7,080,910 | B2 | 7/2006 | Engle |
| 2001/0031081 | A1 | 10/2001 | Quan et al. |
| 2001/0037191 | A1 | 11/2001 | Furuta et al. |
| 2002/0064302 | A1 | 5/2002 | Massengill |
| 2002/0196333 | A1 | 12/2002 | Gorischek |
| 2003/0041871 | A1 | 3/2003 | Endo et al. |
| 2004/0095359 | A1 | 5/2004 | Simon et al. |
| 2005/0027567 | A1 | 2/2005 | Taha |
| 2005/0035313 | A1 | 2/2005 | Garssen et al. |
| 2005/0174473 | A1 | 8/2005 | Morgan et al. |
| 2005/0185278 | A1 | 8/2005 | Horsten et al. |
| 2006/0017605 | A1 | 1/2006 | Lovberg et al. |
| 2007/0258656 | A1 | 11/2007 | Aarabi |

FOREIGN PATENT DOCUMENTS

| | | |
|---|---|---|
| BX | 05181216 A2 | 7/1993 |
| WO | WO 02/080773 A1 | 10/2002 |

OTHER PUBLICATIONS

Butz, Andreas; Beshers, Clifford; Feiner, Steven; "Of Vampire Mirrors and Privacy Lamps: Privacy Management in Multi-User Augmented Environments," pp. 171-172; located at http://www1.cs.columbia.edu/~butz/publications/papers/uist98.pdf; bearing a date of Nov. 2-4, 1998; printed on Jul. 12, 2004.

Computer Vision & Robotics Laboratory Beckman Institute, "Multiview Mirror Pyramid Panoramic Cameras," Tan, Kar-Han; Hua, Hong; Ahuja, Narendar from the Beckman Institute for Advanced Science and Technology, University of Illinois at Urbana-Champaign, pp. 1-4 located at http://vision.ai.uiuc.edu/~tankh/Camera/camera.html printed on Aug. 9, 2004.

Francois, Alexandre R.J.; Kang, Elaine; "The Virtual Mirror," pp. 1-5; located at http://iris.usc.edu/~ afrancoi/virtual_mirror/; printed on Jul. 12, 2004.

Fulford, Benjamin, "Adventures in the Third Dimension" pp. 1-3 located at www.forbes.com/forbes/2004/0524/166_print.html bearing a date of May 24, 2004 and printed on Sep. 1, 2004.

Healthy Style Products, "Emjoi—The Mirror AP-13," pp. 1-2 located at http://www.healthystyleproducts.com/mirror.html printed on Sep. 1, 2004.

Highbeam Research; "Winntech. (Globalshop 2003 Spotlight);" pp. 1; located at http://www.highbeam.com/library/doc0. asp?docid=1G1:99048681&refid=ink_g5s1&skeyw; printed on Jul. 12, 2004.

Lin, I-Chen; Yeh, Jeng-Sheng; and Ouhyoung, Ming from National Taiwan University, "Extracting 3D Facial Animation Parameters from Multiview Video Clips," pp. 2-10, bearing a date of Nov./Dec. 2002 and printed on Sep. 1, 2004.

Lin, I-Chen, "The Software Tool of Mass 3D Facial Animation Parameter Extraction from Mirror-Reflected Multi-View Video User's Instruction Version 1.0," located at http://www.cmlab.csie.ntu.edu.tw/~ichen, pp. 1-24 (+ cover sheet), printed on Sep. 1, 2004.

Morimoto, Carlos Hitoshi; "Interactive Digital Mirror," from XIV Brazilian Symposium on Computer Graphics and Image Processing (SIBGRAPI'01), Oct. 15-18, 2001; pp. 1; located at http://csdl.computer.org/comp/proceeding/sibgrapi/2001/1330/00/13300232abs.htm; bearing a date of 2001; printed on Jul. 12, 2004.

Nextag, "Accessories—compare prices, review and buy at NexTag—Price—Review re Jerdon Mirror,"pp. 1-2 located at http://www.nextag.com/Jerdon_Accessories~2702144zJerdonz0zB36ozmainz5-htm printed on Aug. 9, 2004.

NP Review.Info, "New Product Reviews: New Product Review—Jerdon JGL9W5X Magnification Tri-fold Lighted Mirror Product Review," pp. 1-3 located at http://www.npreview.info/Home-and-Garden/Home-Decor/Mirrors/Vanity-Mirrors/Jerdon-JGL9W-5X-Magnification-Tri-fold-Lighted-Mirror.html printed on Sep. 1, 2004.

PCT International Search Report; International App. No. PCT/US05/27411; Jul. 7, 2008; pp. 1-2.

PCT International Search Report; International App. No. PCT/US05/27250; May 2, 2006.

PCT International Search Report; International App. No. PCT/US05/27249; Apr. 21, 2006.

PCT International Search Report; International App. No. PCT/US05/27256; Apr. 21, 2006.

PCT International Search Report; International App. No. PCT/US05/27410; Jan. 27, 2006.

Radford, Tim, "Mirror, Mirror on the Wall, Who'll Be Fattest of Them All?", The Guardian Unlimited, bearing a date of Feb. 3, 2005, pp. 1-4, located at http://www.guardian.co.uk/uk_ news/story/0,3604,1404636,00.html, printed on Feb. 4, 2005.

Riviere, Cameron; Taylor, Russ; Digioia, A.; Wenz, J.; Kostuik, J.; Frassica, F.; "Engineered System Family #3: Information-enhanced Minimally Invasive Surgery," pp. 1-12; located at http://cisstweb.cs.jhu.edu/research/InfoEnhMIS/InfoEnhMISMain.htm; printed on Jul. 12, 2004.

Rochester Institute of Technoloy; "Introduction to Augmented Reality," pp. 1-12; located at http://www.se.rit.edu/~jrv/research/ar/introduction.html; printed on Jul. 12, 2004.

Siggraph Emerging Technologies 1991-2002; "Interactive Paradigm, Technique," pp. 1-5; located at http://www.siggraph.org/~fujii/etech/s_interactive.html; bearing a date of Jul. 5, 2002; printed on Jul. 12, 2004.

Siggraph Emerging Technologies 1991-2002; "Magic Morphin Mirror: Face-Sensitive Distortion and Exaggeration," pp. 1-2; located at http://siggraph.org./~jujii/etech/1997_190.html; bearing a date of Jul. 5, 2002; printed on Jul. 12, 2004.

Spohrer, J.C.; "Information in places," from vol. 38, allegedly of No. 4, 1999, Pervasive Computing; pp. 1-25; located at http://www.research.ibm.com/journal/sj/384/spohrer.html; printed on Jul. 12, 2004.

Sturm, Peter, "Mixing Catadioptric and Perspective Cameras," pp. 1-8, located at http://www.inrialpes.fr/movi/people/Sturm bearing a date of 2002 and printed on Sep. 1, 2004.

Tan, Kar-Han; Hua, Hong, Ahuja, Narenda "Multiview Panoramic Cameras Using Mirror Pyramids," accepted for publication in the IEEE Transactions on Pattern Analysis and Machine Intelligence journal, pp. 1-19 (+ cover sheet), printed on Sep. 1, 2004.

Taniguchi, Rin-Ichiro, "Real-Time Multiview Image Analysis and Its Application," pp. 1-8 printed on Sep. 1, 2004.

The Swiss Technorama Science Center, "Mirrors in Mind: Mirror, Mirror, on the Wall," pp. 1-12, located at http://www.technorama.ch/rentals/description.html printed on Sep. 1, 2004.

TRAXTAL; "What is Augmented Reality," pp. 1-2; located at http://www.traxtal.com/rd/rd_classroom_augmentedreality.htm; printed on Jul. 12, 2004.

U.S. Appl. No. 12/658,260, Paul G. Allen et al.

Non-final Office Action for 11/726,114; bearing a date of May 12, 2010; 18 pages.

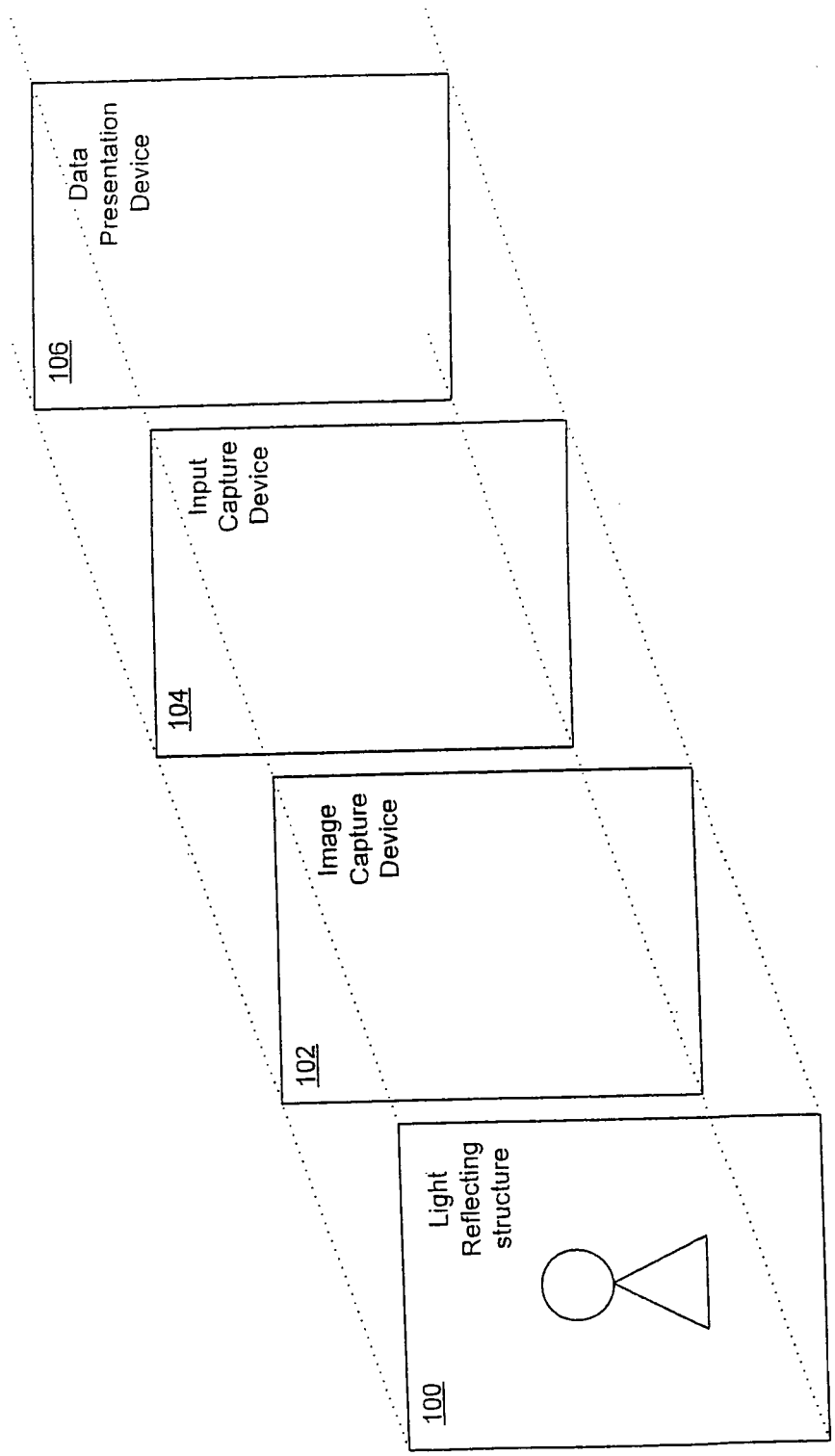

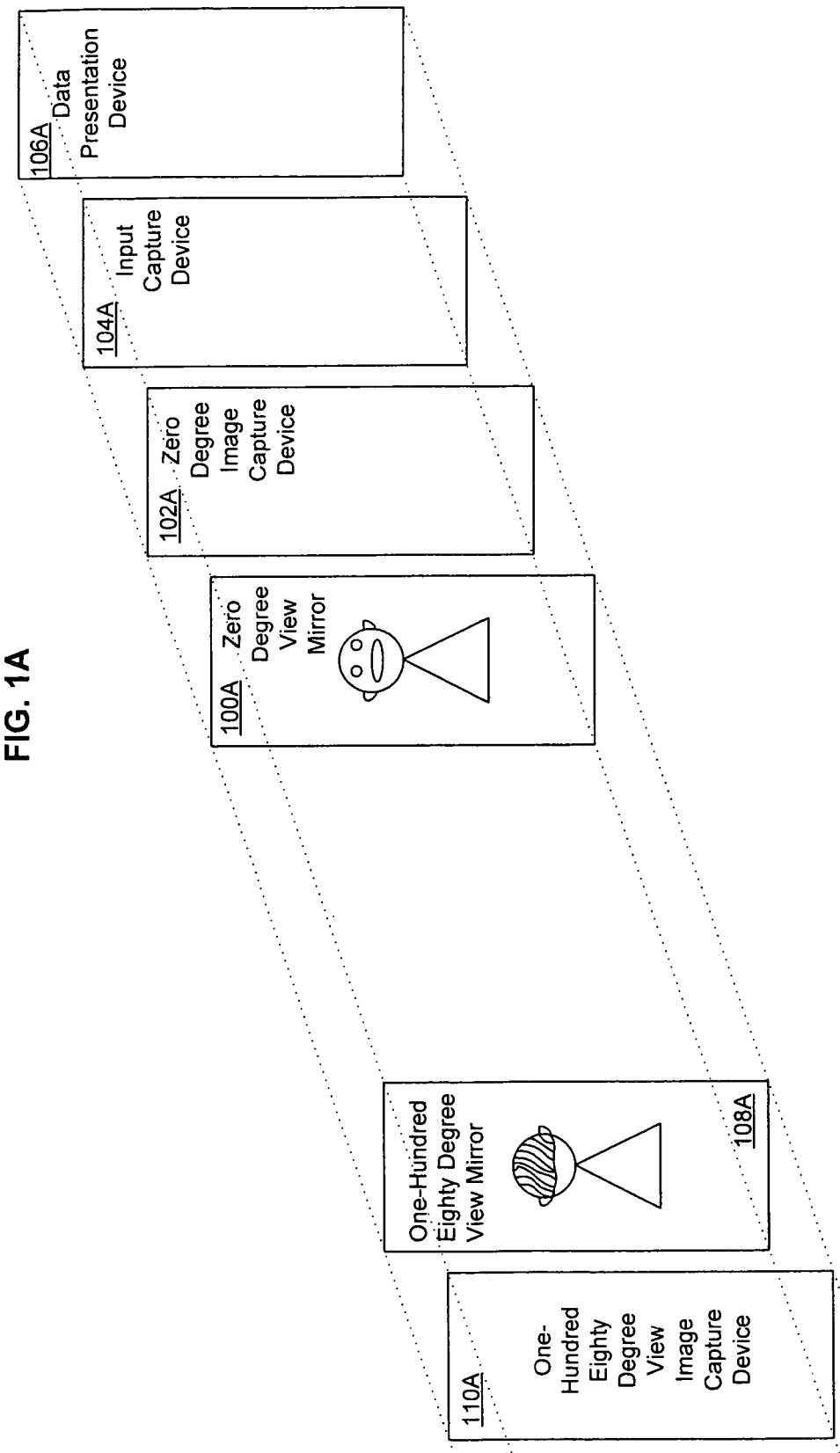

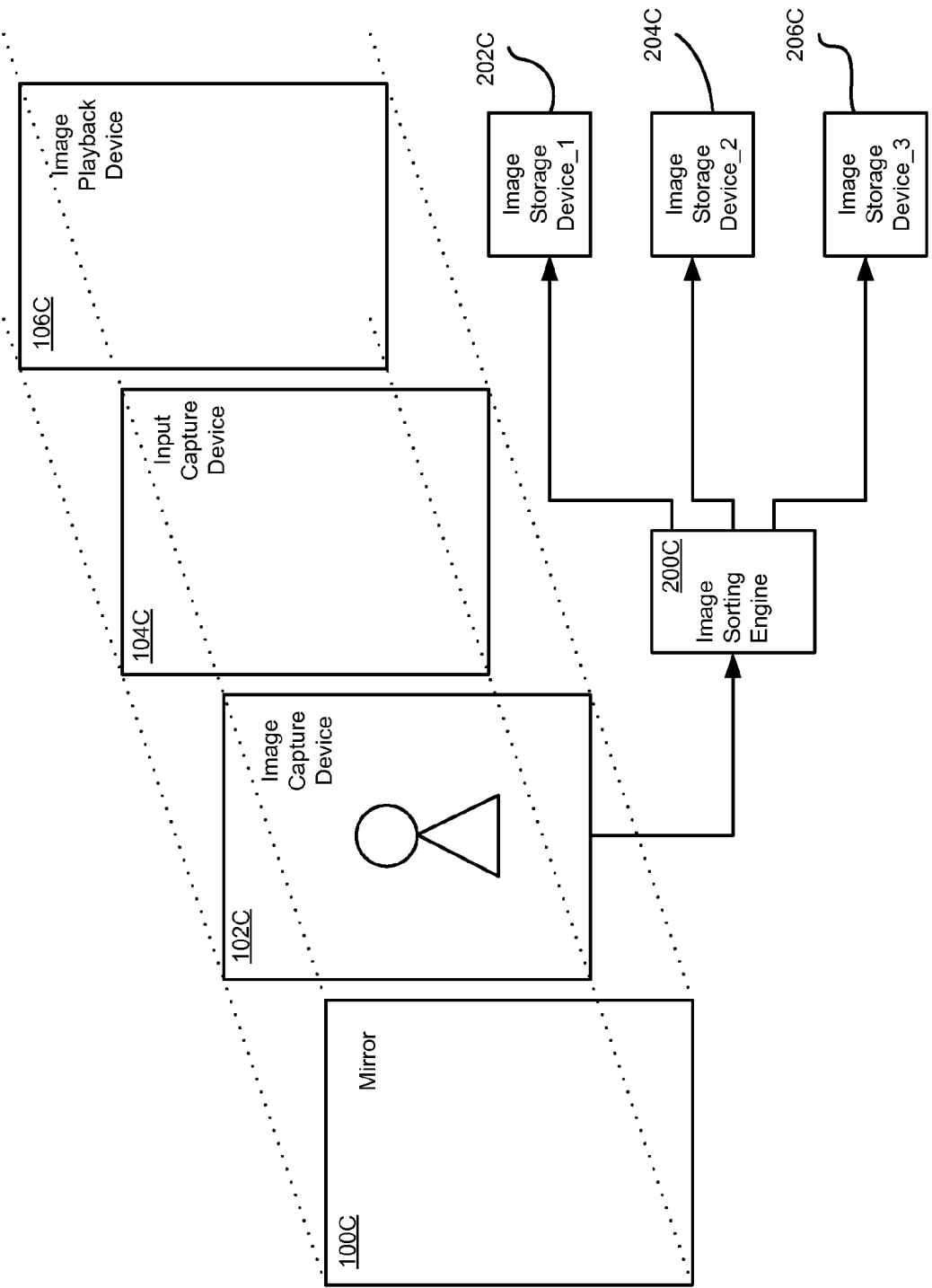

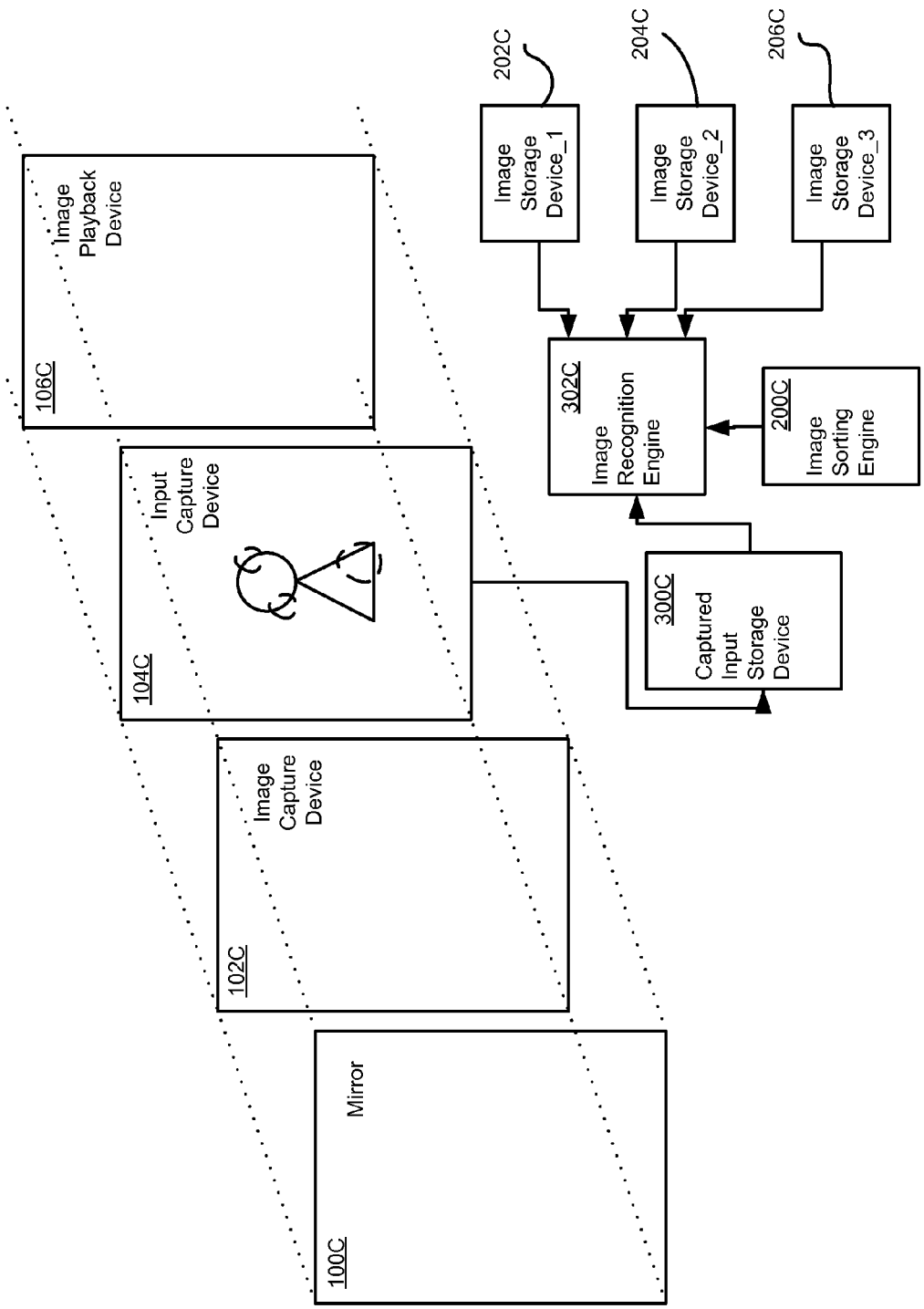

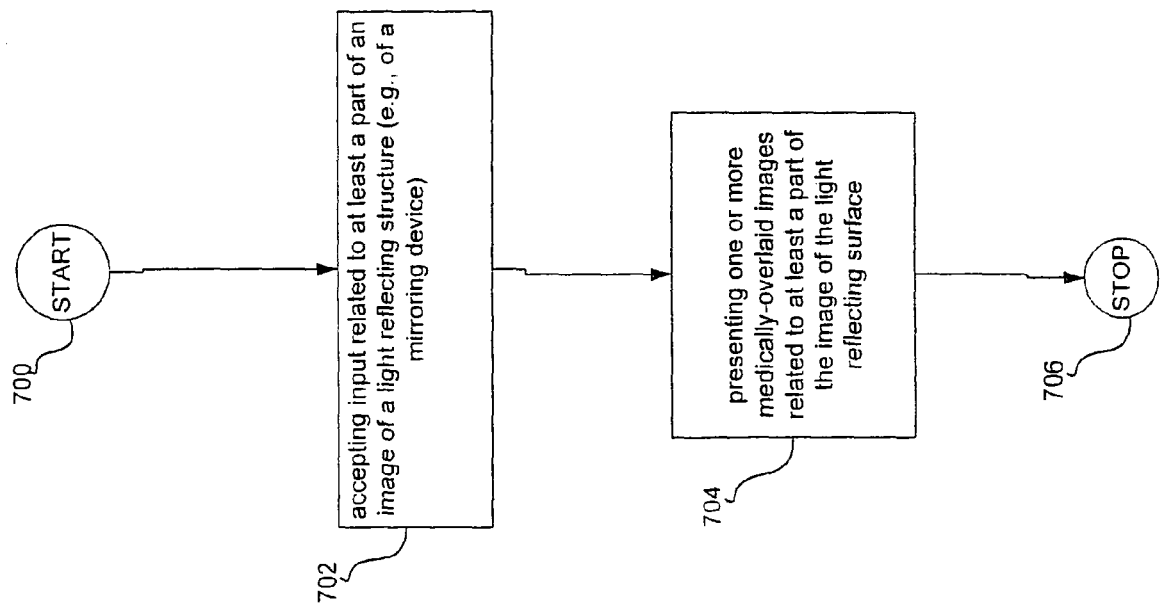

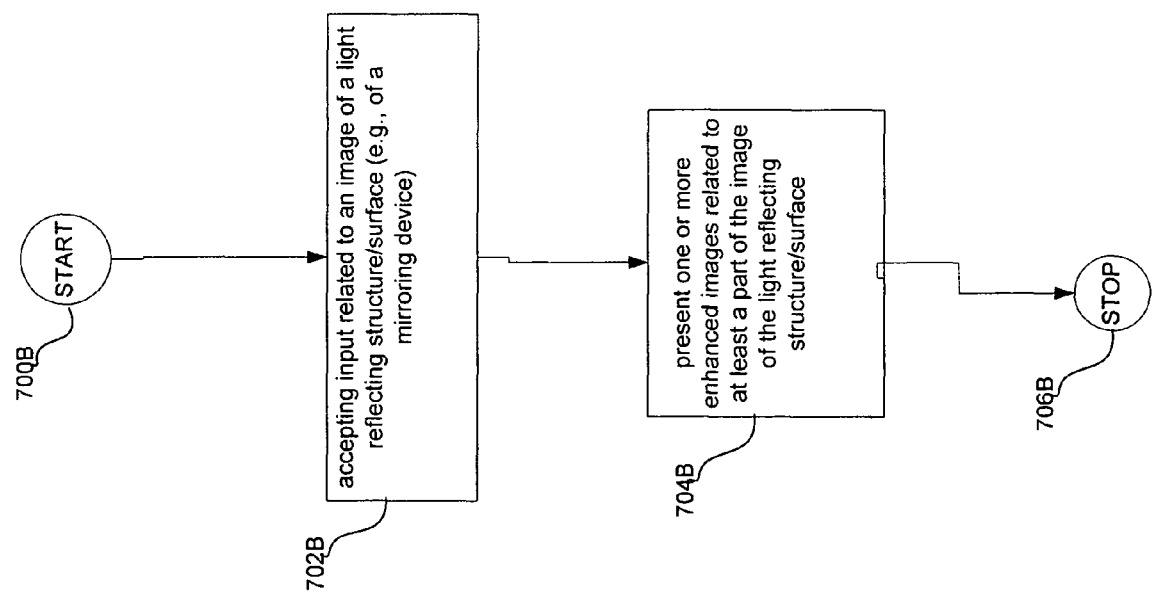

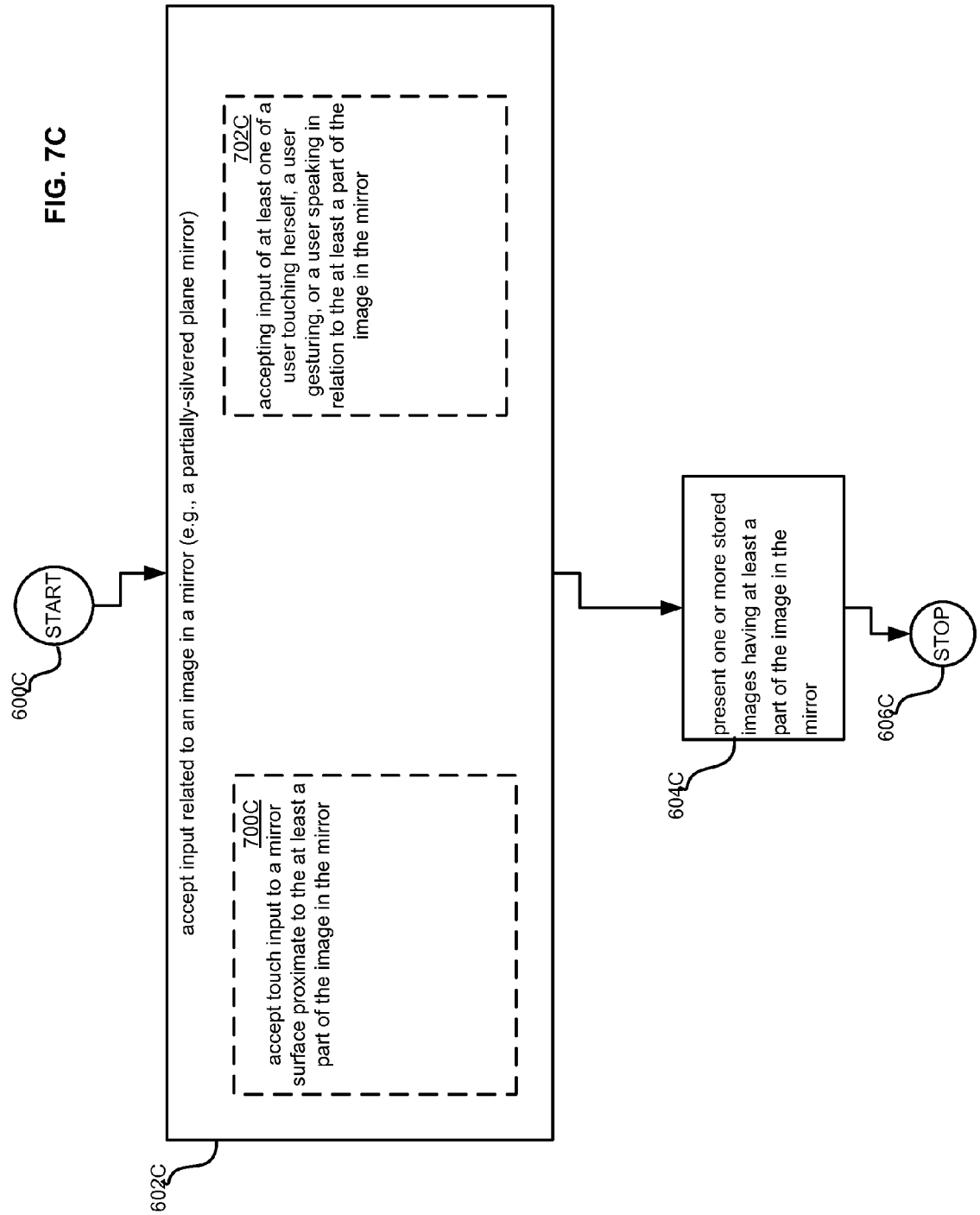

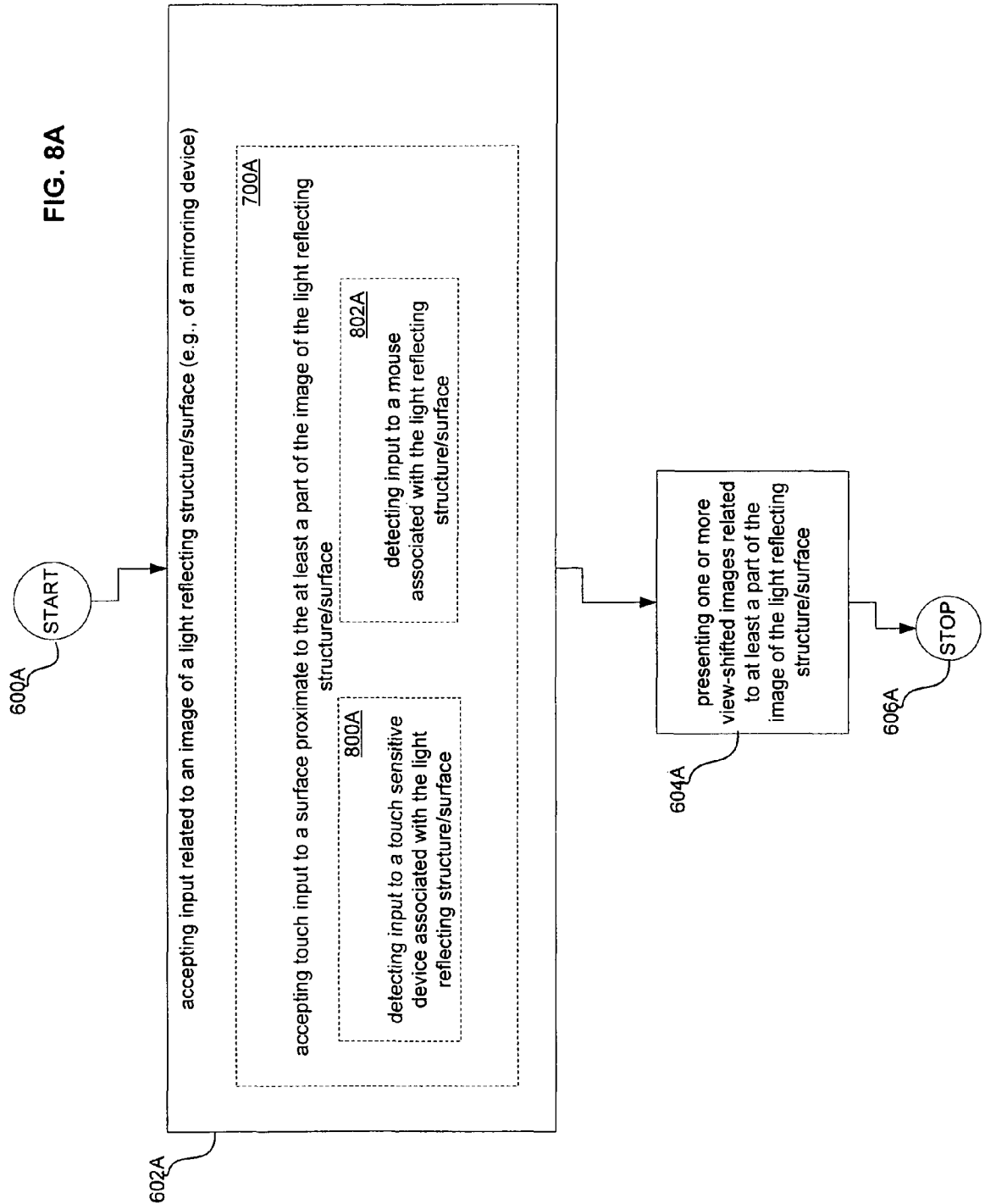

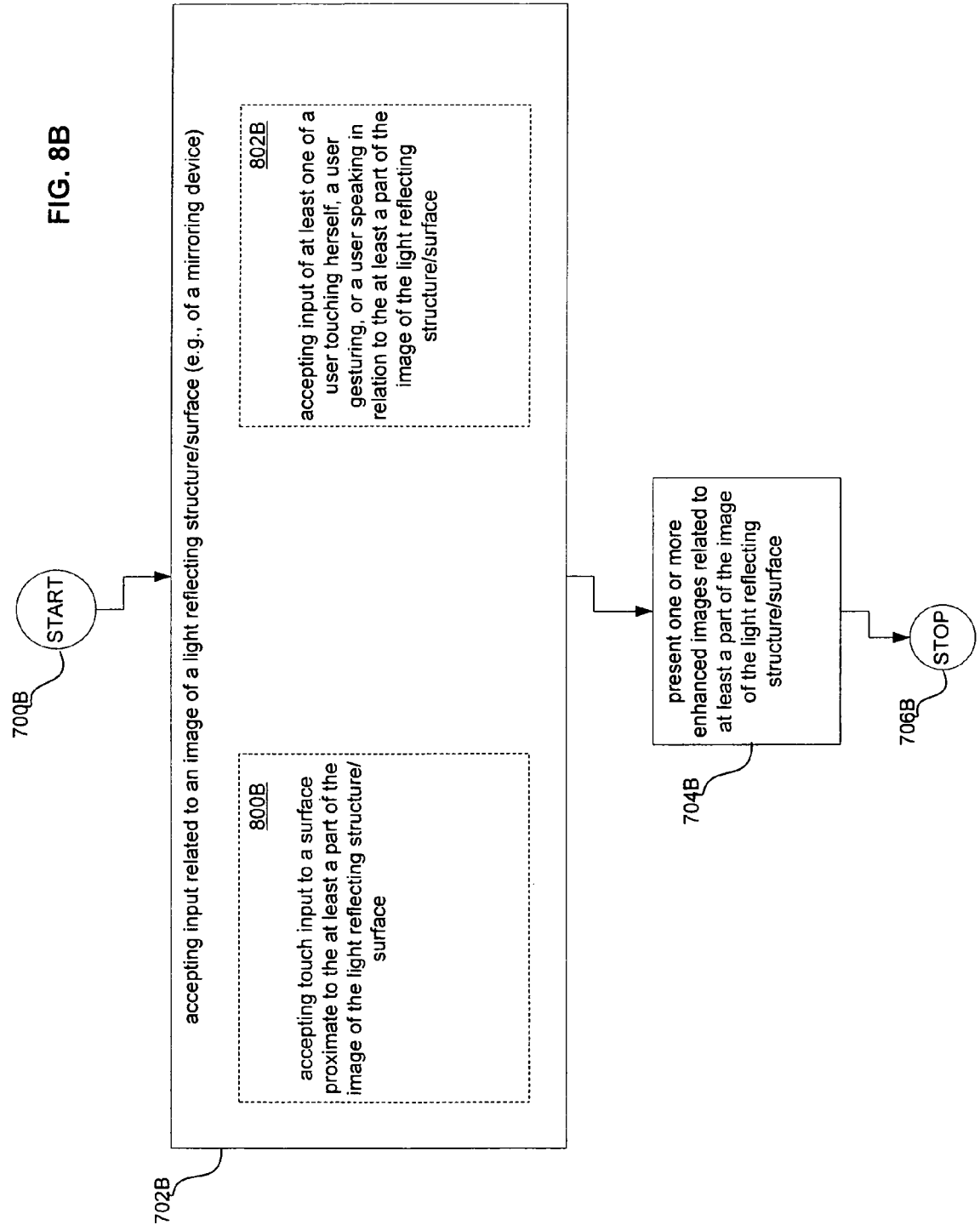

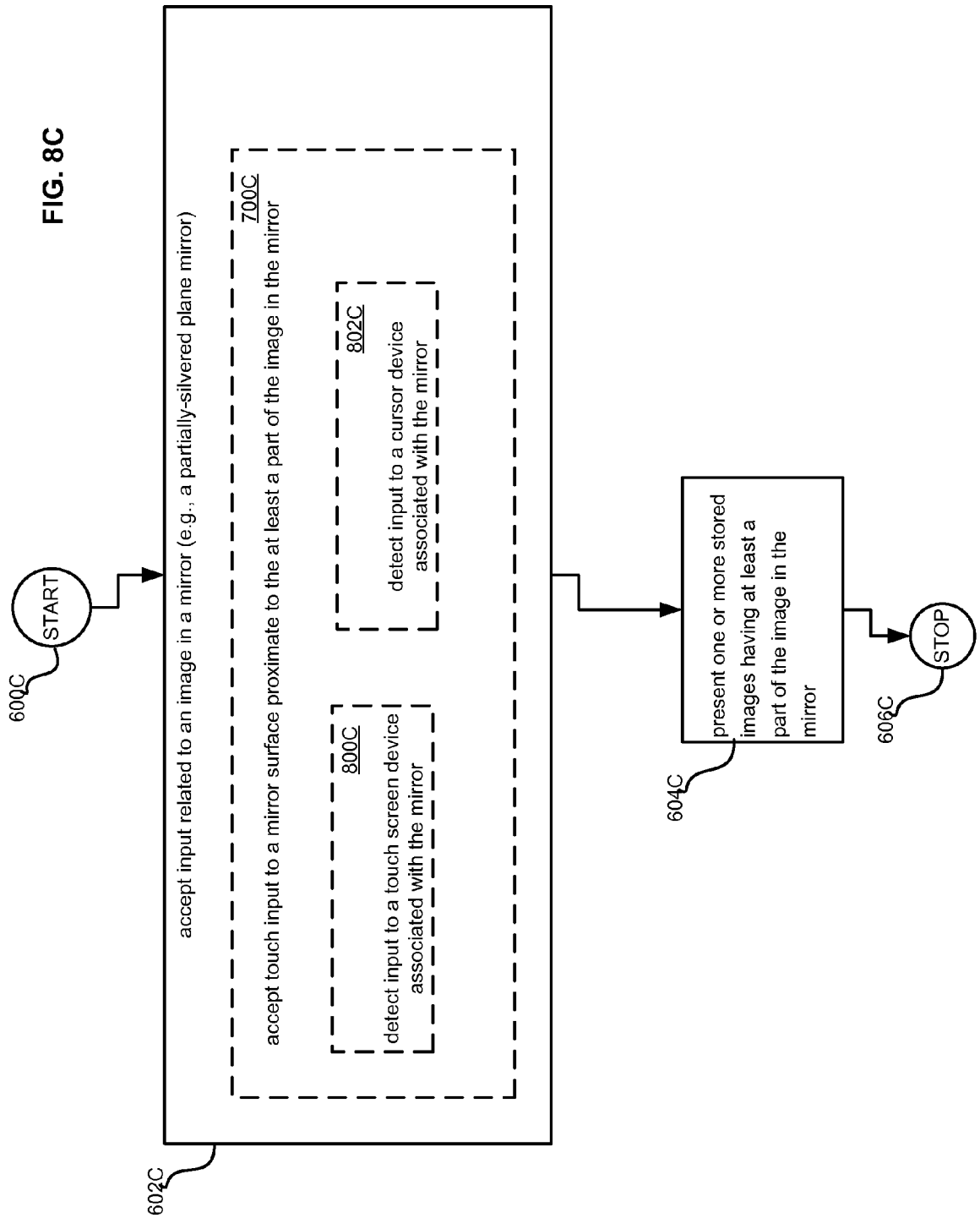

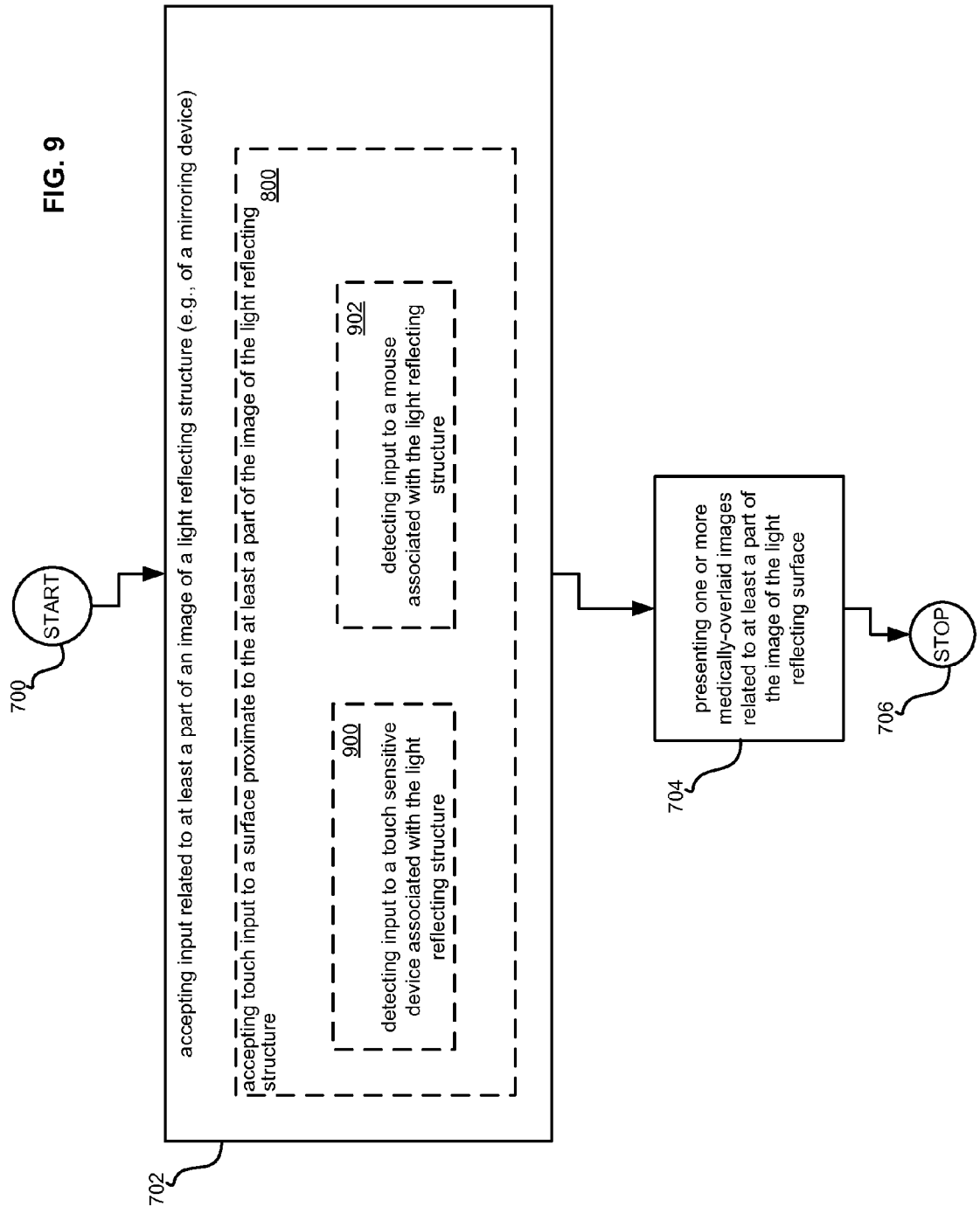

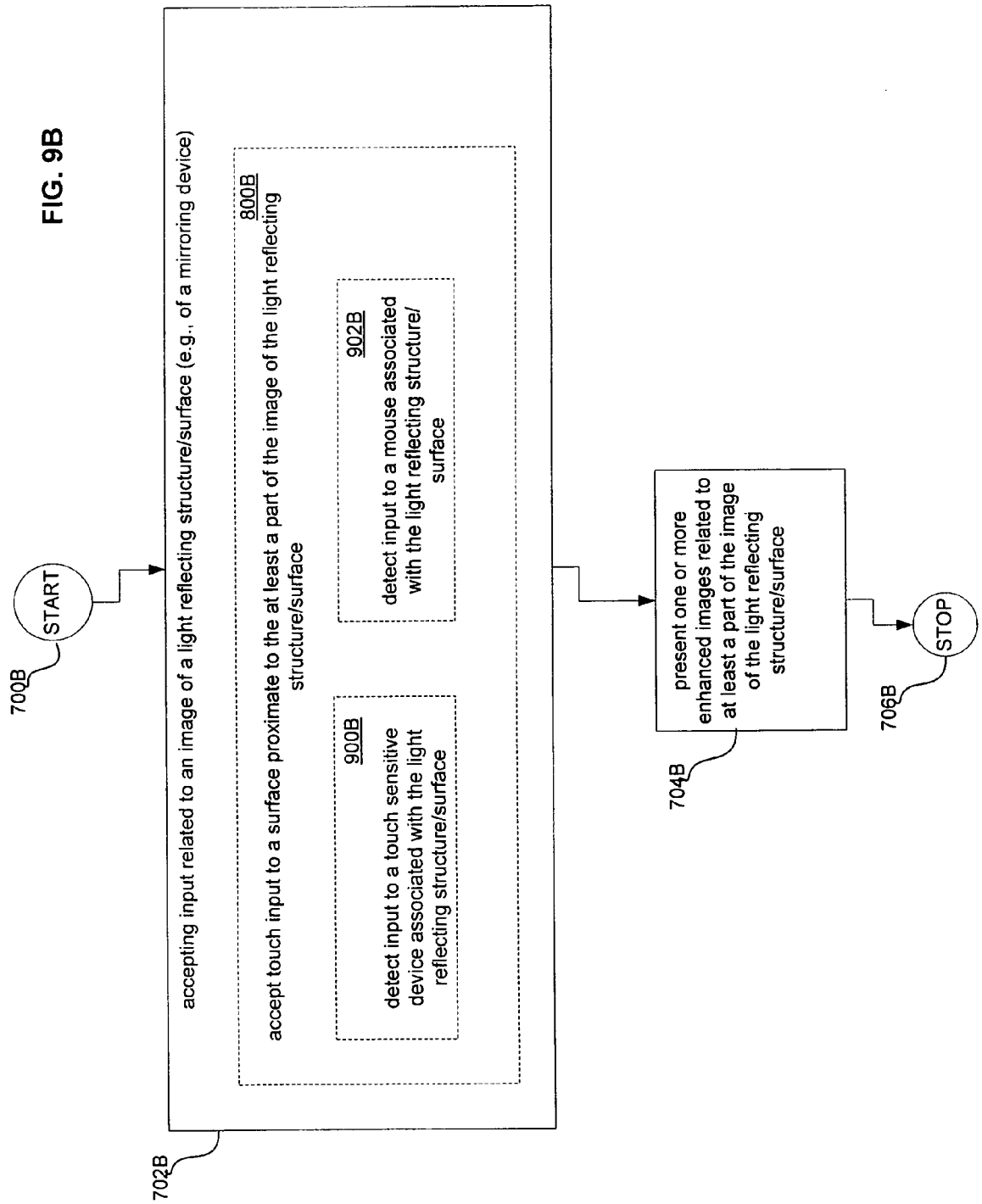

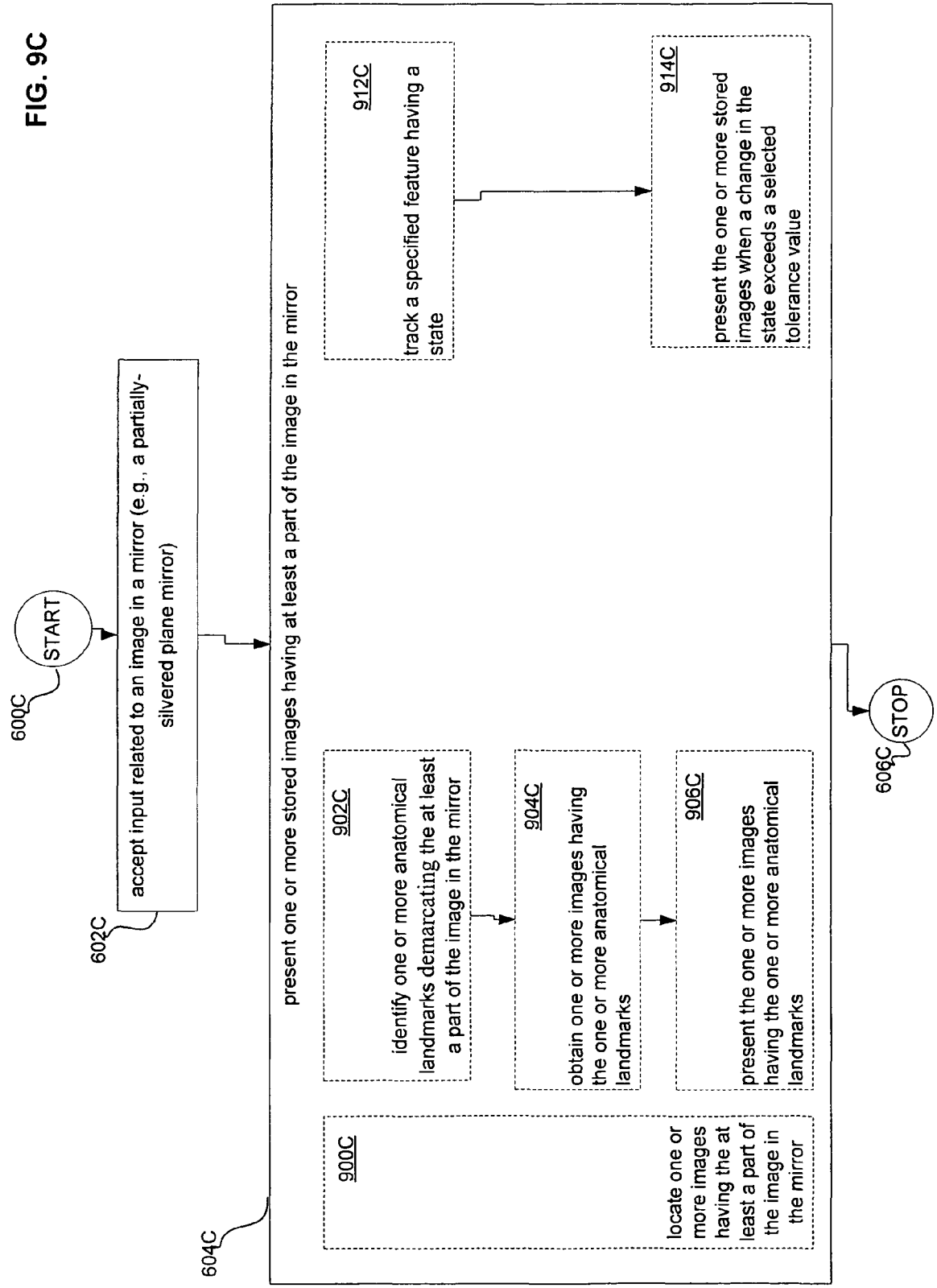

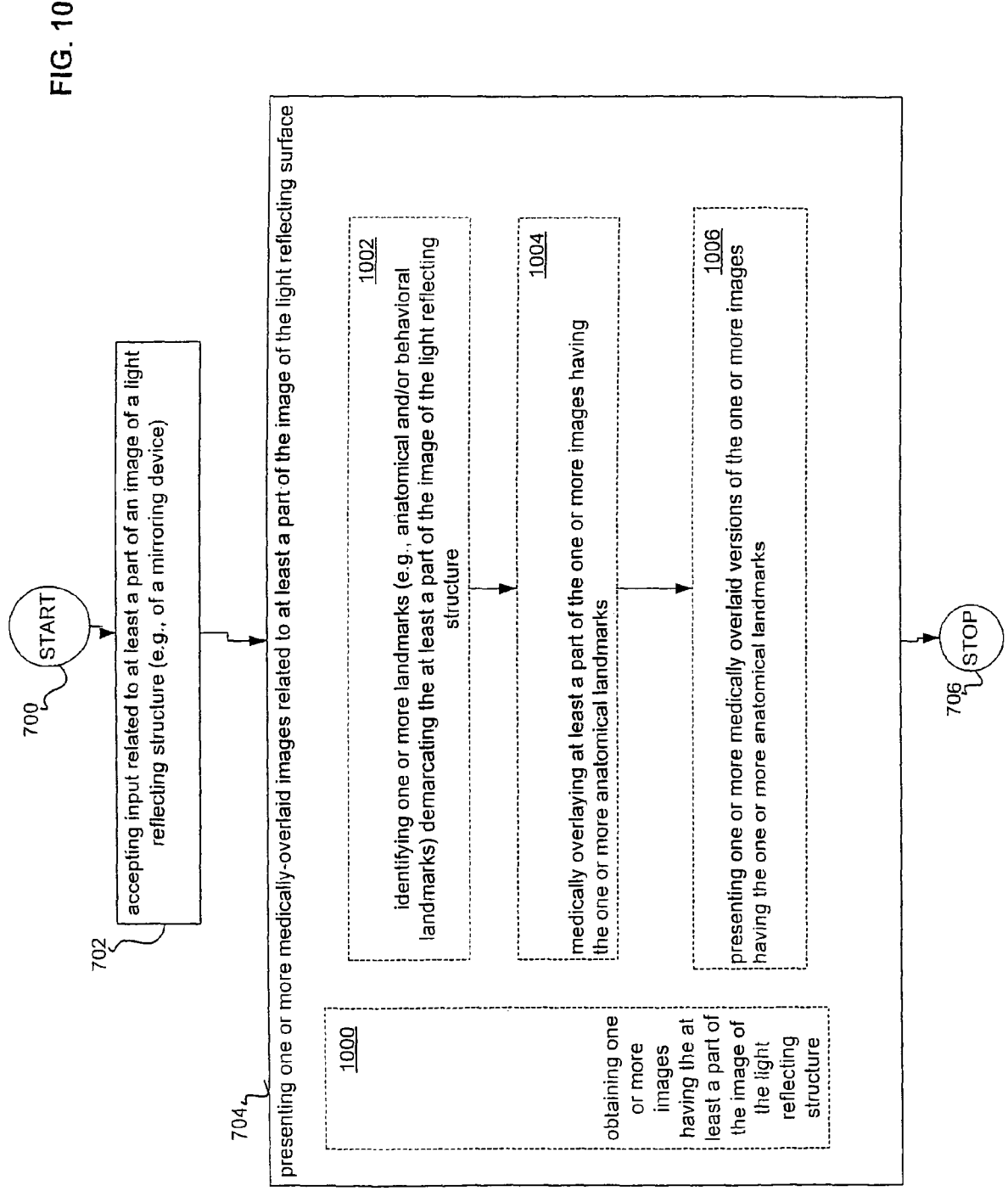

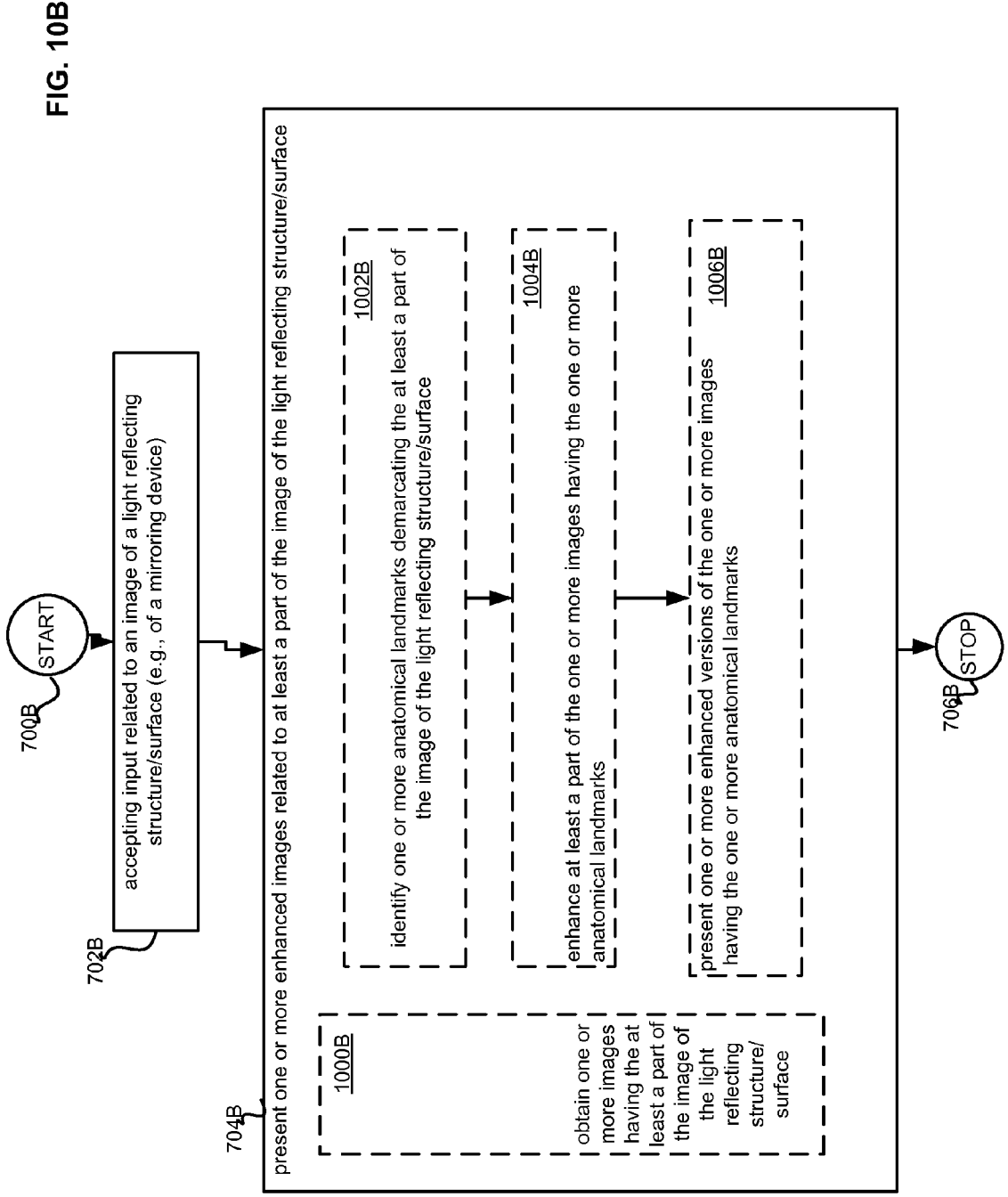

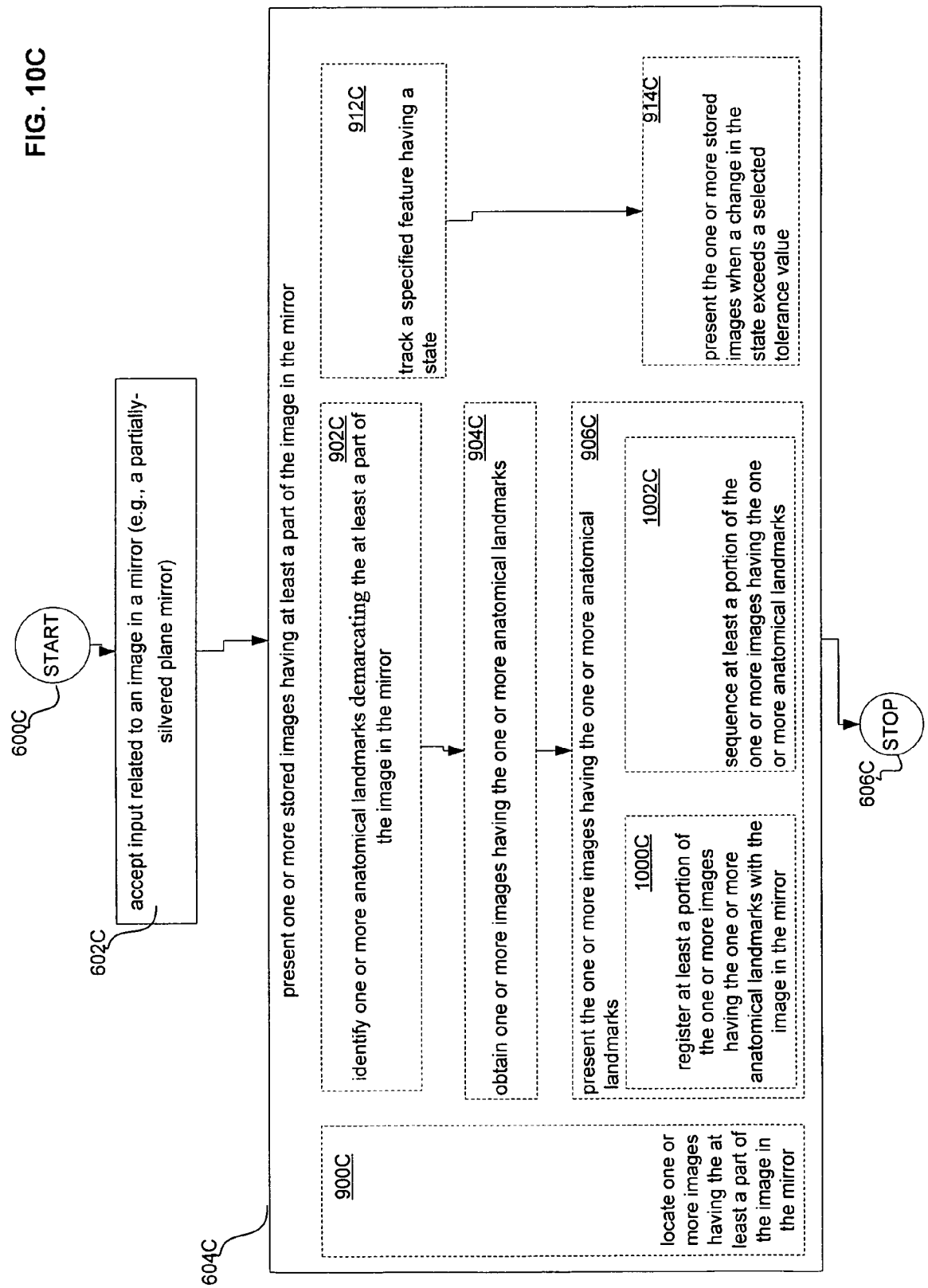

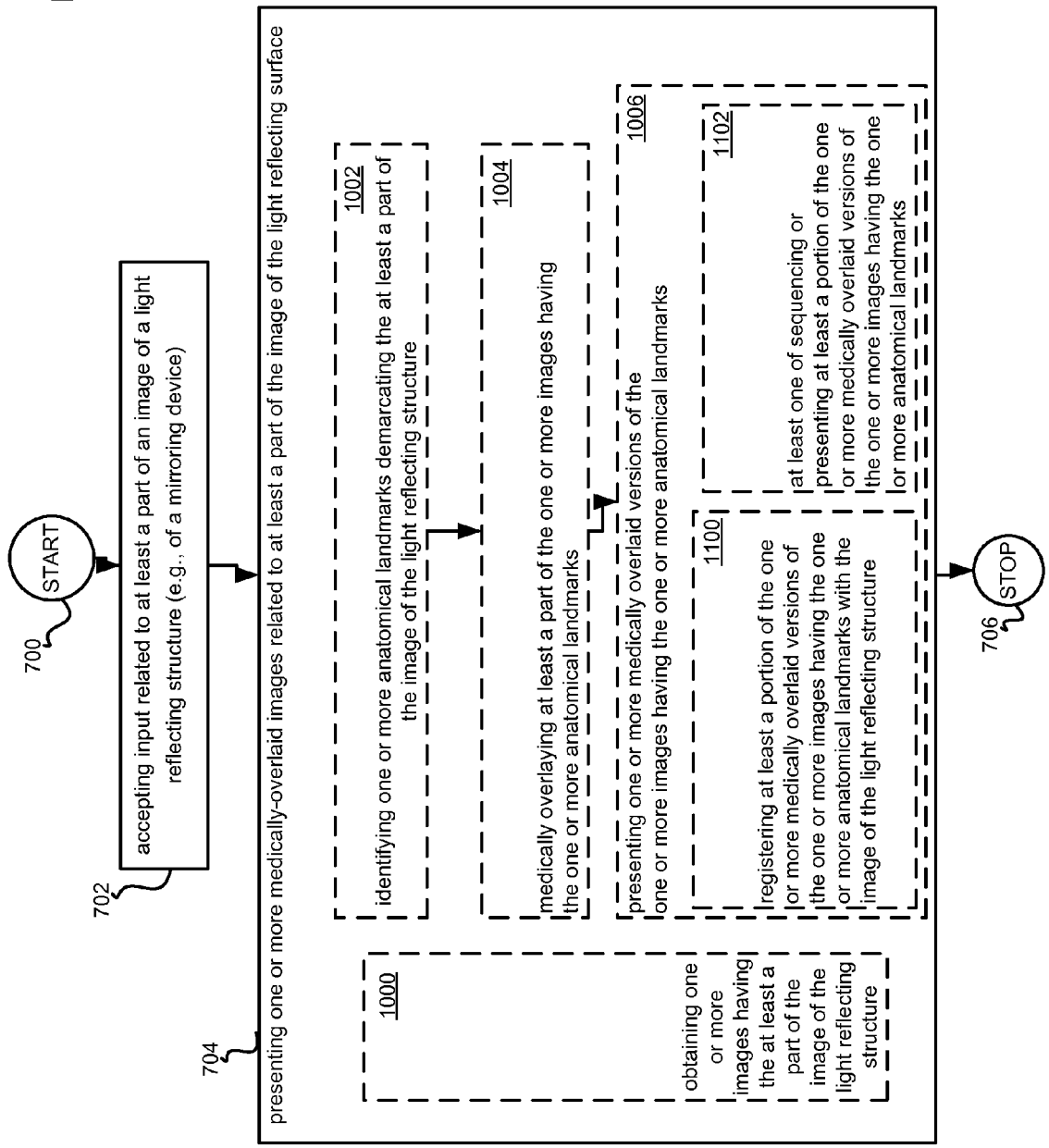

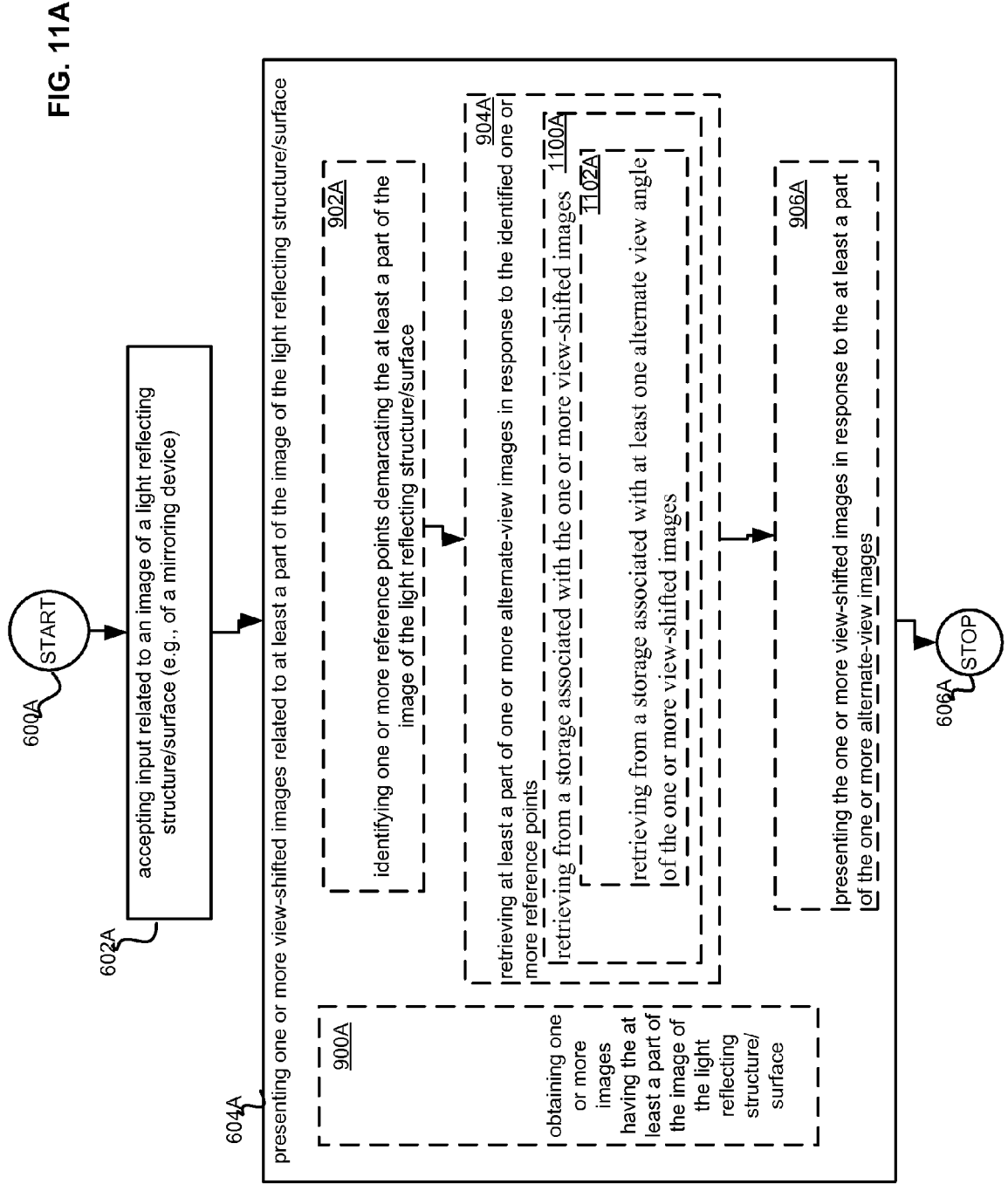

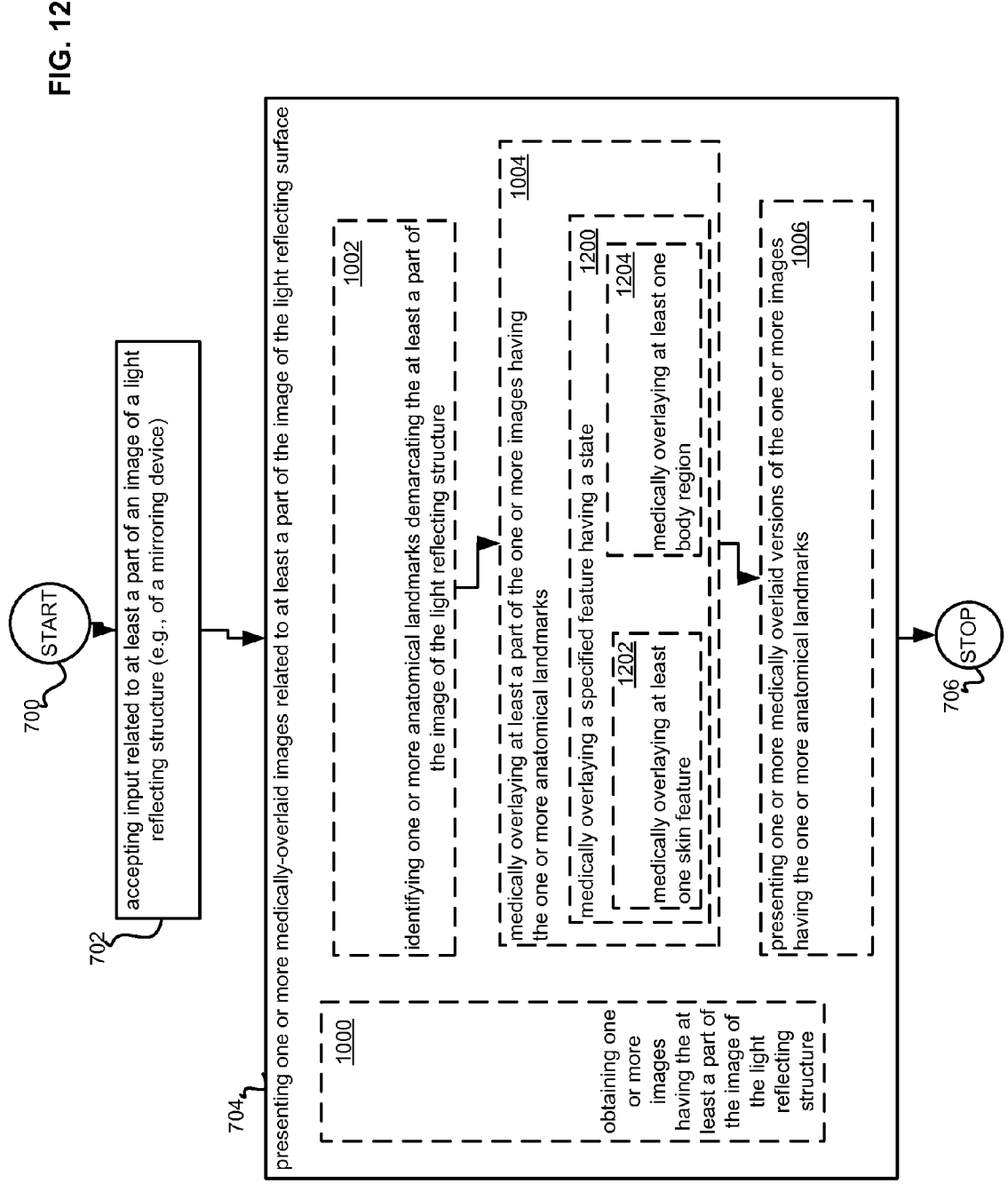

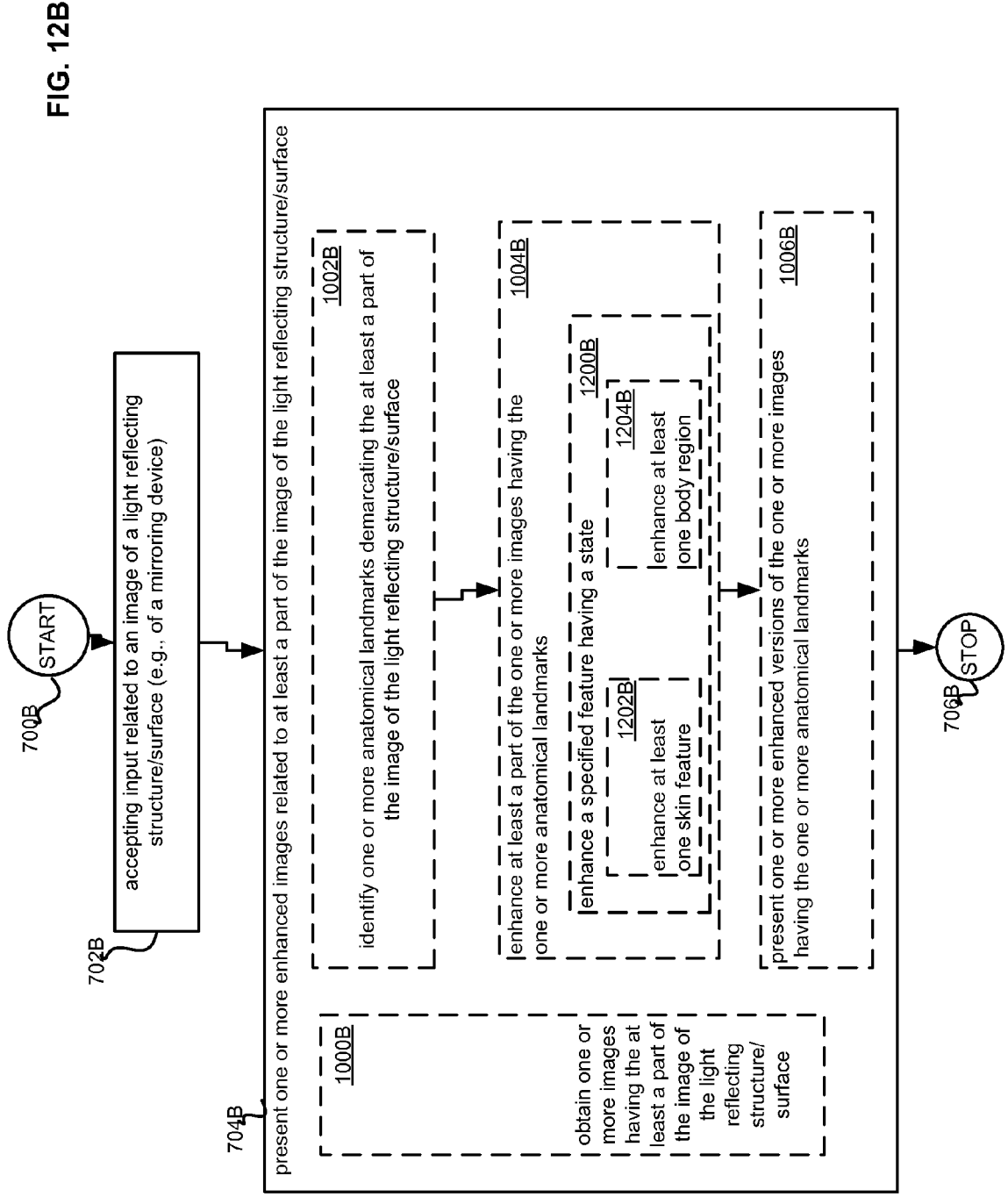

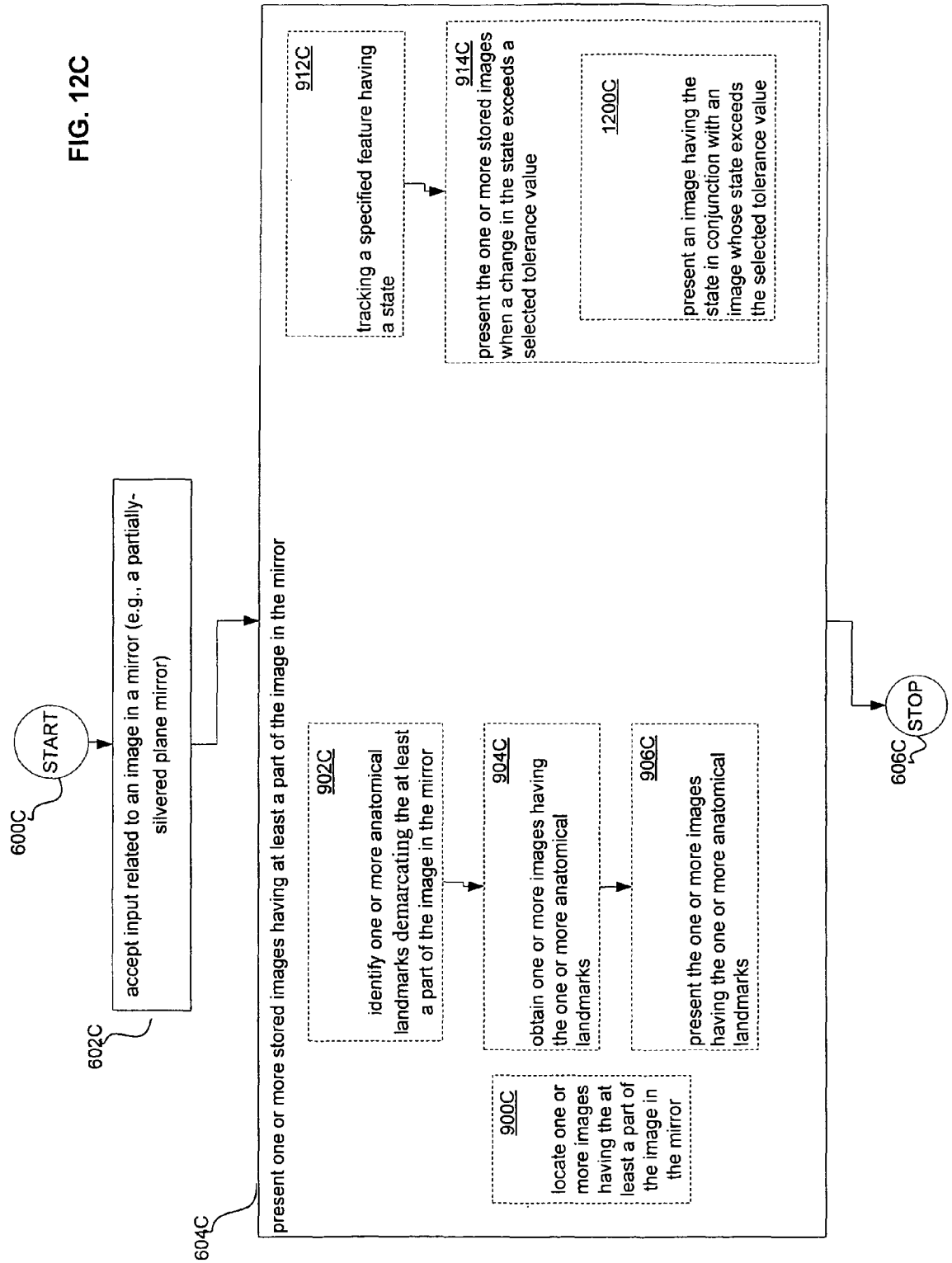

MEDICAL OVERLAY MIRROR

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)), and incorporates by reference in its entirety all subject matter of the following listed application(s) (the "Related Applications"); the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant entity (hereinafter "Applicant") has provided below a specific reference to the application(s) from which priority is being claimed as recited by statute. Applicant understands that the statute is unambiguous in its specific reference language and does not require either a serial number or any characterization such as "continuation" or "continuation-in-part" for claiming priority to U.S. patent applications. Notwithstanding the foregoing, Applicant understands that the USPTO's computer programs have certain data entry requirements, and hence Applicant is designating the present application as a continuation in part/divisional of its parent applications as set forth below, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

RELATED APPLICATIONS

1. For purposes of the USPTO extra-statutory requirements, the present application constitutes a continuation in part of currently United States patent application entitled TIME-LAPSING MIRROR, naming Paul G. Allen, Edward K. Y. Jung, Royce A. Levien, Mark A. Malamud, and John D. Rinaldo, Jr. as inventors, U.S. application Ser. No. 10/910,421 filed 2 Aug. 2004 now U.S. Pat. No. 7,283,106, or is an application of which a currently co-pending application is entitled to the benefit of the filing date.

2. For purposes of the USPTO extra-statutory requirements, the present application constitutes a continuation in part of currently United States patent application entitled COSMETIC ENHANCEMENT MIRROR, naming Paul G. Allen, Edward K. Y. Jung, Royce A. Levien, Mark A. Malamud, and John D. Rinaldo, Jr. as inventors, U.S. application Ser. No. 10/912,271 filed 5 Aug. 2004 now U.S. Pat. No. 7,133,003, or is an application of which a currently co-pending application is entitled to the benefit of the filing date.

3. For purposes of the USPTO extra-statutory requirements, the present application constitutes a continuation in part of currently United States patent application entitled MULTI-ANGLE MIRROR, naming Edward K. Y. Jung, Royce A. Levien, Mark A. Malamud, and John D. Rinaldo, Jr. as inventors, U.S. application Ser. No. 10/941,803 filed 15 Sep. 2004 now U.S. Pat. No. 7,714,804, or is an application of which a currently co-pending application is entitled to the benefit of the filing date.

4. For purposes of the USPTO extra-statutory requirements, the present application constitutes a continuation-in-part of U.S. patent application Ser. No. 10/951,002, entitled MEDICAL OVERLAY MIRROR, naming Paul G. Allen, Edward K. Y. Jung, Royce A. Levien, Mark A. Malamud, and John D. Rinaldo, Jr. as inventors, filed 27 Sep. 2004 now U.S. Pat. No. 7,259,731, or is an application of which a currently co-pending application is entitled to the benefit of the filing date.

5. For purposes of the USPTO extra-statutory requirements, the present application constitutes a continuation-in-part of U.S. patent application Ser. No. 10/972,319, entitled TIME-LAPSING DATA METHODS AND SYSTEMS, naming Paul G. Allen, Edward K. Y. Jung, Royce A. Levien, Mark A. Malamud, and John D. Rinaldo, Jr. as inventors, filed 22 Oct. 2004 now U.S. Pat. No. 7,657,125, or is an application of which a currently co-pending application is entitled to the benefit of the filing date.

6. For purposes of the USPTO extra-statutory requirements, the present application constitutes a continuation in part of U.S. patent application Ser. No. 11/478,334 entitled COSMETIC ENHANCEMENT MIRROR, naming Paul G. Allen, Edward K. Y. Jung, Royce A. Levien, Mark A. Malamud, and John D. Rinaldo, Jr. as inventors, filed 28 Jun. 2006 now U.S. Pat. No. 7,259,732, or is an application of which a currently co-pending application is entitled to the benefit of the filing date.

7. For purposes of the USPTO extra-statutory requirements, the present application constitutes a continuation in part of U.S. patent application Ser. No. 11/540,928 entitled COSMETIC ENHANCEMENT MIRROR, naming Paul G. Allen, Edward K. Y. Jung, Royce A. Levien, Mark A. Malamud, and John D. Rinaldo, Jr. as inventors, filed 28 Sep. 2006 now U.S. Pat. No. 7,429,966, or is an application of which a currently co-pending application is entitled to the benefit of the filing date.

8. For purposes of the USPTO extra-statutory requirements, the present application constitutes a continuation in part of U.S. patent application Ser. No. 11/638,305, entitled TIME-LAPSING MIRROR, naming Paul G. Allen, Edward K. Y. Jung, Royce A. Levien, Mark A. Malamud, and John D. Rinaldo, Jr. as inventors, filed 12 Dec. 2006 now U.S. Pat. No. 7,679,580, or is an application of which a currently co-pending application is entitled to the benefit of the filing date.

9. For purposes of the USPTO extra-statutory requirements, the present application constitutes a divisional of U.S. patent application Ser. No. 11/639,366, entitled MEDICAL OVERLAY MIRROR, naming Paul G. Allen, Edward K. Y. Jung, Royce A. Levien, Mark A. Malamud, and John D. Rinaldo, Jr. as inventors, filed 13 Dec. 2006 now U.S. Pat. No. 7,679,581, or is an application of which a currently co-pending application is entitled to the benefit of the filing date.

10. For purposes of the USPTO extra-statutory requirements, the present application constitutes a continuation in part of U.S. patent application Ser. No. 11/726,114, entitled COSMETIC ENHANCEMENT MIRROR, naming Paul G. Allen, Edward K. Y. Jung, Royce A. Levien, Mark A. Malamud, and John D. Rinaldo, Jr. as inventors, filed 20 Mar. 2007, which is currently co-pending, or is an application of which a currently co-pending application is entitled to the benefit of the filing date.

11. For purposes of the USPTO extra-statutory requirements, the present application constitutes a continuation-in-part of U.S. patent application Ser. No. 11/982,731, entitled MEDICAL OVERLAY MIRROR, naming Paul G. Allen, Edward K. Y. Jung, Royce A. Levien, Mark A. Malamud, and John D. Rinaldo, Jr. as inventors, filed 1 Nov. 2007 now U.S. Pat. No. 7,692,606, or is an application of which a currently co-pending application is entitled to the benefit of the filing date.

12. For purposes of the USPTO extra-statutory requirements, the present application constitutes a continuation in part of U.S. patent application Ser. No. 11/981,805, entitled TIME-LAPSING MIRROR, naming Paul G. Allen, Edward K. Y. Jung, Royce A. Levien, Mark A. Malamud, and John D. Rinaldo, Jr. as inventors, filed 30 Oct. 2007 now U.S. Pat. No. 7,663,571, or is an application of which a currently co-pending application is entitled to the benefit of the filing date.

13. For purposes of the USPTO extra-statutory requirements, the present application constitutes a continuation in part of U.S. patent application Ser. No. 11/982,326 entitled COSMETIC ENHANCEMENT MIRROR, naming Paul G. Allen, Edward K. Y. Jung, Royce A. Levien, Mark A. Malamud, and John D. Rinaldo, Jr. as inventors, filed 31 Oct. 2007 now U.S. Pat. No. 7,683,858, or is an application of which a currently co-pending application is entitled to the benefit of the filing date.

14. For purposes of the USPTO extra-statutory requirements, the present application constitutes a continuation in part of U.S. patent application Ser. No. 11/982,396 entitled MULTI-ANGLE MIRROR, naming Edward K. Y. Jung, Royce A. Levien, Mark A. Malamud, and John D. Rinaldo, Jr. as inventors, filed 31 Oct. 2007 now U.S. Pat. No. 7,705,800, or is an application of which a currently co-pending application is entitled to the benefit of the filing date.

15. For purposes of the USPTO extra-statutory requirements, the present application constitutes a continuation in part of U.S. patent application Ser. No. 12/154,694 entitled COSMETIC ENHANCEMENT MIRROR, naming Paul G. Allen, Edward K. Y. Jung, Royce A. Levien, Mark A. Malamud, and John D. Rinaldo, Jr. as inventors, filed 22 May 2008 now U.S. Pat. No. 7,636,072, or is an application of which a currently co-pending application is entitled to the benefit of the filing date.

16. For purposes of the USPTO extra-statutory requirements, the present application constitutes a continuation-in-part of U.S. patent application Ser. No. 12/220,671, entitled TIME-LAPSING DATA METHODS AND SYSTEMS, naming Paul G. Allen, Edward K. Y. Jung, Royce A. Levien, Mark A. Malamud, and John D. Rinaldo, Jr. as inventors, filed 25 Jul. 2008, which is currently co-pending, or is an application of which a currently co-pending application is entitled to the benefit of the filing date.

17. For purposes of the USPTO extra-statutory requirements, the present application constitutes a continuation in part of U.S. patent application Ser. No. 12/286,556 entitled MULTI-ANGLE MIRROR, naming Edward K. Y. Jung, Royce A. Levien, Mark A. Malamud, and John D. Rinaldo, Jr. as inventors, filed 29 Sep. 2008 now U.S. Pat. No. 7,671,823, or is an application of which a currently co-pending application is entitled to the benefit of the filing date.

18. For purposes of the USPTO extra-statutory requirements, the present application constitutes a continuation in part of U.S. patent application Ser. No. 12/286,547 entitled MULTI-ANGLE MIRROR, naming Edward K. Y. Jung, Royce A. Levien, Mark A. Malamud, and John D. Rinaldo, Jr. as inventors, filed 29 Sep. 2008, which is currently co-pending, or is an application of which a currently co-pending application is entitled to the benefit of the filing date.

19. For purposes of the USPTO extra-statutory requirements, the present application constitutes a continuation in part of U.S. patent application Ser. No. 12/658,260 entitled MEDICAL OVERLAY MIRROR, naming Paul G. Allen, Edward K. Y. Jung, Royce A. Levien, Mark A. Malamud, and John D. Rinaldo, Jr. as inventors, filed 3 Feb. 2010, which is currently co-pending, or is an application of which a currently co-pending application is entitled to the benefit of the filing date.

TECHNICAL FIELD

The present application relates, in general, to mirror technologies.

SUMMARY

In one aspect, a system includes but is not limited to a light reflecting structure; a data presentation device proximate to said light reflecting structure; and a medical overlay engine operably couplable to said data presentation device. In addition to the foregoing, other system aspects are described in the claims, drawings, and text forming a part of the present application.

In one aspect, a system includes but is not limited to a light reflecting surface; an image representation capture device having an image field corresponding to said light reflecting surface; and at least one medical-overlaid image reception device operably couplable with said image representation capture device. In addition to the foregoing, other system aspects are described in the claims, drawings, and text forming a part of the present application.

In one aspect, a method includes but is not limited to accepting input related to at least a part of an image of a light reflecting structure; and presenting one or more medically-overlaid images related to at least a part of the image of the light reflecting structure. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to: a digital mirror; a data presentation device proximate to said digital mirror; and a medical overlay engine operably couplable to said data presentation device. In addition to the foregoing, other system aspects are described in the claims, drawings, and text forming a part of the present application.

In one aspect, a system includes but is not limited to at least one mirror; a data presentation device proximate to said at least one mirror; and a multi-angle view/registration engine operably couplable to said data presentation device. In addition to the foregoing, other system aspects are described in the claims, drawings, and text forming a part of the present application.

In one aspect, a system includes but is not limited to a mirror; and an offset-view image representation capture device having an image field different from an image field corresponding to said mirror. In addition to the foregoing, other system aspects are described in the claims, drawings, and text forming a part of the present application.

In one aspect, a method includes but is not limited to accepting input related to an image of a light reflecting structure/surface; and presenting one or more view-shifted images related to at least a part of the image of the light reflecting structure/surface. In addition to the foregoing, other method aspects are described in the claims, drawings, and text forming a part of the present application.

In one or more various aspects, related systems include but are not limited to circuitry and/or programming for effecting the herein referenced method aspects; the circuitry and/or programming can be virtually any combination of hardware, software, and/or firmware configured to effect the herein-referenced method aspects depending upon the design choices of the system designer.

In one aspect, a system includes but is not limited to a digital mirror; a data presentation device proximate to said digital mirror; and a multi-angle view engine operably couplable to said data presentation device. In addition to the foregoing, other system aspects are described in the claims, drawings, and text forming a part of the present application.

In one aspect, a system includes but is not limited to a light reflecting structure; a data presentation device proximate to said light reflecting structure; and an image enhancement engine operably couplable to said data presentation device. In addition to the foregoing, other system aspects are described in the claims, drawings, and text forming a part of the present application.

In one aspect, a system includes but is not limited to a light reflecting surface; an image representation capture device having an image field corresponding to said light reflecting surface; and at least one modified image reception device operably couplable with said image representation capture device. In addition to the foregoing, other system aspects are described in the claims, drawings, and text forming a part of the present application.

In one aspect, a method includes but is not limited to accepting input related to an image of a light reflecting surface; and presenting one or more enhanced images related to at least a part of the image of the light reflecting surface. In addition to the foregoing, other method aspects are described in the claims, drawings, and text forming a part of the present application.

In one or more various aspects, related systems include but are not limited to circuitry and/or programming for effecting the herein referenced method aspects; the circuitry and/or programming can be virtually any combination of hardware, software, and/or firmware configured to effect the herein-referenced method aspects depending upon the design choices of the system designer.

In one aspect, a system includes but is not limited to a physical mirror; an image playback device proximate to said physical mirror; and an image registration engine operably couplable to said image playback device. In addition to the foregoing, other system aspects are described in the claims, drawings, and text forming a part of the present application.

In one aspect, a system includes but is not limited to a physical mirror; an image capture device having an image field corresponding to said physical mirror; and at least one image storage device operably couplable with said image capture device. In addition to the foregoing, other system aspects are described in the claims, drawings, and text forming a part of the present application.

In one aspect, a method includes but is not limited to accepting input related to an image in a mirror; and presenting one or more stored images having at least a part of the image in the mirror. In addition to the foregoing, other method aspects are described in the claims, drawings, and text forming a part of the present application.

In one or more various aspects, related systems include but are not limited to circuitry and/or programming for effecting the herein referenced method aspects; the circuitry and/or programming can be virtually any combination of hardware, software, and/or firmware configured to effect the herein-referenced method aspects depending upon the design choices of the system designer.

In addition to the foregoing, various other method and/or system aspects are set forth and described in the text (e.g., claims and/or detailed description) and/or drawings of the present application.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the detailed description set forth herein.

BRIEF DESCRIPTION OF THE FIGURES

FIG. 1 shows a partial view of a system that may serve as an illustrative environment of and/or for subject matter technologies.

FIG. 7 illustrates a high-level logic flowchart of a process.

FIG. 9 depicts a high-level logic flowchart depicting alternate implementations of the high-level logic flowchart of FIG. 8.

FIG. 10 illustrates a high-level logic flowchart depicting alternate implementations of the high-level logic flowchart of FIG. 7.

FIG. 11 shows a high-level logic flowchart depicting alternate implementations of the high-level logic flowchart of FIG. 10.

FIG. 12 illustrates a high-level logic flowchart depicting several alternate implementations of the high-level logic flowchart of FIG. 10.

FIG. 1A shows a partial view of a system that may serve as an illustrative environment of and/or for subject matter technologies.

FIG. 8A depicts a high-level logic flowchart depicting alternate implementations of the high-level logic flowchart of FIG. 7A.

FIG. 11A depicts a high-level logic flowchart depicting several alternate implementations of the high-level logic flowchart of FIG. 10A.

FIG. 7B illustrates a high-level logic flowchart of a process.

FIG. 8B shows a high-level logic flowchart depicting alternate implementations of the high-level logic flowchart of FIG. 7B.

FIG. 9B depicts a high-level logic flowchart depicting alternate implementations of the high-level logic flowchart of FIG. 8B.

FIG. 10B illustrates a high-level logic flowchart depicting alternate implementations of the high-level logic flowchart of FIG. 7B.

FIG. 12B illustrates a high-level logic flowchart depicting several alternate implementations of the high-level logic flowchart of FIG. 10B.

FIG. 2C depicts a partial view of a system that may serve as an illustrative environment of and/or for subject matter technologies.

FIG. 3C illustrates a partial view of a system that may serve as an illustrative environment of and/or for subject matter technologies.

FIG. 7C shows a high-level logic flowchart depicting alternate implementations of the high-level logic flowchart of FIG. 6C.

FIG. 8C depicts a high-level logic flowchart depicting alternate implementations of the high-level logic flowchart of FIG. 7C.

FIG. 9C illustrates a high-level logic flowchart depicting alternate implementations of the high-level logic flowchart of FIG. 6C.

FIG. 10C shows a high-level logic flowchart depicting alternate implementations of the high-level logic flowchart of FIG. 9C.

FIG. 12C illustrates a high-level logic flowchart depicting an alternate implementation of the high-level logic flowchart of FIG. 9C.

The use of the same symbols in different drawings typically indicates similar or identical items.

DETAILED DESCRIPTION

Figure 1B:
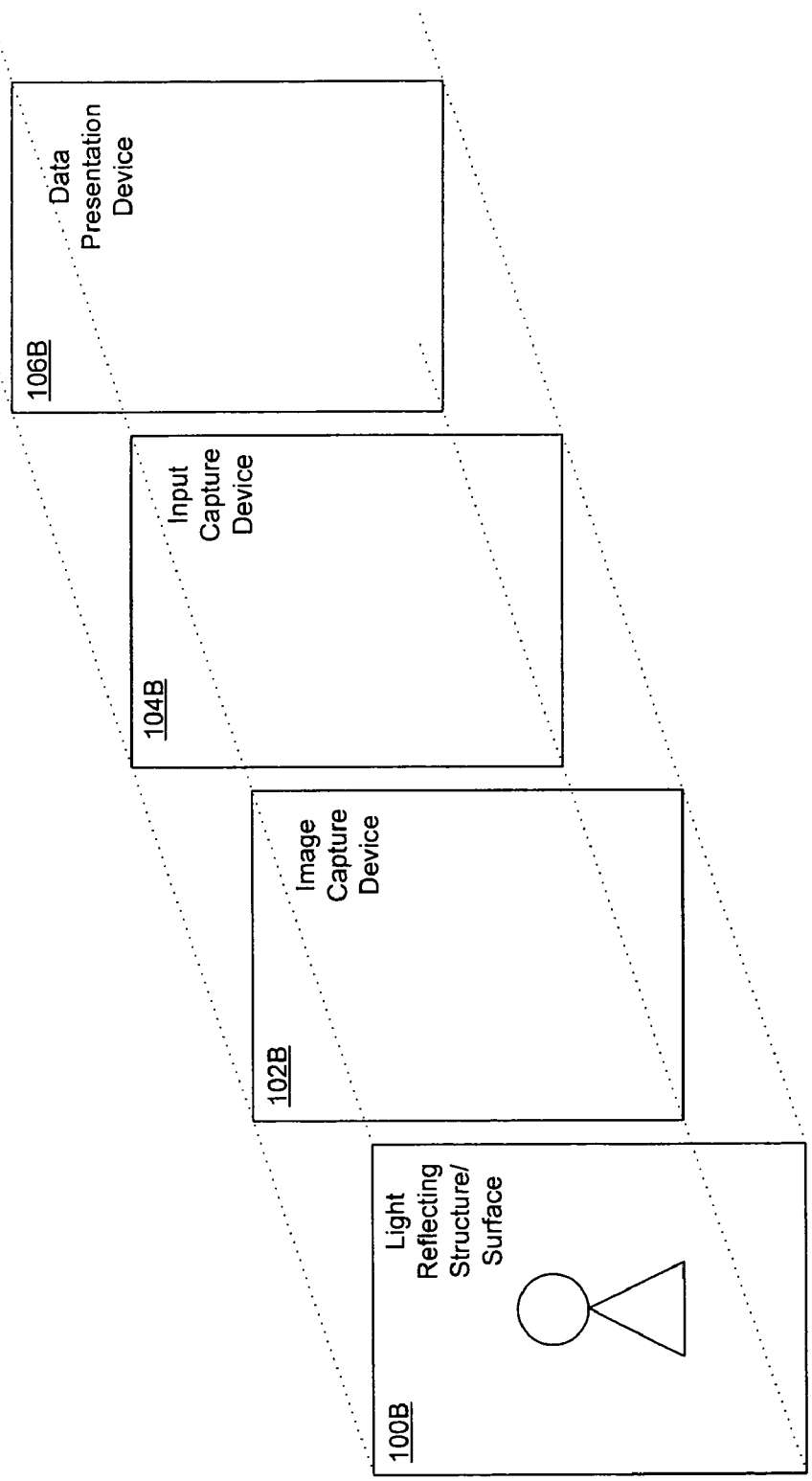
FIG. 1B shows a partial view of a system that may serve as an illustrative environment of and/or for subject matter technologies.

With reference to the figures, and with reference now to FIG. 1, shown is a partial view of a system that may serve as an illustrative environment of and/or for subject matter technologies. Depicted are light reflecting structure 100, image capture device 102, input capture device 104, and data presentation device 106. In one exemplary implementation, light reflecting structure 100 can be a plane mirror, a convex mirror, and/or a concave mirror. In another exemplary implementation, light reflecting structure 100 can be a partially silvered mirror. In some exemplary implementations, light reflecting structure 100 can be a physical mirror. In other exemplary implementations, light reflecting structure 100 can be a digital mirror and/or a projection mirror. In yet other implementations, light reflecting structure 100 can be a combination of one or more physical mirrors and/or one or more digital mirrors and/or one or more projection mirrors. In some implementations, data presentation device 106 may present various types of time-lapse information in addition or in the alternative to image information, such as height and/or weight information. In some implementations, presentations of information may be in the form of various modalities including but not limited to graphs, tables, audio (speech, music, sound), text, store-and-forward formats (e.g., email, voicemail, and/or simple message system mail at various reporting intervals, such as in a weekly digest format), database formats et cetera.

Continuing to refer to FIG. 1, illustrated is data presentation device 106 proximate to light reflecting structure 100. One exemplary implementation of data presentation device 106 proximate to light reflecting structure 100 includes but is not limited to data presentation device 106 integral with light reflecting structure 100. Another exemplary implementation of data presentation device 106 proximate to light reflecting structure 100 includes but is not limited to data presentation device 106 operably coupled with light reflecting structure 100 (e.g., as used herein, proximate may mean operationally proximate—able to work and interact together either directly or through intermediate components—as well as and/or in addition to physically proximate and/or mechanically proximate). Yet another exemplary implementation of data presentation device 106 proximate to light reflecting structure 100 includes but is not limited to data presentation device 106 in physical communication with light reflecting structure 100. One exemplary implementation of data presentation device 106 in physical communication with light reflecting structure 100 includes but is not limited to data presentation device 106 connected with a frame connected with said physical light reflecting structure 100. In some implementations, data presentation device 106 can be a light generation device (e.g., a plasma display and/or a liquid crystal display), an image presentation device (e.g., a direct projection to the eye retinal display), and/or a laser device (e.g., a laser diode device).

Figure 2:
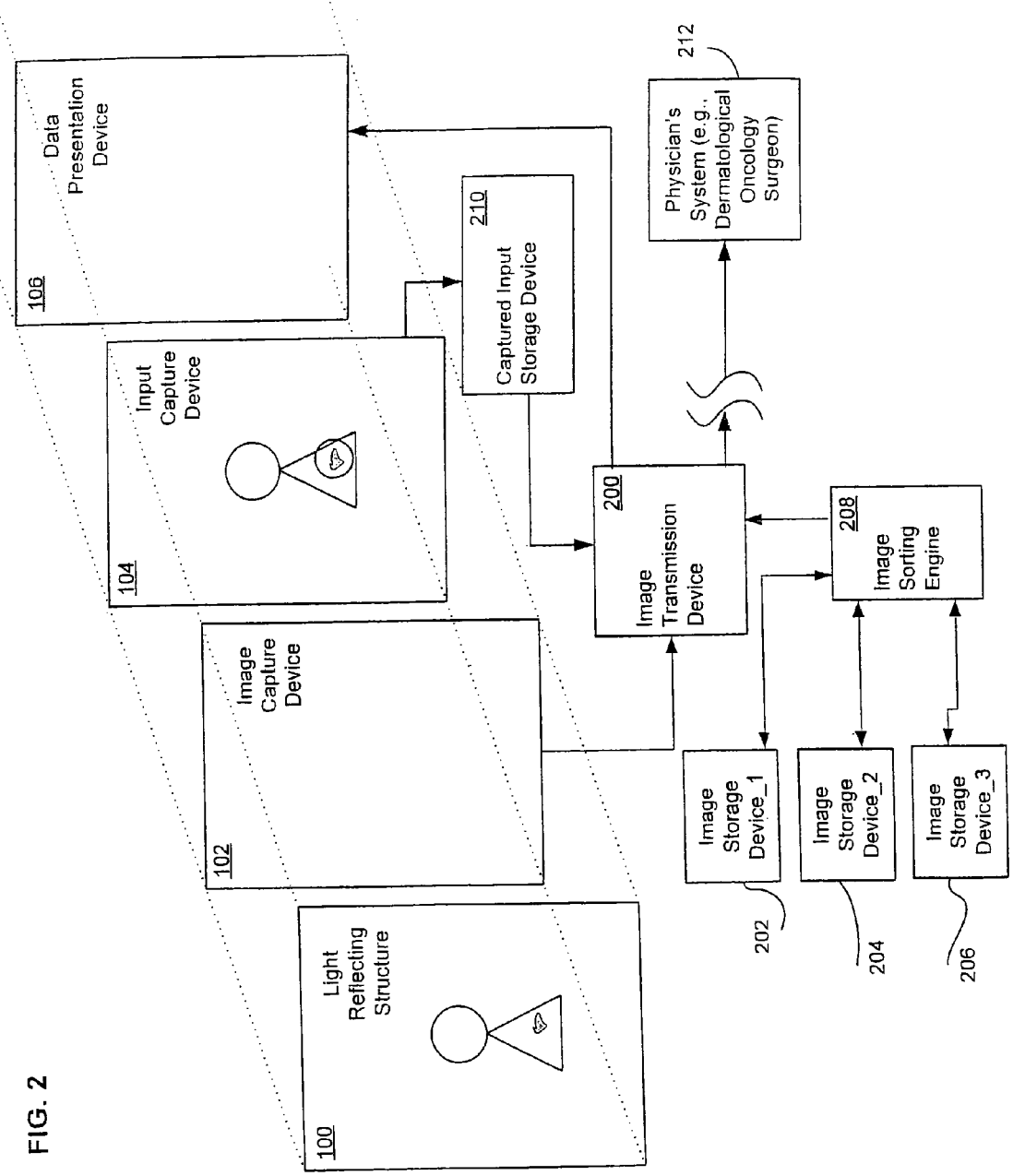
FIG. 2 depicts a partial view of a system that may serve as an illustrative environment of and/or for subject matter technologies.

Referring now to FIG. 2, depicted is a partial view of a system that may serve as an illustrative environment of and/or for subject matter technologies. Illustrated is that image transmission device 200 interfaces with image capture device 102. Shown is that image transmission device 200 interfaces—directly and/or indirectly—with image storage device_1 202, image storage device_2 204, image storage device_3 206, image sorting engine 208, captured input storage device 210, and physician's system 212. In one exemplary implementation, image transmission device 200 receives images from image capture device 102 and/or user input from captured input storage device 210 and/or input capture device 104. For example, as shown in FIG. 2, a user might submit to input capture device 104 that he desires to see medical data associated with an irregularly shaped dark lesion on his upper body. Thereafter, in one implementation, image transmission device 200 transmits one or more captured images and the user selected image regions for which medical overlay data is desired to physician's system 212. While physician's system 212 is described herein for sake of clarity, those skilled in the art will appreciate that physician's system 212 is merely exemplary of the more general case of a medical treatment participant. Examples of such medical treatment participants include but are not limited to persons/robots participating in generating medically-related correlations, medical expert systems, physicians (e.g., psychiatrists/psychologists), nutritionists, pharmacists., personal trainers, drug/chemical testing personnel, nurse practitioners, and/or parents or other people intimately associated with or involved in the medial assessment and diagnostic process (e.g., a parent working under the instructions of a medical caregiver, a delegate of medical professional, a medical treatment participant, someone using medical information (e.g., reading a medical paper), etc.).

In another implementation, image transmission device 200 transmits the one or more images and user selected image regions with respect to which medical data is desired to image sorting engine 208. Image sorting engine 208 thereafter sorts the received images into one or more of image storage device_1 202, image storage device_2 204, and image storage device_3 206 based on pattern recognition algorithms and stores the images in association with the user input. For example, in an implementation where image capture device 102 is capturing three-dimensional (3-D) images of a human subject, image sorting engine 208 may utilize 3-D image processing routines to sort various recognized captured images into image storage device_1 202, image storage device_2 204, and image storage device_3 206 (e.g., where images of a first person are sorted to image storage device_1 202, images of a second person are sorted to image storage device_2 204, and images of a third person are sorted to image storage device_3 206). Those skilled in the art will appreciate that, as used herein, sorting can include categorization, ordering, and/or other operations such as those described herein.

In yet another implementation, image transmission device 200 interacts with image sorting engine 208 to recall images from one or more of image storage device_1 202, image storage device_2 204, and image storage device_3 206 corresponding to an image in light reflecting structure 100. Thereafter, image transmission device 200 causes a display of those other retrieved images through data presentation device 106. Subsequently, a user may select, through the auspices of input capture device 104, one of those other retrieved images. Thereafter, the user may elect to send all or part of the selected images, along with all or part of his current image, to physician's system 212. For example, a user could send earlier images of his body wherein the dark lesion currently exists, along with his current image showing the current state of the lesion, to a dermatological oncologist in order to get an opinion from that oncologist based on a historical progression of the lesion.

Continuing to refer to FIG. 2, in one implementation, image capture device 102 can include at least one image representation device located to capture a field of view of light reflecting structure 100. For example, an active photo-detector array completely and/or partially in identity with a display portion of light reflecting structure 100 or a lensed image capture system oriented such that it can capture all or part of an image reflected from light reflecting structure 100. In another exemplary implementation, image capture device 102 can include at least two image representation devices located to capture a field of view of light reflecting structure 100. For example, two or more camera systems positioned to capture stereo imagery such that 3-D imaging techniques may be applied. The image capture devices described herein can be positioned substantially anywhere an image of light reflecting structure 100 can be captured, such as behind light reflecting structure 100 in order to catch transmitted images through a partially silvered mirror, to the sides and/or above and/or below a mirror, and/or positioned and/or oriented to the front of a mirror in order to record images reflected from a mirror.

Figure 3:
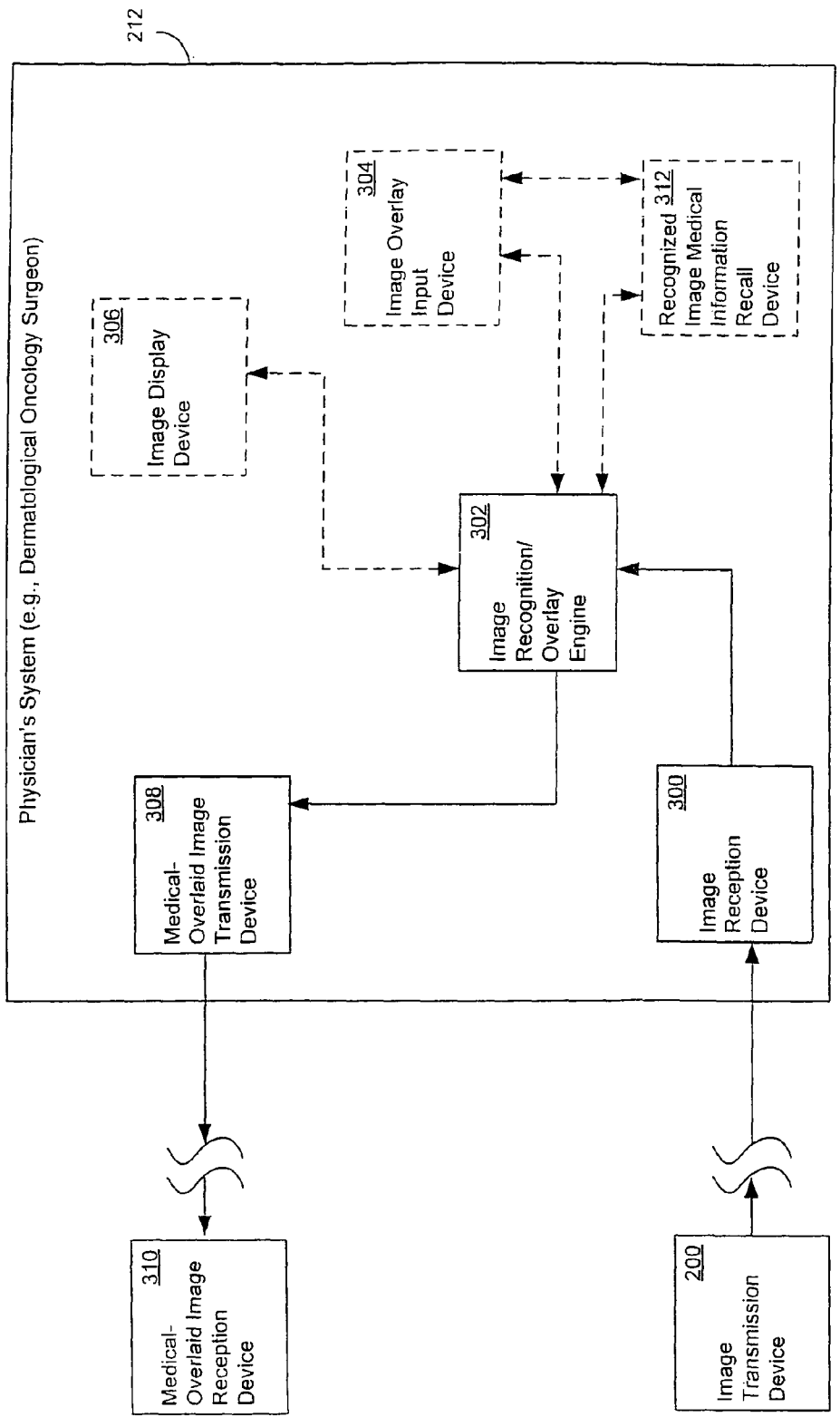
FIG. 3 illustrates a partial view of a system that may serve as an illustrative environment of and/or for subject matter technologies.

With reference now to FIG. 3, illustrated is a partial view of a system that may serve as an illustrative environment of and/or for subject matter technologies. Shown is image transmission device 200 in communication with image reception device 300. Depicted is image reception device 300 interfaced with image recognition/overlay engine 302. Illustrated is image recognition/overlay engine 302 interfaced with image overlay input device 304, image display device 306, and medical-overlaid image transmission device 308. Illustrated is medical-overlaid image transmission device 308 in communication with medical-overlaid image reception device 310.

In one exemplary implementation, image reception device 300 receives one or more images along with any associated user input(s) from image transmission device 200 (e.g., images with an indication that the user desires medical information associated with some portion of his body, face, arms, legs, etc. as such appear in one or more of the images). Thereafter, image reception device 300 transmits the received one or more images and any associated user input indicative of desired medical overlays to image recognition/overlay engine 302. In one implementation, image recognition/overlay engine 302 causes a display of the one or more images and user input indicative of desired medical overlays on image display device 306 (e.g., a high-quality computer monitor).

Image overlay input device 304 accepts input (e.g., from a dermatological oncological surgeon) to overlay medical information onto the image of image display device 306. For instance, in one implementation image overlay input device 304 provides a graphical user interface and cursor driven input to allow a user (e.g., a dermatological oncological surgeon) to overlay the image of image display device 306 in accordance with user input. In response, image recognition/overlay engine 302 creates a medically overlaid version of the displayed image in accord with the input, and displays that medically overlaid image back to the surgeon through image display device 306 (often the medically overlaid image is displayed in tandem with the unmodified image). Thereafter, the surgeon indicates through image overlay input device 304 that the medically overlaid image is acceptable, and in response image recognition/overlay engine 302 causes medical-overlaid image transmission device 308 to transmit the image having the overlaid medical data back to medical-overlaid image reception device 310.

In another implementation, image recognition/overlay engine 302 uses pattern recognition logic to recognize various medical conditions. Thereafter, image recognition/overlay engine 302 transmits one or more images having the recognized medical condition to image overlay input device 304. At about the same time, image recognition/overlay engine 302 transmits the recognized medical condition to recognized image medical information recall device 312 which retrieves medical data in response to the recognized medical condition. Recognized medical information recall device 312 thereafter transmits the medical data to image overlay input device 304, which then overlays the medical data onto the one or more images in a programmed format and thereafter transmits the medically overlaid one or more images back to image recognition/overlay engine 302. Image recognition/overlay engine 302 then transmits the medically overlaid image as described previously.

Figure 4:
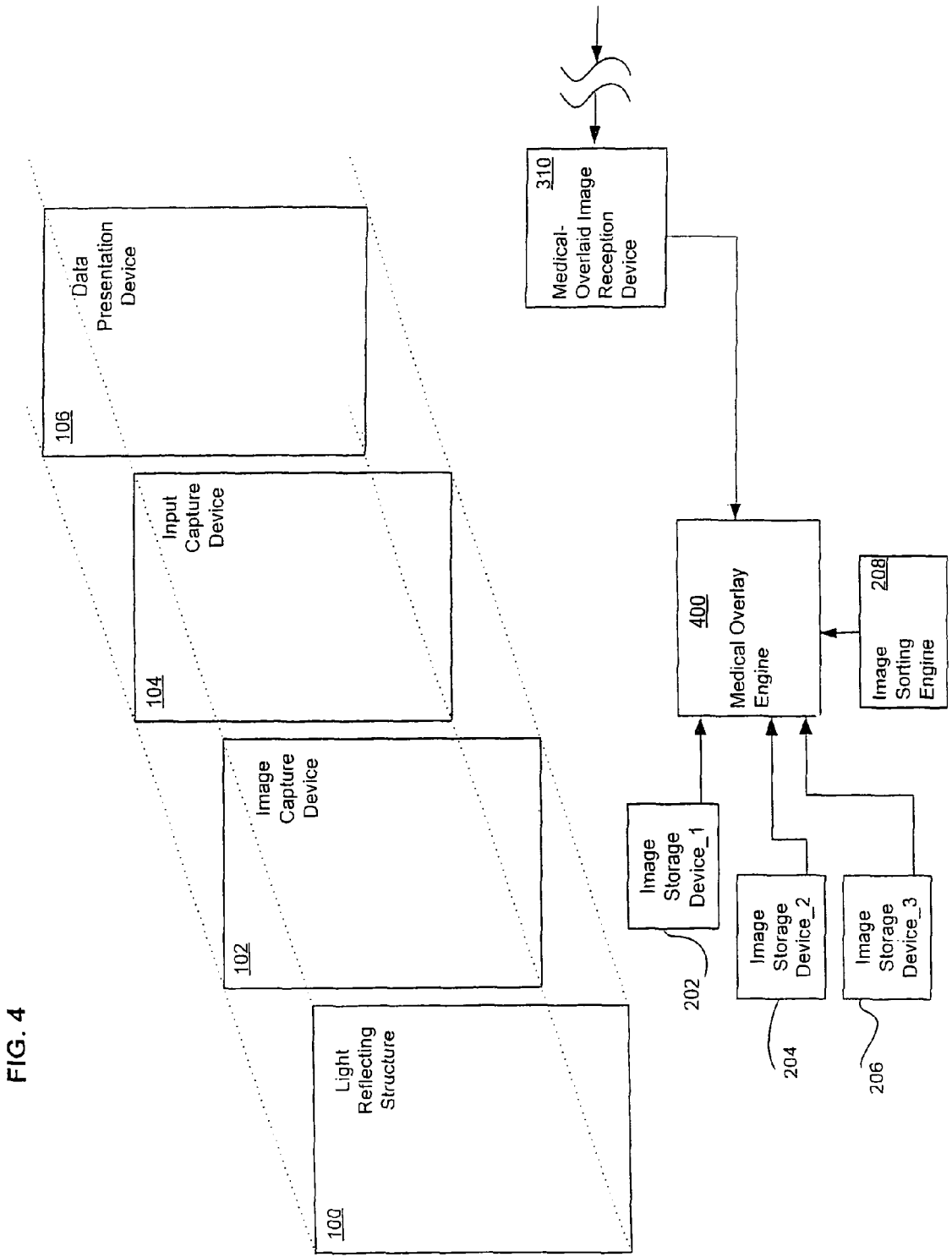
FIG. 4 illustrates a partial view of a system that may serve as an illustrative environment of and/or for subject matter technologies.

Referring now to FIG. 4, illustrated is a partial view of a system that may serve as an illustrative environment of and/or for subject matter technologies. Shown is medical-overlaid image reception device 310 receiving signals (e.g., such as those sent by medical-overlaid image transmission device 308 shown/described in relation to FIG. 3). Medical-overlaid image reception device 310 is shown interfaced with medical overlay engine 400. Medical overlay engine 400 is depicted interfacing with image sorting engine 208, image storage device_1 202, image storage device_2 204, and image storage device_3 206. Although medical overlay engine 400 is described in the context of overlaying physician and/or expert system generated overlay data, those having skill in the art will appreciate that medical data from other sources may also be overlaid, such as data from a bathroom scale, a diagnostic toilet, a blood pressure monitor, a diagnostic blood kit, etc., which are operably couplable with medical overlay engine 400. Other examples of medical data that may be overlaied can include but are not limited to current diagnostic readings (e.g., blood pressure, heartrate, blood sugar level, height, weight, cholesterol, etc.), historical diagnostic readings (average resting heart rate over time, average fasting blood sugar, trends in readings, etc.), automatic warnings about diagnostics (e.g., low blood sugar, high blood sugar, other protein analysis from urine, etc.), medication reminders such as including an ability to mark medication as taken and/or see historical compliances (e.g., flossed 30% of days in last month, took BP medication every day last week), medical reminders about injury rehabilitation (e.g., 10 leg lifts today for injured knee), workout program suggestions (e.g., pecs look good, do more triceps work), etc. In addition, in some implementations, medical overlay engine 400 includes a notification sub-engine (not shown) that provides for information can be pulled from an overlaying source as well as information being pushed from an overlaying source.

In one implementation, medical overlay engine 400 receives one or more images with medical overlays from medical overlaid image reception device 310. In another implementation, in order to save time/bandwidth, medical-overlay engine 400 receives instructions as to how to modify the one or more images (e.g., by overlaying medical data onto the images), and medical-overlay engine 400 thereafter interacts with image sorting engine 208, image storage device_1 202, image storage device_2 204, and image storage device_3 206 to actually generate the medically-overlaid one or more images locally.

Figure 5:
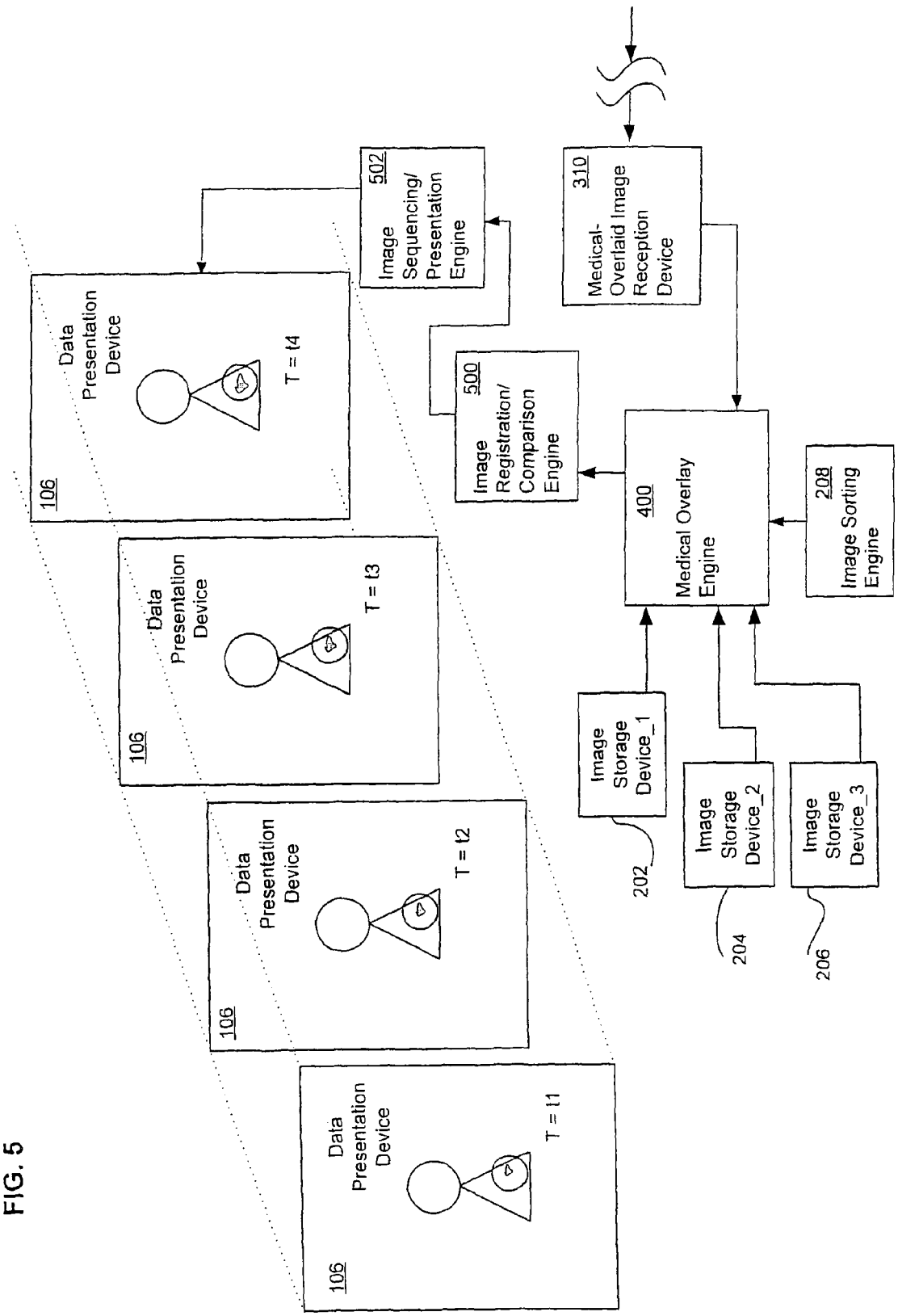
FIG. 5 shows a partial view of a system that may serve as an illustrative environment of and/or for subject matter technologies.

With reference now to FIG. 5, shown is a partial view of a system that may serve as an illustrative environment of and/or for subject matter technologies. Depicted is medical-overlay engine 400 interfaced with image registration/comparison engine 500. Shown is image registration/comparison engine 500 interfaced with image sequencing/presentation engine 502. In one exemplary implementation, medical-overlay engine 400~in concert with image sorting engine 208~retrieves one or more images from one or more of image storage device_1 202, image storage device_2 204, and image storage device_3 206. Subsequently, medical overlay engine 400 overlays medical data onto the one or more retrieved images in accord with received overlay instructions (e.g., such as those received from physician's system 212 as described herein). Thereafter, image registration/comparison engine 500 uses some relatively stable image feature(s), such as anatomical landmarks (e.g., bony regions or a center part of some defined anatomical feature, to encompass and or localize a region of interest where some feature of interest resides), to provide proper alignment amongst images and/or medical overlay data. In another implementation, medical overlay engine 400 receives images that have already been medically-overlaid by image recognition/overlay engine 302 of physician's system 212. Irrespective of whether the medically overlaid images are generated locally or received in already enhanced/modified form, in one implementation image sequencing/presentation engine 502 then presents the aligned images in a sequenced fashion such that the medically overlaid information produced responsive to the user input can be viewed. For instance, image sequencing/presentation engine 502 might present a sequenced presentation of various medical opinion/narratives with respect to various images of a skin lesion over time as supplied by a dermatological oncologist as described herein. In another implementation, image sequencing/presentation engine 502 presents a non-sequential menu of options, some which either entail and/or are related to various alternate proposed medical overlays from the dermatological oncologist.

Figure 6:
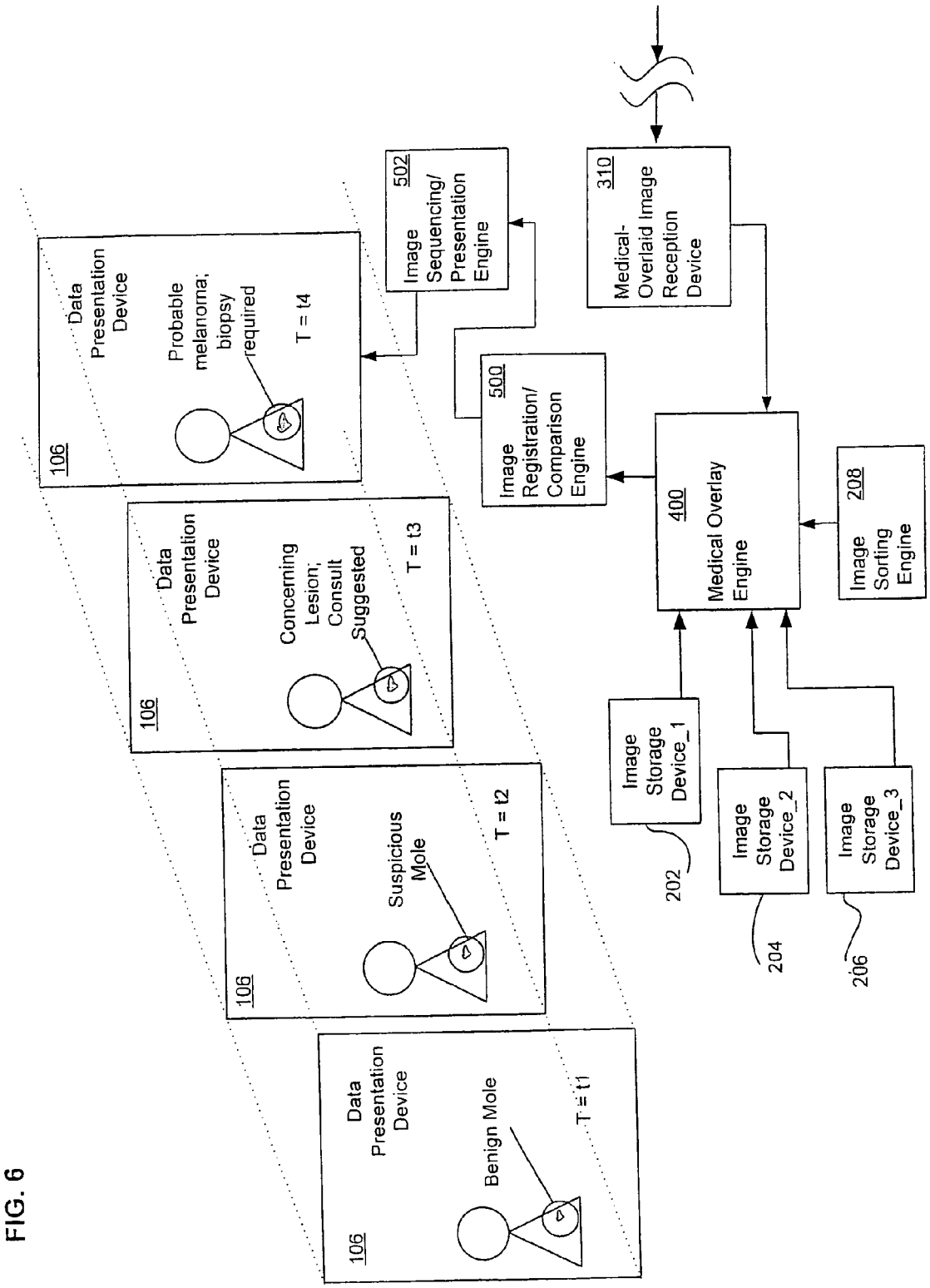
FIG. 6 depicts a partial view of a system that may serve as an illustrative environment of and/or for subject matter technologies

Referring now to FIG. 6, depicted is a partial view of a system that may serve as an illustrative environment of and/or for subject matter technologies. Illustrated is the system presenting four sequenced images showing various proposed medical overlays to a user's captured image. For instance, depicted at sequence time T=t1 is a presentation of an oldest image entered by the user/retrieved by the system as well as text indicative of a medical overlay. Specifically, shown is that the earliest image having a small irregularly shaped lesion has associated with it a medical overlay giving a doctor's opinion that the area of concern appears most like a benign mole (alternatively, in another contemplated implementation the medical opinion overlay is obtained from an electronic medical database searched with pattern recognition software). Like medical overlays to the user image are shown at sequence times T=t2 through T=t4. At sequence times T=t2 through T=t4, shown are various medical overlays onto the user's image in accord with the instructions of a dermatological oncologist such as described elsewhere herein. Depicted in FIG. 6 are exemplary overlays showing that the physician's opinion of the region over time is that the region has progressed from an apparent benign mole stage (T=t1), to a suspicious mole stage (T=t2), to a concerning skin lesion (T=t3), and ultimately to what superficially appears to be a probable melanoma (T=t4). Further shown in medical overlay are suggested courses of action to the patient (e.g., consult physician; obtain biopsy).

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Referring now to FIG. 7, illustrated is a high-level logic flowchart of a process. Method step 700 shows the start of the process. Method step 702 shows accepting input related to at least a part of an image of a light reflecting structure (e.g., via input capture device 104 and/or captured input storage device 210 and/or a supporting component(s) accepting input when a user has indicated one or more portions of an image in light reflecting structure 100). Method step 704 depicts presenting one or more medically-overlaid images related to at least a part of the image of the light reflecting structure (e.g., such as shown/described in relation to FIG. 6). Method step 706 shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view of a mirror. For example, in a hand-held mirror implementation, a user might zoom in on a region of an image and then ask to see a medically overlaid time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the un-zoomed field of view, in some implementations the use of anchor points will allow coordination between the zoomed and unzoomed views. In addition, the inventors further point out that while examples set forth herein focus on anatomy and/or anatomical change for sake of clarity, the systems described herein can actually track and/or show a medically-overlaid time lapse of substantially any object that may be reflected in the mirror.

Figure 7A:
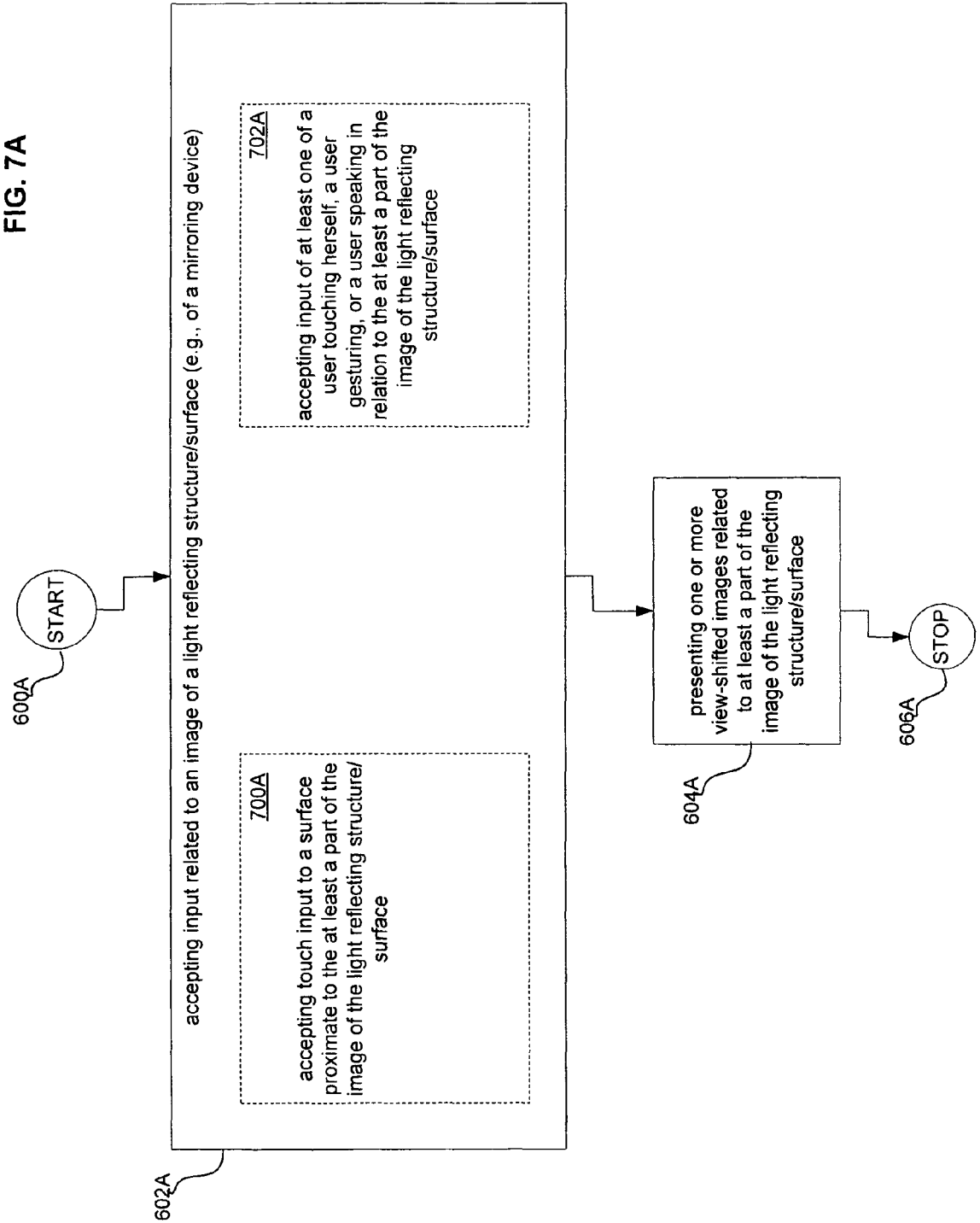
FIG. 7A shows a high-level logic flowchart depicting alternate implementations of the high-level logic flowchart of FIG. 6A.
Figure 8:
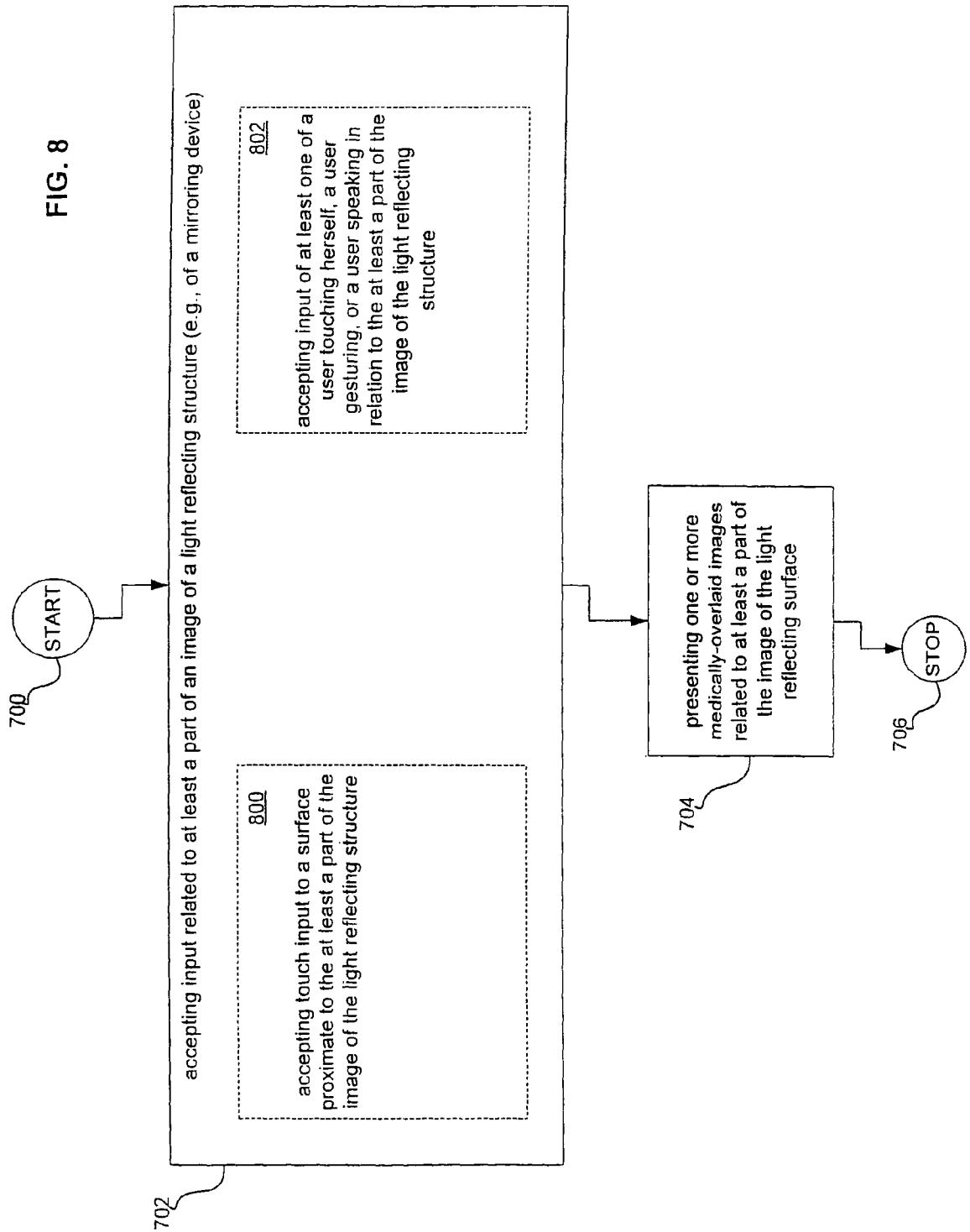
FIG. 8 shows a high-level logic flowchart depicting alternate implementations of the high-level logic flowchart of FIG. 7.

With reference now to FIG. 8, shown is a high-level logic flowchart depicting alternate implementations of the high-level logic flowchart of FIG. 7. Depicted is that in various alternate implementations, method step 702 includes method step 800 and/or method step 802. Method step 800 shows accepting touch input to a surface proximate to the at least a part of the image of the light reflecting structure (e.g., via input capture device 104 and/or captured input storage device 210 capturing input when a user has indicated one or more portions of an image in light reflecting structure 100). Method step 802 depicts accepting input of at least one of a user touching herself, a user gesturing, or a user speaking in relation to the at least a part of the image of the light reflecting structure For example, via input capture device 104 capturing input when a user's gestures or pointing relative to at least a part of an image in light reflecting structure 100 and/or the user speaking a command in relation to at least a part of an image in light reflecting structure 100. Specific examples of the foregoing would include a user leaning a body part toward light reflecting structures 100 and/or a user moving a body part into a field of view of light reflecting structure 100 (or vice versa), such as an input of moving a hand-held mirror over a location where the action of the movement itself coupled with the content of the image captured constitutes an input with respect to the image (e.g., a feature recognized in the image could constitute all or part of the input).

Referring now to FIG. 9, depicted is a high-level logic flowchart depicting alternate implementations of the high-level logic flowchart of FIG. 8. Depicted is that in one alternate implementation, method step 800 includes method step 900 and/or method step 902. Method step 900 shows detecting input to a touch sensitive device associated with the light reflecting structure (e.g. via light reflecting structure 100 and/or input capture device 104 and/or captured input storage device 210 and/or one or more of their supporting components). Method step 902 depicts detecting input to a mouse associated with the light reflecting structure (e.g. via light reflecting structure 100 and/or input capture device 104 and/or captured input storage device 210 and/or one or more of their supporting components).

With reference now to FIG. 10, illustrated is a high-level logic flowchart depicting alternate implementations of the high-level logic flowchart of FIG. 7. Depicted is that in various alternate implementations, method step 704 includes method step 1000, and/or method steps 1002-1006. Method step 1000 shows one alternate implementation of obtaining one or more images having the at least a part of the image of the light reflecting structure. For example, obtaining the one or more images via image recognition/overlay engine 302, medical overlay engine 400, image sorting engine 208, and/or one or more of image storage devices 202-206.

Continuing to refer to FIG. 10, method steps 1002-1006 depict another alternate embodiment. Method step 1002 illustrates identifying one or more landmarks demarcating the at least a part of the image of the light reflecting structure (e.g., via image sorting engine 208 and/or image registration/comparison engine 500). Example of such landmarks include anatomical landmarks such as those described elsewhere herein and/or behavioral landmarks such as those associated with certain conditions such as physical and/or mental illness (e.g., facial expressions, skin tones, body positions/postures, etc.). Method step 1004 shows medically overlaying at least a part of the one or more images having the one or more landmarks (e.g., via image recognition/overlay engine 302 and/or medical overlay engine 400). Method step 1006 depicts presenting one or more medically overlaid versions of the one or more images having the one or more landmarks (e.g., via data presentation device 106 and/or medical overlay engine 400).

Referring now to FIG. 11, shown is a high-level logic flowchart depicting alternate implementations of the high-level logic flowchart of FIG. 10. Depicted is that in various alternate implementations, method step 1006 includes method step 1100 and/or method step 1102. Method step 1100 illustrates registering at least a portion of the one or more medically overlaid versions of the one or more images having the one or more landmarks with the image of the light reflecting structure (e.g., via image registration/comparison engine 500). Method step 1102 shows at least one of sequencing or presenting at least a portion of the one or more medically overlaid versions of the one or more images having the one or more landmarks (e.g., via image sequencing/presentation engine 502).

Referring now to FIG. 12, illustrated is a high-level logic flowchart depicting several alternate implementations of the high-level logic flowchart of FIG. 10. Shown is that in one alternate implementation, method step 1004 includes method step 1200. Method step 1200 shows medically overlaying a specified feature having a state (e.g., via input capture device 102 and/or image recognition/overlay engine 302 and/or medical overlay engine 400 and/or their supporting components). Further shown is that in one alternate embodiment method stop 1200 can include method step 1202 which depicts medically overlaying at least one skin feature (e.g., placing text showing a medical opinion in proximity to a skin lesion, should a user have indicated that the skin region was of interest). Further shown is that in yet another alternate embodiment method stop 1200 can include method step 1204 which illustrates medically overlaying at least one body region (e.g., placing medical encyclopedia text/pictures in proximity to a rash on a person's torso, should the person have entered input indicating that the torso rash was of interest).

Those having skill in the art will appreciate that in some instances, the devices described herein can be networked. For example, having two or more of the mirroring devices described herein within a house that share their data between each other and/or having portable mirrors for use when traveling that can access data from mirrors in ones house. In addition, in other contemplated implementations the mirroring devices include notification sub-engines as described here and elsewhere that ensure that information can be pulled and/or pushed).

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

All of the above U.S. patents, U.S. patent application publications, U.S. patent applications, foreign patents, foreign patent applications and non-patent publications referred to in this specification and/or listed in any Application Data Sheet are incorporated herein by reference, in their entireties.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of one having skill in the art would understand the convention (e.g., " a system having at least one of A, B, or C" would include but not be limited to systems that have A alone, B alone, C alone, A and B together, A and C together, B and C together, and/or A, B, and C together, etc.).

II. Multi-Angle Mirror

With reference to the figures, and with reference now to FIG. 1A, shown is a partial view of a system that may serve as an illustrative environment of and/or for subject matter technologies. Depicted are zero degree view mirror 100A, zero degree image capture device 102A, input capture device 104A, data presentation device 106A, one-hundred-eighty degree view mirror 108A, and one-hundred eighty degree view image capture device 110A. In one exemplary implementation, zero degree view mirror 100A and/or one-hundred-eighty degree view mirror 108A can be a plane mirror, a convex mirror, and/or a concave mirror (the same is generally true for substantially any mirroring device described herein, unless context dictates otherwise). In another exemplary implementation, one or more of the mirrors described herein can be partially silvered mirrors. In some exemplary implementations, one or more of the mirrors described herein can be physical mirrors. In other exemplary implementations, one or more of the mirrors described herein can be digital mirrors and/or projection mirrors. In yet other implementations, one or more of the mirrors described herein can be combinations of one or more physical mirrors and/or one or more digital mirrors and/or one or more projection mirrors. In some implementations, data presentation device 106A may present various types of multi-angle view information (e.g., either simultaneous and/or sequential images of a person as viewed from the front, side, back, etc.) in addition to or in the alternative of time-lapse information, image information, height and/or weight information. In some implementations, presentations of information may be in the form of various modalities including but not limited to graphs, tables, audio (speech, music, sound), text, store-and-forward formats (e.g., email, voicemail, and/or simple message system mail at various reporting intervals, such as in a weekly digest format), et cetera.

Continuing to refer to FIG. 1A, illustrated is data presentation device 106A proximate to zero degree view mirror 100A. One exemplary implementation of data presentation device 106A proximate to zero degree view mirror 100A includes but is not limited to data presentation device 106A integral with zero degree view mirror 100A; other exemplary implementations include but are not limited to like data presentation devices integral with virtually any one or more mirrors described herein (e.g., one or more mirrors respectively associated with one or more image capture devices 102A, 110A, 300A, 304A, 308A, 312A, 316A, and/or 320A as described in relation to FIG. 3A). Another exemplary implementation of data presentation device 106A proximate to zero degree view mirror 100A includes but is not limited to data presentation device 106A operably coupled with zero degree view mirror 100A (e.g., as used herein, proximate may mean operationally proximate—able to work and interact together either directly or through intermediate components—as well as and/or in addition to physically proximate and/or mechanically proximate, such as overlapping and/or integrated with); other exemplary implementations include but are not limited to like data presentation devices operably coupled with virtually any one or more mirrors described herein (e.g., one or more mirrors respectively associated with one or more image capture devices 102A, 110A, 300A, 304A, 308A, 312A, 316A, and/or 320A as described in relation to FIG. 3A). Yet another exemplary implementation of data presentation device 106A proximate to zero degree view mirror 100A includes but is not limited to data presentation device 106A in physical communication with zero degree view mirror 100A; other exemplary implementations include but are not limited to like data presentation devices integral with virtually any one or more mirrors described herein (e.g., mirrors 102A, 110A, 300A, 304A, 308A, 312A, 316A, and/or 320A as described in relation to FIG. 3A). One exemplary implementation of data presentation device 106A in physical communication with zero degree view mirror 100A includes but is not limited to data presentation device 106A connected with a frame connected with said physical zero degree view mirror 100A; other exemplary implementations include but are not limited to like data presentation devices connected with a frame connected with virtually any one or more mirrors described herein (e.g., mirrors 102A, 110A, 300A, 304A, 308A, 312A, 316A, and/or 320A as described in relation to FIG. 3A). In some implementations, one or more data presentation devices such as those described herein can be light generation devices (e.g., plasma displays and/or liquid crystal displays), image presentation devices (e.g., direct projection to the eye retinal displays), and/or laser devices (e.g., laser diode devices).

Figure 2A:
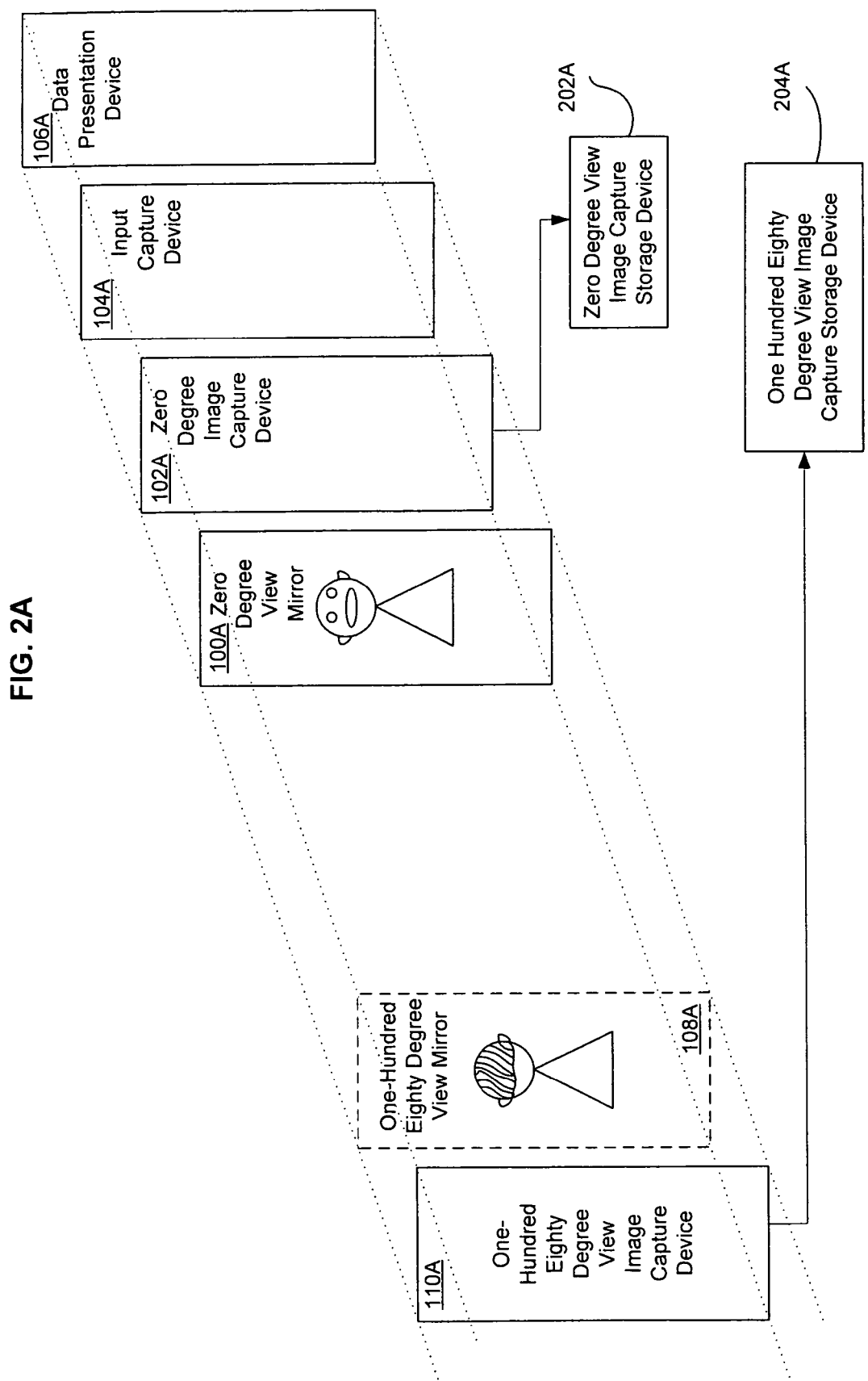
FIG. 2A depicts a partial view of a system that may serve as an illustrative environment of and/or for subject matter technologies.

Referring now to FIG. 2A, depicted is a partial view of a system that may serve as an illustrative environment of and/or for subject matter technologies. Illustrated is that zero degree view image capture storage device 202A interfaces with zero degree image capture device 102A. Shown is that one-hundred eighty degree view image capture storage device 204A interfaces with one-hundred eighty degree view image capture device 110A. Depicted is that, in one exemplary implementation, zero degree view image capture storage device 202A receives images of a person's face and frontal torso from zero degree image capture device 102A while one-hundred eighty degree view image capture storage device 204A receives images of the back of the person's head and rear torso from one-hundred eighty degree view image capture device 110A. For example, in one implementation technologies described herein will let a person see how she/he appears from front, back, sides, diagonally, etc. Those having skill in the art will appreciate that the presentation of images, as described herein, have not called out an orientation of presented views for sake of clarity. Accordingly, those skilled in the art will appreciate that the presentations described herein could be indicative of standard mirror views (e.g., reversed left to right) and/or non-standard mirror views (e.g., non-reversed views).

Figure 3A:
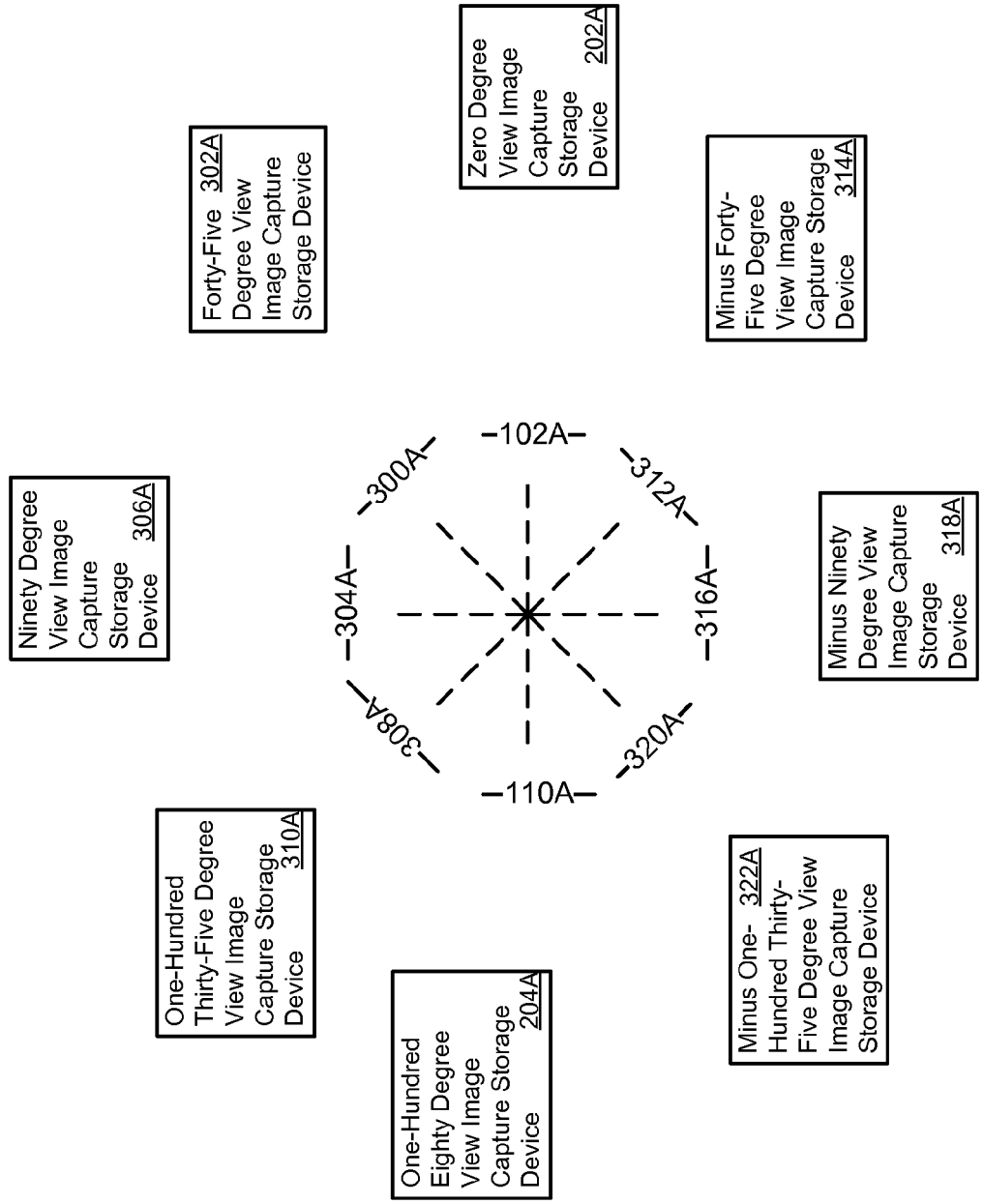
FIG. 3A illustrates a partial view of a system that may serve as an illustrative environment of and/or for subject matter technologies.

With reference now to FIG. 3A, illustrated is a partial view of a system that may serve as an illustrative environment of and/or for subject matter technologies. Shown are zero degree image capture device 102A, forty-five degree image capture device 300A, ninety-degree view image capture device 304A, one-hundred-thirty-five degree view image capture device 308A, minus-forty-five degree image capture device 312A, minus-ninety-degree image capture device 316A, and minus-one-hundred-thirty-five degree view image capture device 320A respectively coupled with zero degree view image capture storage device 202A, forty-five degree view image capture storage device 302A, ninety-degree view image capture storage device 306A, one-hundred-thirty-five degree view image capture storage device 310A, minus-forty-five degree view image capture storage device 314A, minus-ninety-degree view image capture storage device 318A, and minus-one-hundred-thirty-five degree view image capture storage device 322A. In some implementations, one or more of the herein-described image capture devices have respectively associated mirrors, where such association is analogous to one or more associations described in relation to FIGS. 1A and/or 2A and or elsewhere herein (e.g., a proximate association and/or an operable association and/or a physical association and/or an integral association). In some implementations, some of the mirrors described herein may be hand mirrors. In addition, those skilled in the art will recognize that the angles described herein are indicative of angles within substantially any appropriate coordinate system such as planar, spherical, cylindrical, etc.

Those skilled in the art will appreciate that in some implementations one or more of the image capture devices described herein entail image representation capture devices, where the capturing and/or representing of information can entail capture and/or representation in a way that is qualitatively different from that normally associated with what a human sees when s/he views a physical mirror—e.g. infrared or UV or some like kind of detection. In addition to the foregoing, those skilled in the art will appreciate that the presentations of images such as described herein can likewise entail such qualitatively different representations, or other representational information drawn on such qualitatively different representations. In addition to the foregoing, in some implementations, image representation capture may include an indication of a direction and/or field of view of an image capture device and/or a light reflecting surface/structure associated therewith (e.g., an outline on a presented image of what a capturing mirror "sees").

Figure 4A:
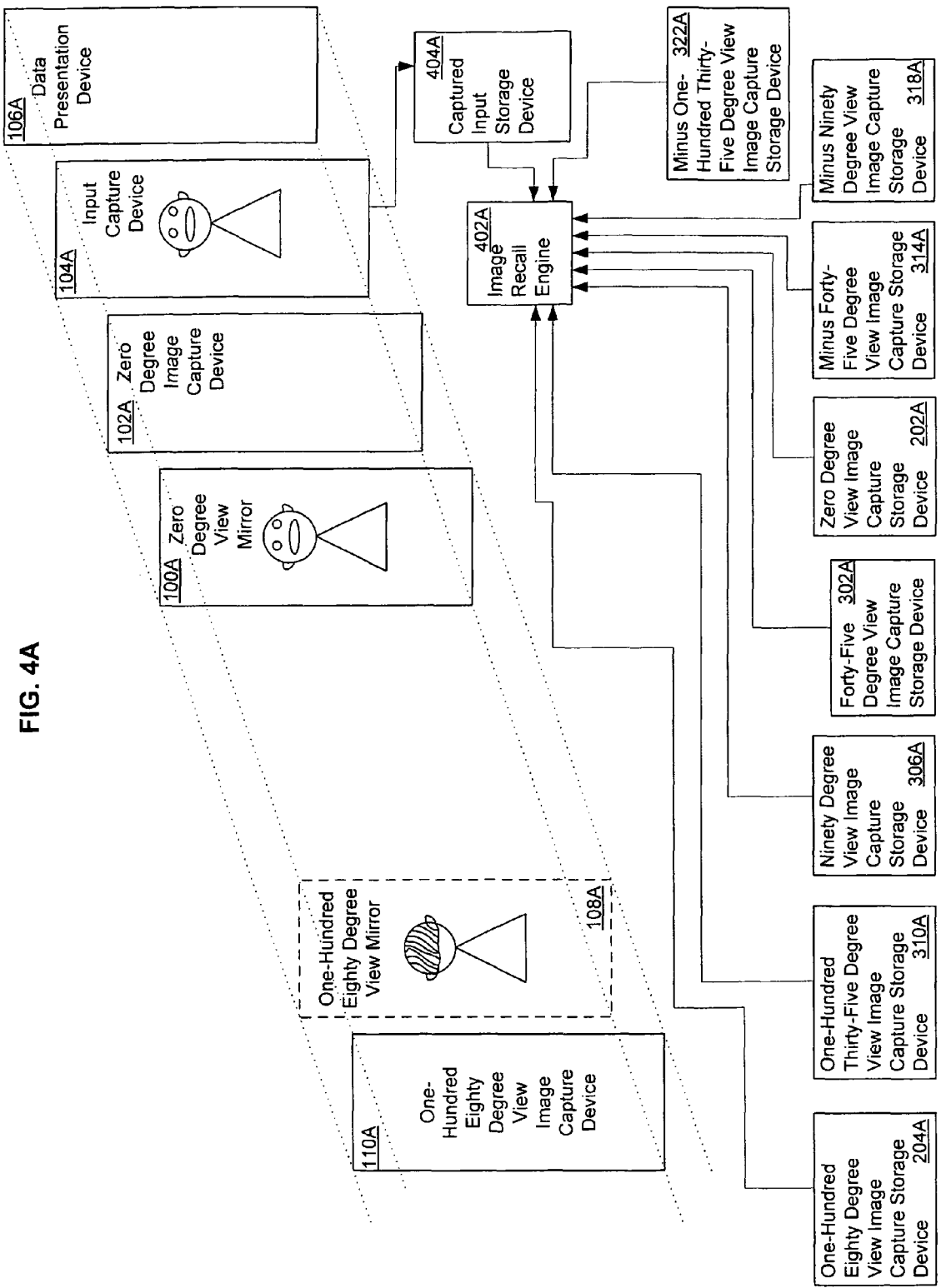
FIG. 4A illustrates a partial view of a system that may serve as an illustrative environment of and/or for subject matter technologies.

Referring now to FIG. 4A, illustrated is a partial view of a system that may serve as an illustrative environment of and/or for subject matter technologies. Shown is image recall engine 402A receiving signals (e.g., such as those sent by modified image transmission device 308A shown/described in FIG. 3A). Image recall engine 402A is shown interfaced with zero degree view image capture storage device 202A, forty-five degree view image capture storage device 302A, ninety-degree view image capture storage device 306A, one-hundred-thirty-five degree view image capture storage device 310A, minus-forty-five degree view image capture storage device 314A, minus-ninety-degree view image capture storage device 318A, and minus-one-hundred-thirty-five degree view image capture storage device 322A. Image recall engine 402A is depicted interfaced with captured input storage device 404A.

In one exemplary implementation, captured input storage device 404A receives one or more images along with any associated user input(s) from input capture device 104A (e.g., images with an indication that the user desires that different angled views (e.g., front/back/side views of his body/face/hairline/etc.) be presented). Thereafter, captured input storage device 404A transmits the received one or more images and any associated user input indicative of desired views to image recall engine 402A. In one implementation, image recall engine 402A causes a display of the one or more multi-angle view images in response to the user input requested multiple views through data presentation device 106A.

Figure 5A:
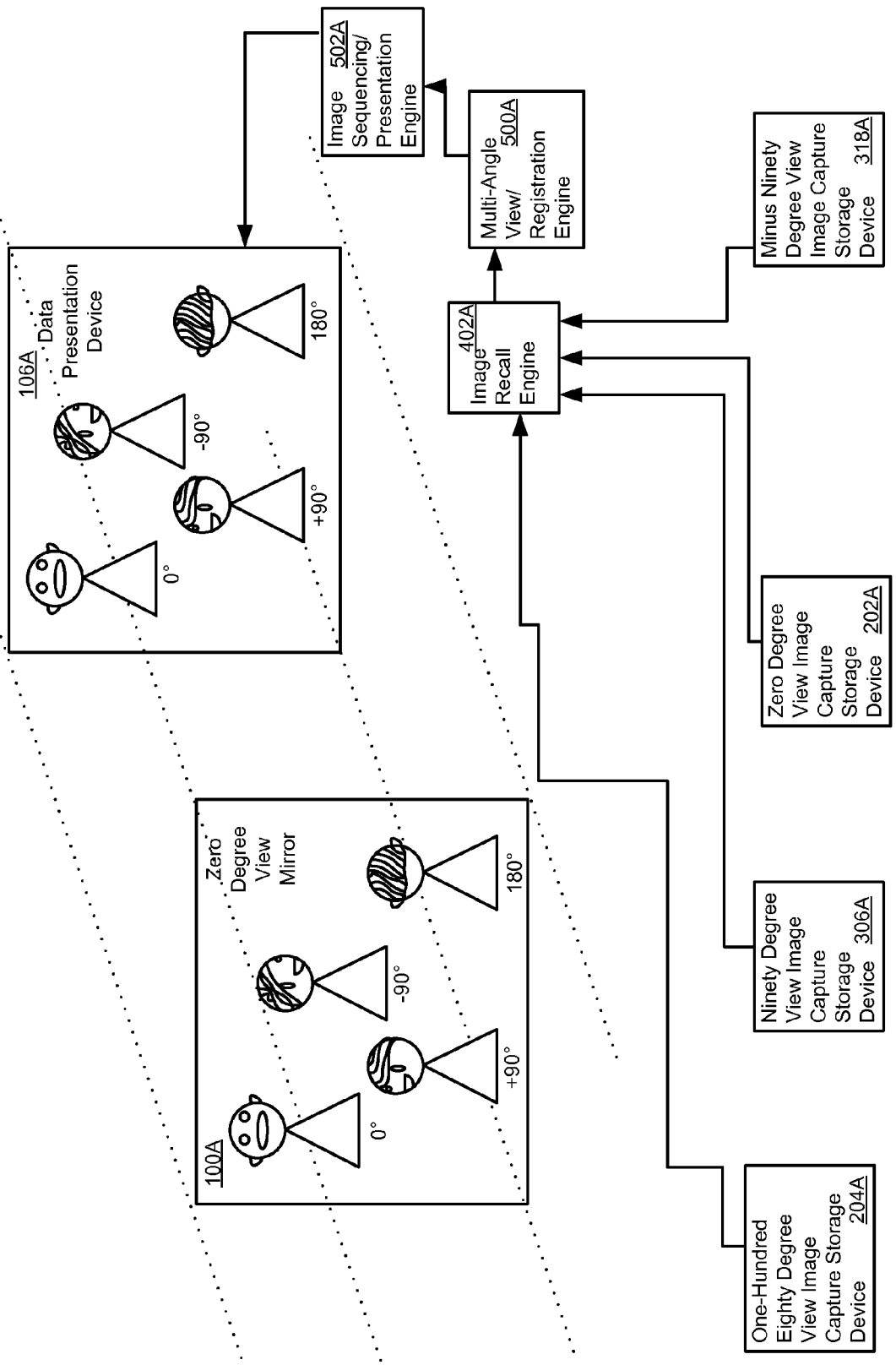
FIG. 5A shows a partial view of a system that may serve as an illustrative environment of and/or for subject matter technologies.

With reference now to FIG. 5A, shown is a partial view of a system that may serve as an illustrative environment of and/or for subject matter technologies. Depicted is multi-angle view/registration engine 500A interfaced with image sequencing/presentation engine 502A. In one exemplary implementation, image recall engine 402A—typically in response to user input specifying one or more desired multi-angle views—retrieves one or more images from one or more of zero degree view image capture storage device 202A, forty-five degree view image capture storage device 302A, ninety-degree view image capture storage device 306A, one-hundred-thirty-five degree view image capture storage device 310A, minus-forty-five degree view image capture storage device 314A, minus-ninety-degree view image capture storage device 318A, and minus-one-hundred-thirty-five degree view image capture storage device 322A. Subsequently, multi-angle view/registration engine 500A constructs one or more partial frames having views as specified by the user input. Thereafter, in one implementation image sequencing/presentation engine 502A then presents the various multi-angle views in such a fashion that the views specified by the user input can be viewed. For instance, image sequencing/presentation engine 502A might present a freeze-frame presentation of various captured views. For example, views such as those captured by the image captured devices described in relation to FIG. 3A, where the zero degree view is understood to be that associated with the person looking directly into the mirror. Specifically, shown in FIG. 5A are exemplary representations of data presentation device 106A presenting views of a person through zero degree view mirror 100A; the views shown are illustrated as having been captured from zero degree view image capture storage device 202A, forty-five degree view image capture storage device 302A, one-hundred-thirty-five degree view image capture storage device 310A, and minus-forty-five degree view image capture storage device 314A, where the person is illustrated as having had her views captured while looking face-on into zero angle view mirror 100A.

While the foregoing has described presentations of various multi-angle views of more-or-less static images those skilled in the art will appreciate that the teachings herein may be combined with the teachings of the above referenced technologies and incorporated by reference time-lapsing mirror technologies such that the various multi-angle views presented may be time lapsed images. The combination of the present teachings and the teachings of the time-lapsing mirror technologies are within the ambit of one having skill in the art in light of the teachings herein (e.g., the as-filed claims), and hence are not expressly recited here for sake of clarity.

While the foregoing has described presentations of various multi-angle views of more-or-less static images as well as presentations of more-or-less time-lapsed images, those skilled in the art will appreciate that the teachings herein may be combined with the teachings of the above-referenced technologies and incorporated by reference cosmetic-enhancement mirror technologies such that the various multi-angle views presented may be either static and/or time lapsed images of cosmetically enhanced subjects. The combination of the present teachings and the teachings of the cosmetic enhancement mirror technologies are within the ambit of one having skill in the art in light of the teachings herein (e.g., the as-filed claims), and hence are not expressly recited here for sake of clarity.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 6A:
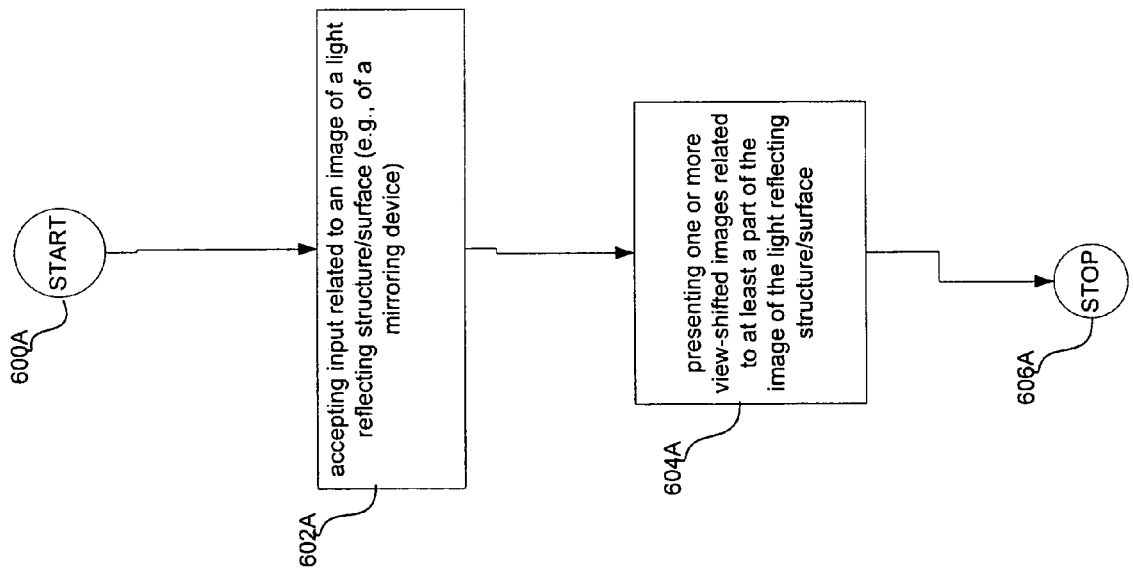
FIG. 6A illustrates a high-level logic flowchart of a process.

Referring now to FIG. 6A, illustrated is a high-level logic flowchart of a process. Method step 600A shows the start of the process. Method step 602A shows accepting input related to an image of a light reflecting structure/surface (e.g., of a mirroring device) (e.g., via input capture device 104A and/or a supporting component(s) accepting input when a user has indicated one or more portions of an image in zero degree view mirror 100A). Method step 604A depicts presenting one or more view-shifted images related to at least a part of the image of the light reflecting structure/surface (e.g., such as shown/described in relation to FIG. 5A and/or elsewhere herein). Method step 606A shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view of a mirror. For example, in a hand-held mirror implementation, a user might zoom in on a region of an image and then ask to see a time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the un-zoomed field of view, in some implementations the use of anchor points will allow coordination between the zoomed and unzoomed views. In addition, the inventors further point out that while examples set forth herein focus on anatomy and/or anatomical change for sake of clarity, the systems described herein can actually track and/or show a time lapse of substantially any object that may be reflected in the mirror.

With reference now to FIG. 7A, shown is a high-level logic flowchart depicting alternate implementations of the high-level logic flowchart of FIG. 6A. Depicted is that in various alternate implementations, method step 602A includes method step 700A and/or method step 702A. Method step 700A shows accepting touch input to a surface proximate to the at least a part of the image of the light reflecting structure/surface (e.g., via input capture device 104A and/or captured input storage device 404A capturing input when a user has indicated a desire to see one or more alternate angle views instead of and/or in addition to an image in zero degree view mirror 100A) Method step 702A depicts accepting input of at least one of a user touching herself, a user gesturing, or a user speaking in relation to the at least a part of the image of the light reflecting structure/surface (e.g., via input capture device 104A capturing input when a user's gestures or pointing relative to at least a part of an image in zero degree view mirror 100A and/or the user speaking a command in relation to at least a part of an image in zero degree view mirror 100A that the user wishes to see one of a multi-angle view of the image in zero degree view mirror 100A). As an aside, the inventors point out that there are various different implementations of the light reflecting surface/structure as described herein, such as bathroom, hall, foyer, refrigerator, living room, etc. mounted/located mirrors.

Referring now to FIG. 8A, depicted is a high-level logic flowchart depicting alternate implementations of the high-level logic flowchart of FIG. 7A. Depicted is that in one alternate implementation, method step 700A includes method step 800A and/or method step 802A. Method step 800A shows detecting input to a touch sensitive device associated with the light reflecting structure/surface (e.g. via zero degree view mirror 100A and/or input capture device 104A and/or one or more of their supporting components). Method step 802A depicts detecting input to a mouse associated with the light reflecting structure/surface (e.g. via zero degree view mirror 100A and/or input capture device 104A and/or one or more of their supporting components).

Figure 9A:
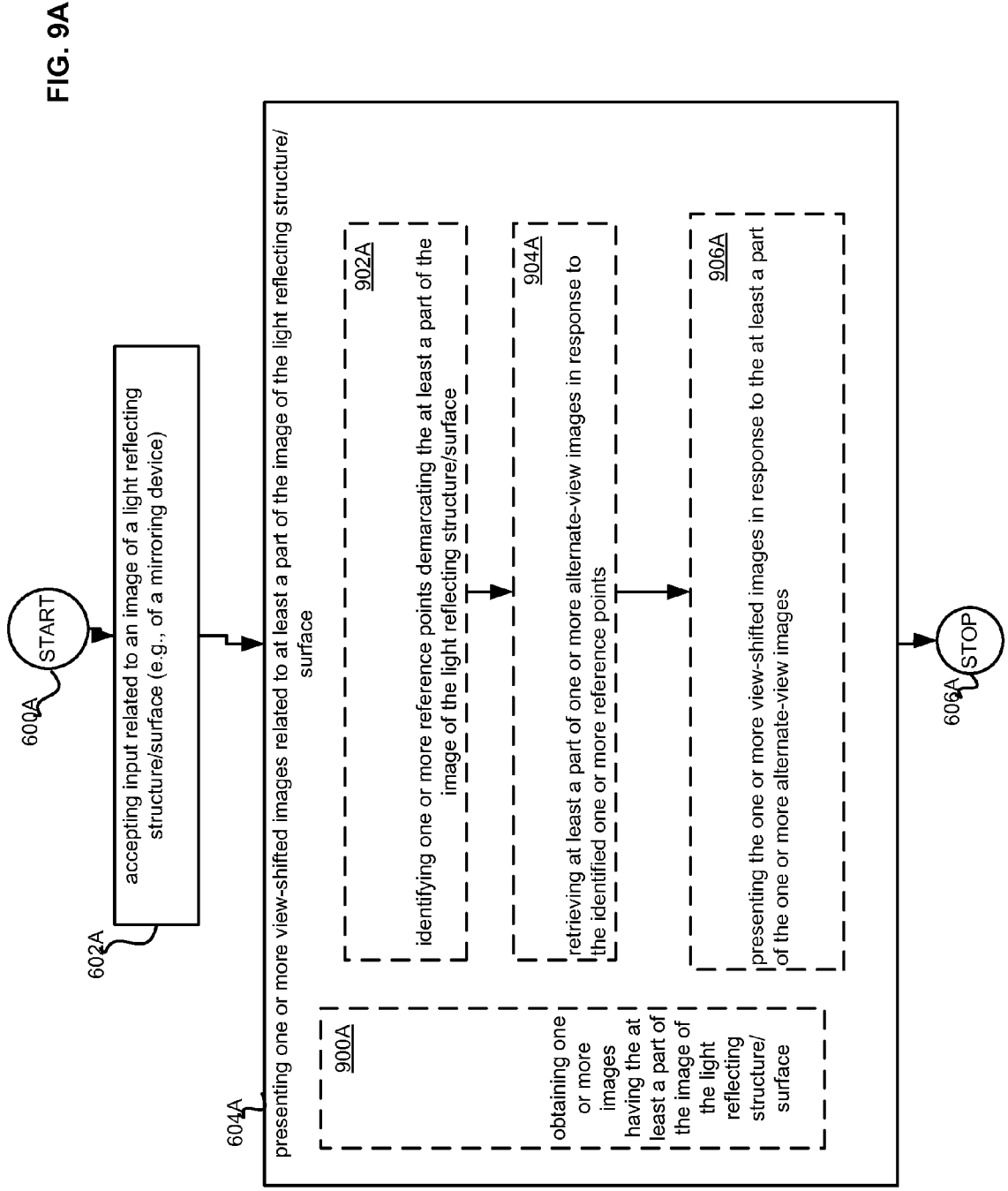
FIG. 9A illustrates a high-level logic flowchart depicting alternate implementations of the high-level logic flowchart of FIG. 6A.

With reference now to FIG. 9A, illustrated is a high-level logic flowchart depicting alternate implementations of the high-level logic flowchart of FIG. 6A. Depicted is that in various alternate implementations, method step 604A includes method step 900A, and/or method steps 902A-906A. Method step 900A shows one alternate implementation of obtaining one or more images having the at least a part of the image of the light reflecting structure/surface. For example, obtaining the one or more images via image recall engine 402A, and/or one or more of image capture storage devices 202A, 204A, 302A, 306A, 310A, 314A, 318A, and/or 322A. Those having skill in the art will recognize that the use of image capture devices in conjunction with image capture storage devices herein is for sake of clarity, and that while in some implementations capture and storage reside in the different devices, in other implementations the capture and storage reside in the same device (e.g., a photo-detector (CCD; CMOS) array itself may constitute both a capture and a (transient) store).

Continuing to refer to FIG. 9A, method steps 902A-906A depict another alternate embodiment. Method step 902A illustrates identifying one or more reference points demarcating the at least a part of the image of the light reflecting structure/surface (e.g., via multi-angle view/registration engine 500A). Method step 904A shows retrieving at least a part of one or more alternate-view images in response to the identified one or more reference points; (904A+text) (e.g., via image recall engine 402A and/or one or more of the image capture storage devices 202A, 204A, 302A, 306A, 310A, 314A, 318A, and/or 322A). Method step 906A depicts presenting the one or more view-shifted images in response to the at least a part of the one or more alternate-view images (e.g., via data presentation device 106A and/or image recall engine 402A and/or multi-angle view/registration engine 500A and/or image sequencing/presentation engine 502A).

Figure 10A:
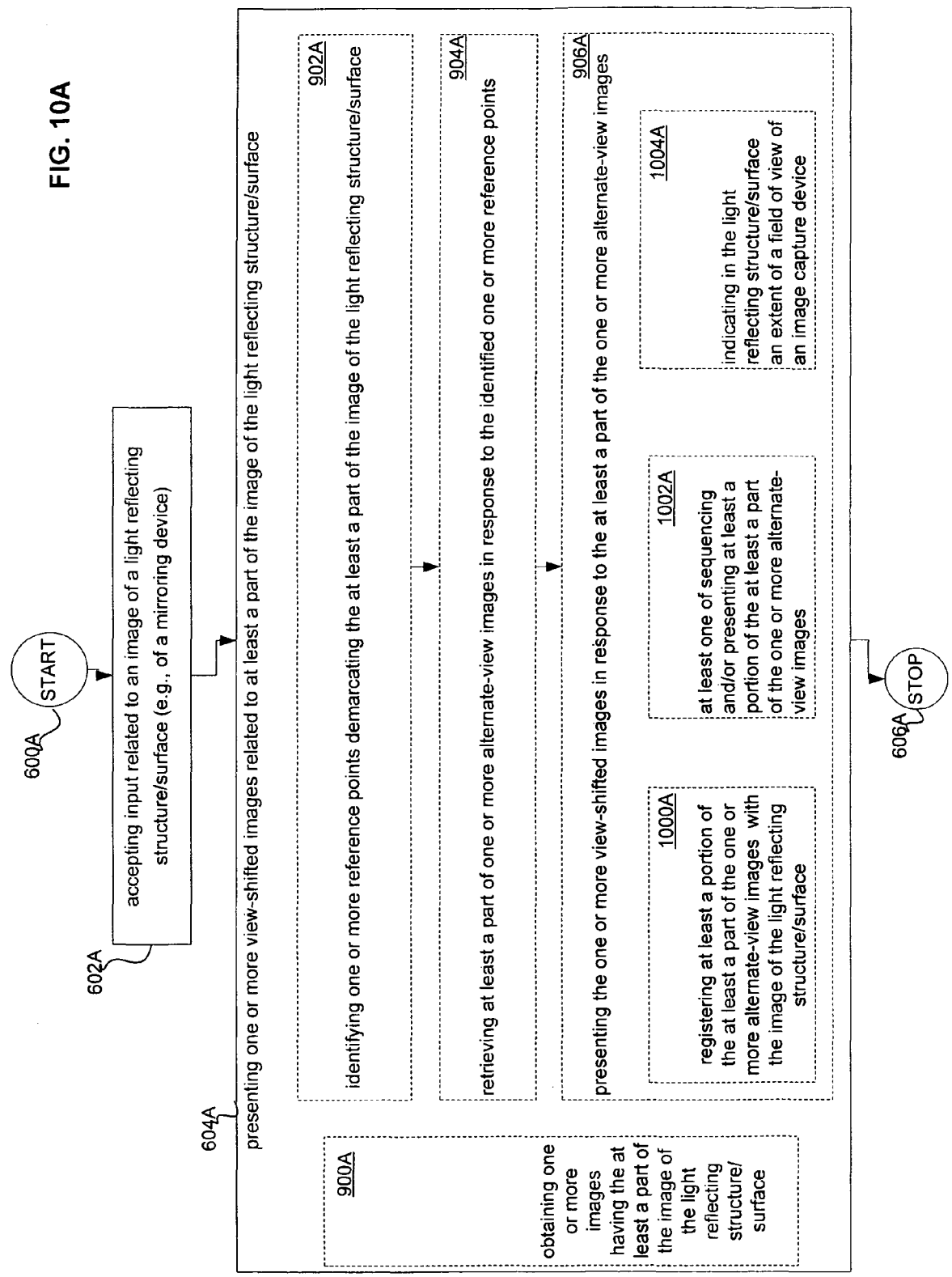
FIG. 10A shows a high-level logic flowchart depicting alternate implementations of the high-level logic flowchart of FIG. 9A.

Referring now to FIG. 10A, shown is a high-level logic flowchart depicting alternate implementations of the high-level logic flowchart of FIG. 9A. Depicted is that in various alternate implementations, method step 906A includes method step 1000A and/or method step 1002A. Method step 1000A illustrates registering at least a portion of the at least a part of the one or more alternate-view images with the image of the light reflecting structure/surface (e.g., via multi-angle view/registration engine 500A performing standard registrations or modified registrations such that the ultimately presented image(s) appear as distortions of mirror views, where such registrations may be accomplished using signal processing techniques to create a "panorama" and/or "fish-eye" and/or "fun-house" view, with distortions). Method step 1002A shows at least one of sequencing or presenting at least a portion of the one or more view-shifted images in response to the at least a part of the one or more alternate-view images (e.g., via image sequencing/presentation engine 502A). In some implementations method step 1002A includes at least one of sequencing at least two view-shifted images captured substantially contemporaneously or sequencing at least two view-shifted images captured at substantially different instances in time. One specific instance of the foregoing includes showing a rotating view of a person in real time and/or showing a rotating view of a person across time to make it look to the viewer as if s/he is on a rotating pedestal. Another specific instance of the foregoing includes slow-rotation through time which is also an example such as where a viewer stands still and watches as s/he spins forward and backward through time. Method step 1004A depicts indicating in the light reflecting structure/surface an extent of a field of view of an image capture device (e.g., an indication representative of a field of view (e.g., relative and/or absolute) associated with the one or more devices used to generate (e.g., reflect and/or capture) the one or more view-shifted-images).

Referring now to FIG. 11A, depicted is a high-level logic flowchart depicting several alternate implementations of the high-level logic flowchart of FIG. 10A. Shown is that in one alternate implementation, method step 904A includes method step 1100A. Method step 1100A shows retrieving from a storage associated with the one or more view-shifted images (e.g., via retrieving from at least one multi-angle view image capture storage device and/or its supporting components). Further shown is that in one alternate embodiment method step 1100A can include method step 1102A which depicts retrieving from a storage associated with at least one alternate view angle of the one or more view-shifted images.

III. Cosmetic Enhancement Mirror

With reference to the figures, and with reference now to FIG. 1B, shown is a partial view of a system that may serve as an illustrative environment of and/or for subject matter technologies. Depicted are light reflecting structure/surface 100B, image capture device 102B, input capture device 104B, and data presentation device 106B. In one exemplary implementation, light reflecting structure/surface 100B can be a plane mirror, a convex mirror, and/or a concave mirror. In another exemplary implementation, light reflecting structure/surface 100B can be a partially silvered mirror. In some exemplary implementations, light reflecting structure/surface 100B can be a physical mirror. In other exemplary implementations, light reflecting structure/surface 100B can be a digital mirror and/or a projection mirror. In yet other implementations, light reflecting structure/surface 100B can be a combination of one or more physical mirrors and/or one or more digital mirrors and/or one or more projection mirrors. In some implementations, data presentation device 106B may present various types of time-lapse information in addition or in the alternative to image information, such as height and/or weight information. In some implementations, presentations of information may be in the form of various modalities including but not limited to graphs, tables, audio (speech, music, sound), text, email (e.g. a weekly digest), et cetera.

Continuing to refer to FIG. 1B, illustrated is data presentation device 106B proximate to light reflecting structure/surface 100B. One exemplary implementation of data presentation device 106B proximate to light reflecting structure/surface 100B includes but is not limited to data presentation device 106B integral with light reflecting structure/surface 100B. Another exemplary implementation of data presentation device 106B proximate to light reflecting structure/surface 100B includes but is not limited to data presentation device 106B operably coupled with light reflecting structure/surface 100B (e.g., as used herein, proximate may mean operationally proximate—able to work and interact together either directly or through intermediate components—as well as and/or in addition to physically proximate and/or mechanically proximate). Yet another exemplary implementation of data presentation device 106B proximate to light reflecting structure/surface 100B includes but is not limited to data presentation device 106B in physical communication with light reflecting structure/surface 100B. One exemplary implementation of data presentation device 106B in physical communication with light reflecting structure/surface 100B includes but is not limited to data presentation device 106B connected with a frame connected with said physical light reflecting structure/surface 100B. In some implementations, data presentation device 106B can be a light generation device (e.g., a plasma display and/or a liquid crystal display), an image presentation device (e.g., a direct projection to the eye retinal display), and/or a laser device (e.g., a laser diode device). Those skilled in the art will appreciate that, as used herein, sorting can include categorization, ordering, and/or other operations such as those described herein.

Figure 2B:
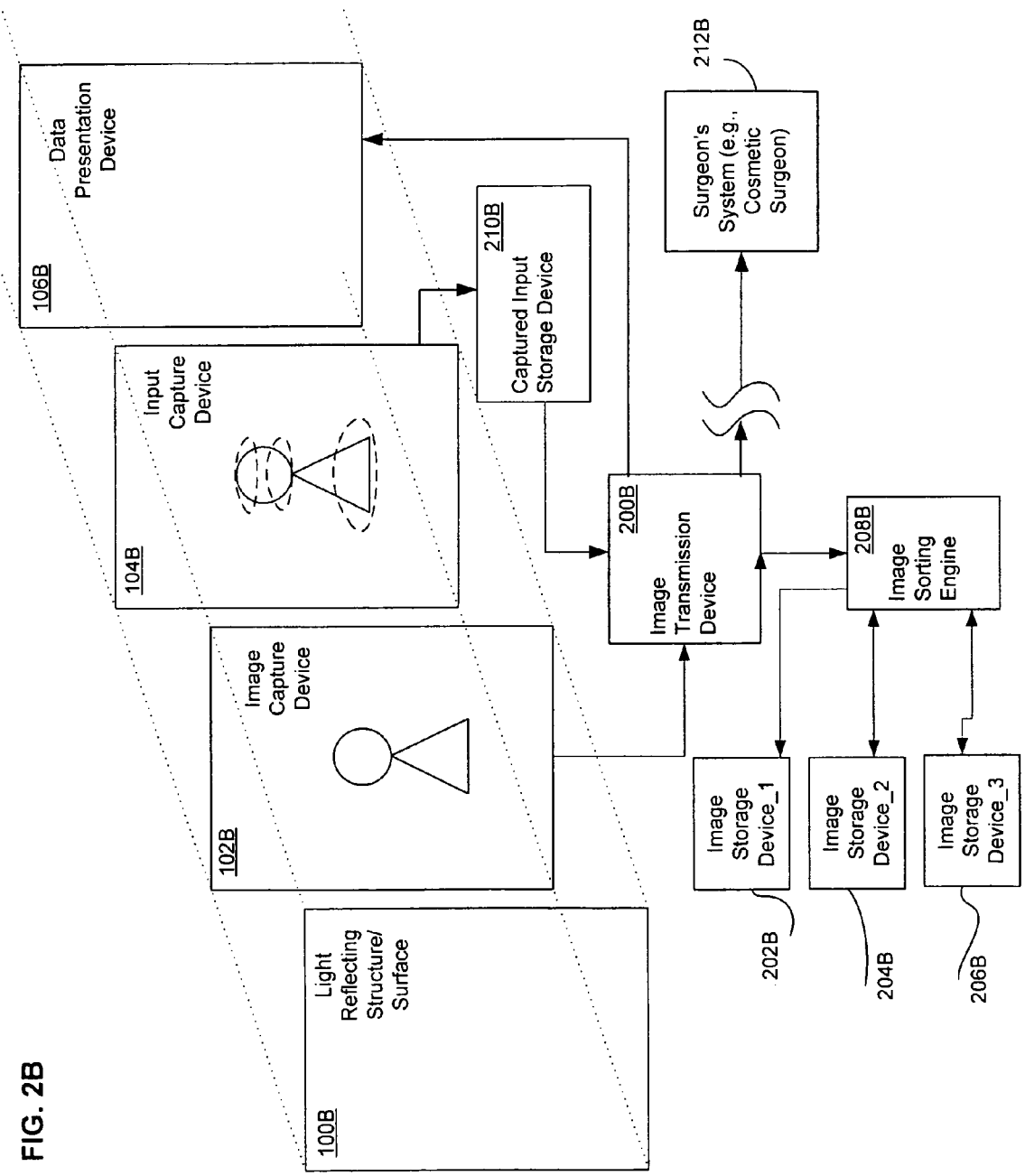
FIG. 2B depicts a partial view of a system that may serve as an illustrative environment of and/or for subject matter technologies.

Referring now to FIG. 2B, depicted is a partial view of a system that may serve as an illustrative environment of and/or for subject matter technologies. Illustrated is that image transmission device 200B interfaces with image capture device 102B. Shown is that image transmission device 200B interfaces with image storage device_1 202B, image storage device_2 204B, image storage device_3 206B, image sorting engine 208B, captured input storage device 210B, and surgeon's system 212B. In one exemplary implementation, image transmission device 200B receives images from image capture device 102B and user input from captured input storage device 210B and/or input capture device 104B. For example, as shown in FIG. 2B, a user might submit to input capture device 104B that he desires to see proposed cosmetic enhancements to his upper body, face, and hairline. Thereafter, in one implementation, image transmission device 200B transmits one or more captured images and the user selected image regions wherein enhancement is desired to surgeon's system 212B.

In another implementation, image transmission device 200B transmits the one or more images and user selected image regions wherein enhancement is desired to image sorting engine 208B. Image sorting engine 208B thereafter sorts the received images into one or more of image storage device_1 202B, image storage device_2 204B, and image storage device_3 206B based on pattern recognition algorithms and stores the images in association with the user input. For example, in an implementation where image capture device 102B is capturing three-dimensional (3-D) images of a human subject, image sorting engine 208B may utilize 3-D image processing routines to sort various recognized captured images into image storage device_1 202B, image storage device_2 204B, and image storage device_3 206B (e.g., where images of a first person are sorted to image storage device_1 202B, images of a second person are sorted to image storage device_2 204B, and images of a third person are sorted to image storage device_3 206B).

In yet another implementation, image transmission device 200B interacts with image sorting engine 208B to recall images from one or more of image storage device_1 202B, image storage device_2 204B, and image storage device_3 206B corresponding to an image in light reflecting structure/surface 100B. Thereafter, image transmission device 200B causes a display of those other retrieved images through data presentation device 106B. Subsequently, a user may select, through the auspices of input capture device 104B, one of those other retrieved images. Thereafter, the user may elect to send the selected images, along with his current image, to surgeon's system 212B. For example, a user could send a younger image of himself, along with his current image, to a cosmetic surgeon in order to get a demonstration from that cosmetic surgeon as to how close that surgeon believes that she can come to reconstructing an appearance consonant with the younger image.

Continuing to refer to FIG. 2B, in one implementation, image capture device 102B can include at least one image representation device located to capture a field of view of light reflecting structure/surface 100B. For example, an active photo-detector array completely and/or partially in identity with a display portion of light reflecting structure/surface 100B or a lensed image capture system oriented such that it could capture all or part of an image reflected from light reflecting structure/surface 100B. In another exemplary implementation, image capture device 102B can include at least two image representation devices located to capture a field of view of light reflecting structure/surface 100B. For example, two or more camera systems positioned to capture stereo imagery such that 3-D imaging techniques may be applied. The image capture devices described herein can be positioned substantially anywhere an image of light reflecting structure/surface 100B can be captured, such as behind light reflecting structure/surface 100B in order to catch transmitted images through a partially silvered mirror, to the sides and/or above and/or below a mirror, and/or positioned and/or oriented to the front of a mirror in order to record images reflected from a mirror.

Figure 3B:
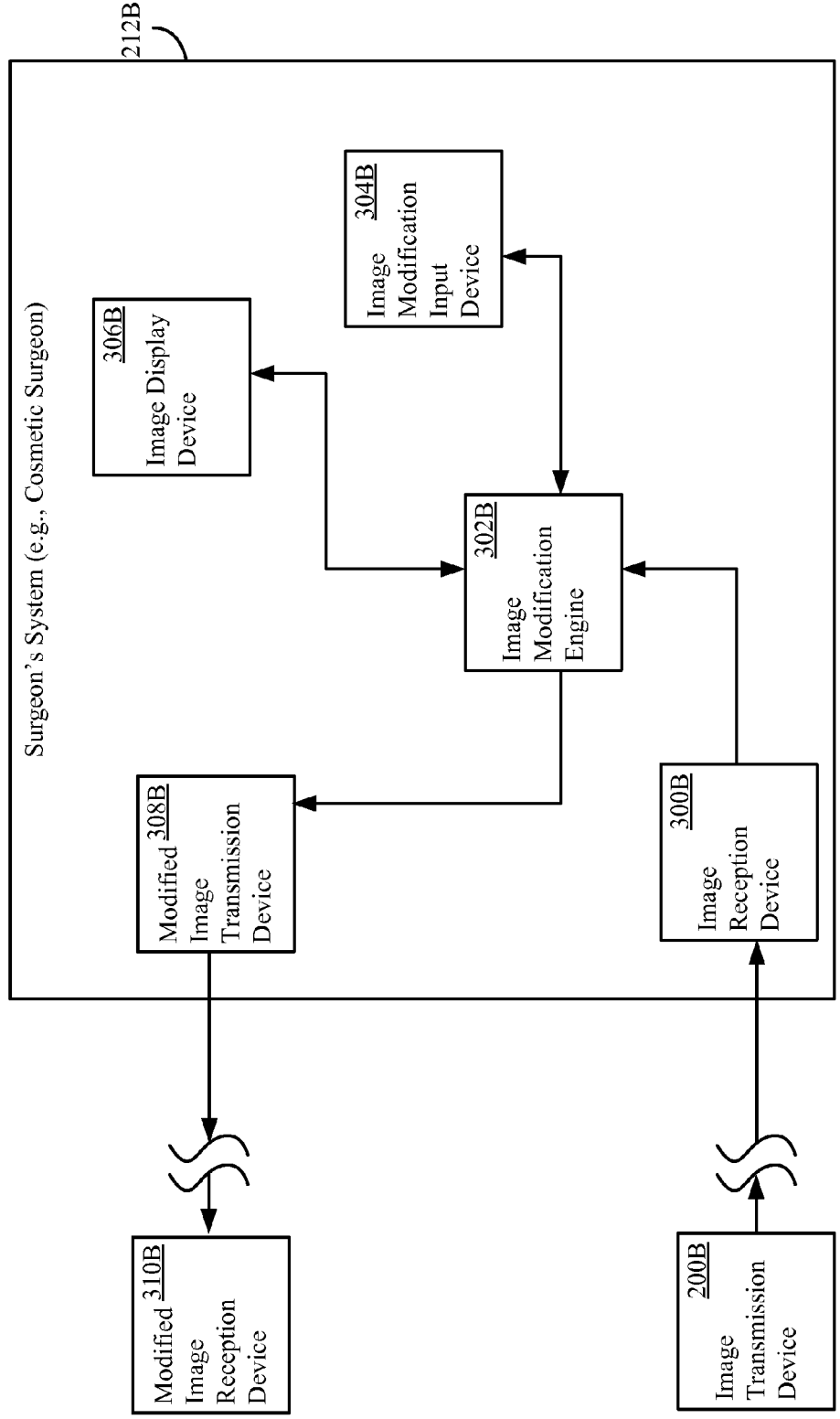
FIG. 3B illustrates a partial view of a system that may serve as an illustrative environment of and/or for subject matter technologies.

With reference now to FIG. 3B, illustrated is a partial view of a system that may serve as an illustrative environment of and/or for subject matter technologies. Shown is image transmission device 200B in communication with image reception device 300B. Depicted is image reception device 300B interfaced with image modification engine 302B. Illustrated is image modification engine 302B interfaced with image modification input device 304B, image display device 306B, and modified image transmission device 308B. Illustrated is modified image transmission device 308B in communication with modified image reception device 310B.

In one exemplary implementation, image reception device 300B receives one or more images along with any associated user input(s) from image transmission device 200B (e.g., images with an indication that the user desires that his body, face, and hairline be enhanced). Thereafter, image reception device 300B transmits the received one or more images and any associated user input indicative of desired modification/enhancement to image modification engine 302B. In one implementation, image modification engine 302B causes a display of the one or more images and user input indicative of desired modification/enhancement on image display device 306B (e.g., a high-quality computer monitor).

Image modification input device 304B accepts input (e.g., from a cosmetic surgeon) to modify the image of image display device 306B. For instance, in one implementation image modification input device 304B provides a graphical user interface and cursor driven input to allow a user (e.g., a cosmetic surgeon) to sculpt the image of image display device 306B in accordance with user input. In response, image modification engine 302B creates a modified version of the displayed image in accord with the input, and displays that modified image back to the surgeon through image display device 306B (often the modified image is displayed in tandem with the unmodified image). Thereafter, the surgeon indicates through image modification input device 304B that the modified image is acceptable, and in response image modification engine 302B causes modified image transmission device 308B to transmit the modified image back to modified image reception device 310B.

Figure 4B:
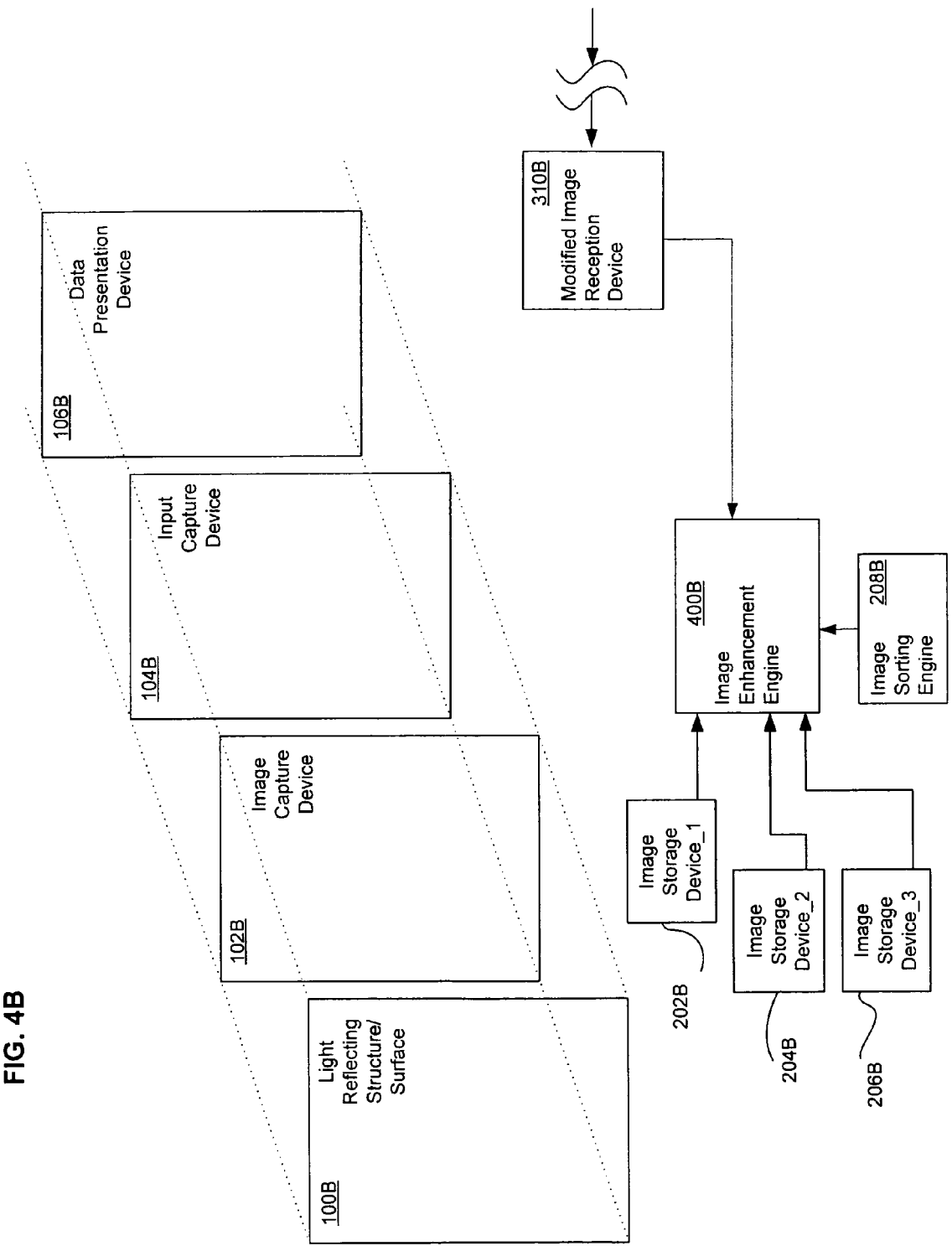
FIG. 4B illustrates a partial view of a system that may serve as an illustrative environment of and/or for subject matter technologies.

Referring now to FIG. 4B, illustrated is a partial view of a system that may serve as an illustrative environment of and/or for subject matter technologies. Shown is modified image reception device 310B receiving signals (e.g., such as those sent by modified image transmission device 308B shown/described in FIG. 3B). Modified image reception device 310B is shown interfaced with image enhancement engine 400B. Image enhancement engine 400B is depicted interfacing with image sorting engine 208B, image storage device_1 202B, image storage device_2 204B, and image storage device_3 206B.

In one implementation, image enhancement engine 400B receives one or more modified images from modified image reception device 310B. In another implementation, in order to save time/bandwidth, image enhancement engine 400B receives instructions as to how to modify the one or more images, and image enhancement engine 400B thereafter interacts with image sorting engine 208B, image storage device_1 202B, image storage device_2 204B, and image storage device_3 206B to actually generate the modified one or more images locally.

Figure 5B:
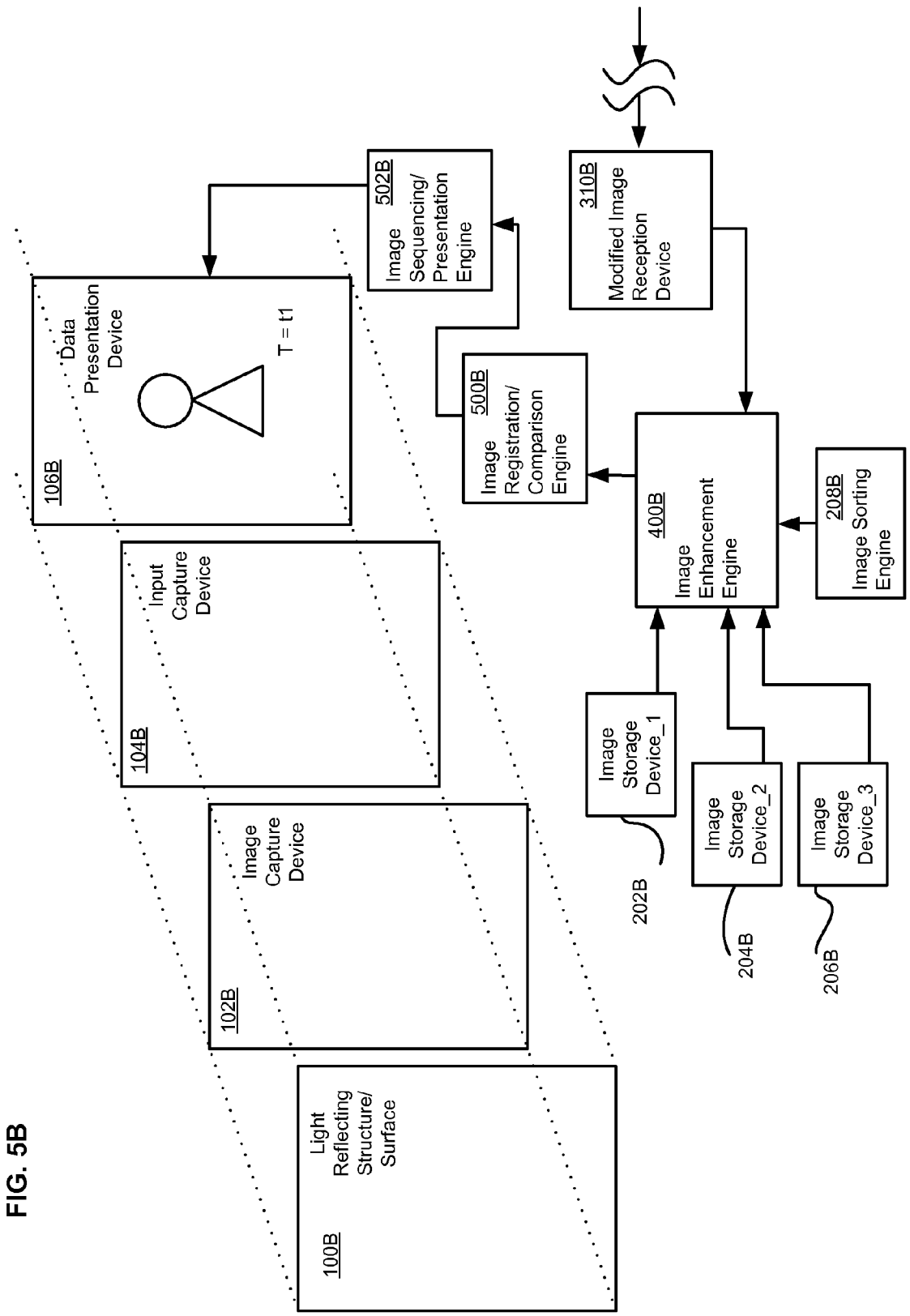
FIG. 5B shows a partial view of a system that may serve as an illustrative environment of and/or for subject matter technologies.

With reference now to FIG. 5B, shown is a partial view of a system that may serve as an illustrative environment of and/or for subject matter technologies. Depicted is image enhancement engine 400B interfaced with image registration/comparison engine 500B. Shown is image registration/comparison engine 500B interfaced with image sequencing/presentation engine 502B. In one exemplary implementation, image enhancement engine 400B—in concert with image sorting engine 208B—retrieves one or more images from one or more of image storage device_1 202B, image storage device_2 204B, and image storage device_3 206B. Subsequently, image enhancement engine 400B enhances/modifies the one or more retrieved images in accord with modification/enhancement instructions (e.g., such as those received from surgeon's system 212B as described herein. Thereafter, image registration/comparison engine 500B uses some relatively stable image feature(s), such as anatomical landmarks (e.g., bony regions or a center part of some defined anatomical feature, to encompass and or localize a region of interest where some feature of interest resides), to provide proper alignment. In another implementation, image enhancement engine 400B receives images that have already been enhanced by image modification engine 302B. Irrespective of whether the enhanced/modified images are generated locally or received in already enhanced/modified form, in one implementation image sequencing/presentation engine 502B then presents the aligned images in a sequenced fashion such that the changes in a region of interest as specified by user input can be viewed. For instance, image sequencing/presentation engine 502B might present a sequenced presentation of various alternate proposed enhancements and/or modifications from the cosmetic surgeon. In another implementation, image sequencing/presentation engine 502B presents a non-sequential menu of options, some which either entail and/or are related to various alternate proposed enhancements and/or modifications from the cosmetic surgeon.

Figure 6B:
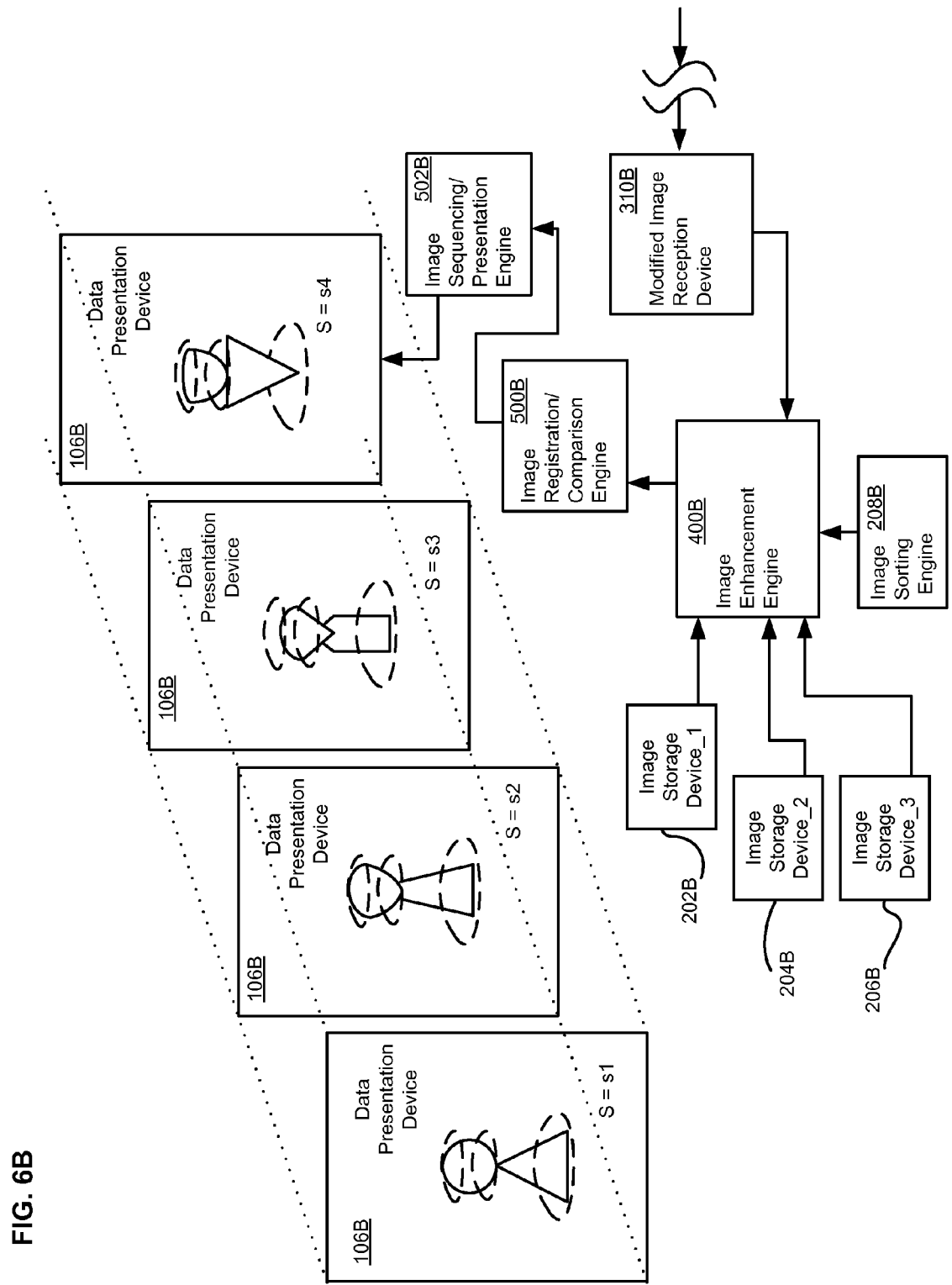
FIG. 6B depicts a partial view of a system that may serve as an illustrative environment of and/or for subject matter technologies

Referring now to FIG. 6B, depicted is a partial view of a system that may serve as an illustrative environment of and/or for subject matter technologies. Illustrated is the system presenting four sequenced images showing various proposed enhancements/modifications to a user's captured image. For instance, depicted at sequence event S=s1 is a presentation of the baseline image entered by the user as well as dashed lines representing user input as to where he desires enhancement. Specifically, shown is that the unenhanced image of the user shows a round face and a triangular shaped body. Proposed suggested enhancements to the user are shown at sequence events S=s2 through S=s4. At sequence events S=s2 through S=s4, shown are various presentations of the user's image enhanced and/or modified, such as in accord with the instructions of a cosmetic surgeon as described elsewhere herein. Depicted in FIG. 6B are exemplary representations of a cosmetic surgeon's enhancement to a user's image, where those enhancements are shown in range of effect starting from the user's unmodified image (e.g., S=s1) and ranging to a projected end condition of a classic V-shaped body and more square jaw line (e.g., S=s4).

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Referring now to FIG. 7B, illustrated is a high-level logic flowchart of a process. Method step 700B shows the start of the process. Method step 702B shows accepting input related to an image of a light reflecting surface (e.g., via input capture device 104B and/or captured input storage device 210B and/or a supporting component(s) accepting input when a user has indicated one or more portions of an image in light reflecting structure/surface 100B). Method step 704B depicts presenting one or more enhanced images related to at least a part of the image of the light reflecting surface (e.g., such as shown/described in relation to FIG. 6B). Method step 706B shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view of a mirror. For example, in a hand-held mirror implementation, a user might zoom in on a region of an image and then ask to see a time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the un-zoomed field of view, in some implementations the use of anchor points will allow coordination between the zoomed and unzoomed views. In addition, the inventors further point out that while examples set forth herein focus on anatomy and/or anatomical change for sake of clarity, the systems described herein can actually track and/or show a time lapse of substantially any object that may be reflected in the mirror.

With reference now to FIG. 8B, shown is a high-level logic flowchart depicting alternate implementations of the high-level logic flowchart of FIG. 7B. Depicted is that in various alternate implementations, method step 702B includes method step 800B and/or method step 802B. Method step 800B shows accepting touch input to a surface proximate to the at least a part of the image of the light reflecting surface (e.g., via input capture device 104B and/or captured input storage device 210B capturing input when a user has indicated one or more portions of an image in light reflecting structure/surface 100B). Method step 802B depicts accepting input of at least one of a user touching herself, a user gesturing, or a user speaking in relation to the at least a part of the image of the light reflecting surface (e.g., via input capture device 104B capturing input when a user's gestures or pointing relative to at least a part of an image in light reflecting structure/surface 100B and/or the user speaking a command in relation to at least a part of an image in light reflecting structure/surface 100B).

Referring now to FIG. 9B, depicted is a high-level logic flowchart depicting alternate implementations of the high-level logic flowchart of FIG. 8B. Depicted is that in one alternate implementation, method step 800B includes method step 900B and/or method step 902B. Method step 900B shows detecting input to a touch sensitive device associated with the light reflecting surface (e.g. via light reflecting structure/surface 100B and/or input capture device 104B and/or captured input storage device 210B and/or one or more of their supporting components). Method step 902B depicts detecting input to a mouse associated with the light reflecting surface (e.g. via light reflecting structure/surface 100B and/or input capture device 104B and/or captured input storage device 210B and/or one or more of their supporting components).

With reference now to FIG. 10B, illustrated is a high-level logic flowchart depicting alternate implementations of the high-level logic flowchart of FIG. 7B. Depicted is that in various alternate implementations, method step 704B includes method step 1000B, and/or method steps 1002B-1006B. Method step 1000B shows one alternate implementation of obtaining one or more images having the at least a part of the image of the light reflecting surface. For example, obtaining the one or more images via image modification engine 302B, image enhancement engine 400B, image sorting engine 208B, and/or one or more of image storage devices 202B-206B.

Continuing to refer to FIG. 10B, method steps 1002B-1006B depict another alternate embodiment. Method step 1002B illustrates identifying one or more anatomical landmarks demarcating the at least a part of the image of the light reflecting surface (e.g., via image sorting engine 208B and/or image registration/comparison engine 500B). Method step 1004B shows enhancing at least a part of the one or more images having the one or more anatomical landmarks (e.g., via image modification engine 302B and/or image enhancement engine 400B). Method step 1006B depicts presenting one or more enhanced versions of the one or more images having the one or more anatomical landmarks (e.g., via data presentation device 106B and/or image enhancement engine 400B).

Figure 11B:
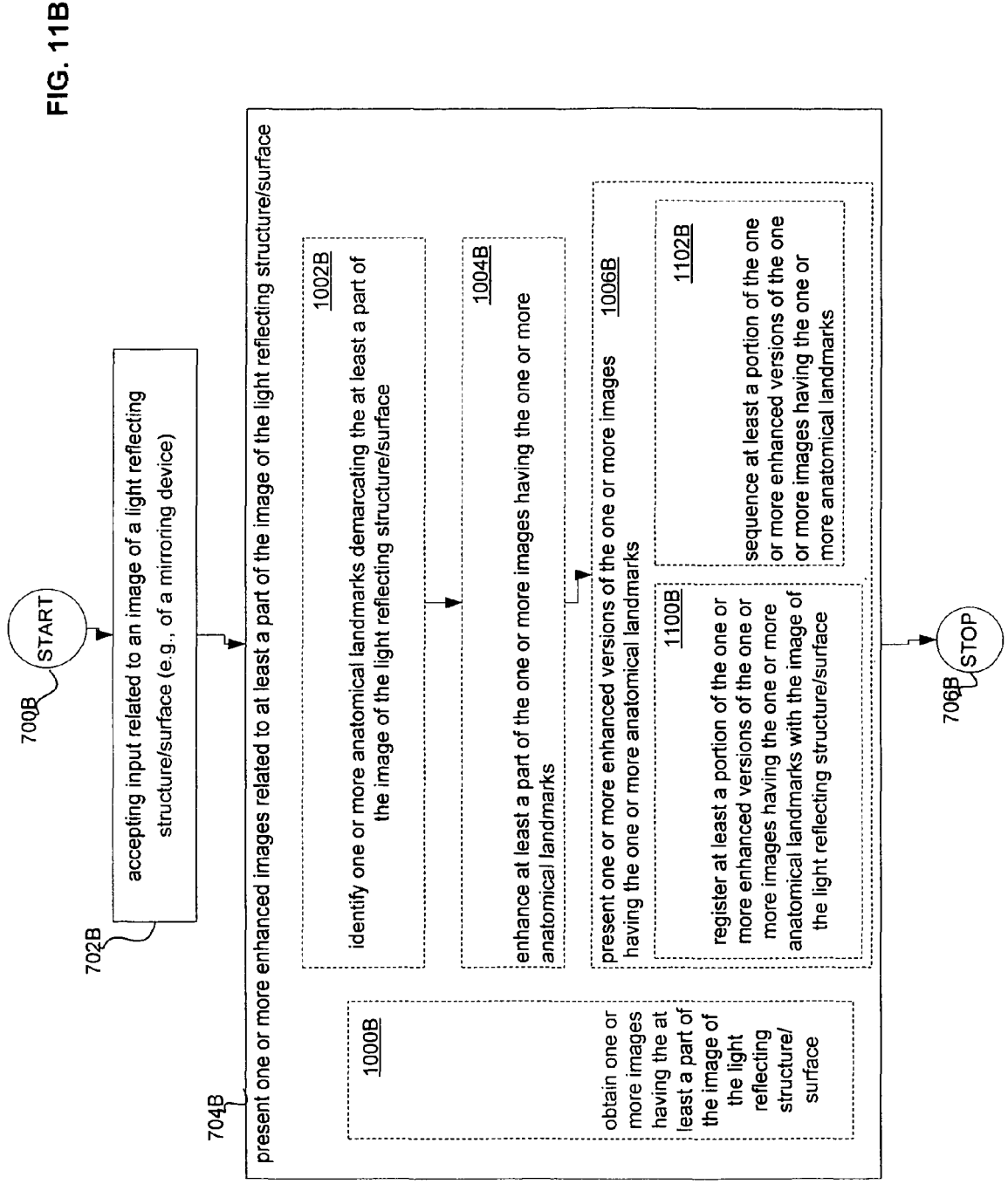
FIG. 11B shows a high-level logic flowchart depicting alternate implementations of the high-level logic flowchart of FIG. 10B.

Referring now to FIG. 11B, shown is a high-level logic flowchart depicting alternate implementations of the high-level logic flowchart of FIG. 10B. Depicted is that in various alternate implementations, method step 1006B includes method step 1100B and/or method step 1102B. Method step 1100B illustrates registering at least a portion of the one or more enhanced versions of the one or more images having the one or more anatomical landmarks with the image of the light reflecting surface (e.g., via image registration/comparison engine 500B). Method step 1102B shows sequencing at least a portion of the one or more enhanced versions of the one or more images having the one or more anatomical landmarks (e.g., via image sequencing/presentation engine 502B).

Referring now to FIG. 12B, illustrated is a high-level logic flowchart depicting several alternate implementations of the high-level logic flowchart of FIG. 10B. Shown is that in one alternate implementation, method step 1004B includes method step 1200B. Method step 1200B shows enhancing a specified feature having a state (e.g., via input capture device 102B and/or image modification engine 302B and/or image enhancement engine 400B and/or their supporting components). Further shown is that in one alternate embodiment method stop 1200B can include method step 1202B which depicts enhancing at least one skin feature (e.g., either smoothing wrinkles on the forehead, should that user have indicated via input that his forehead was a region of interest, or enhancing a person's hair count should that user have indicated via input that his thinning hair was an issue). Further shown is that in yet another alternate embodiment method stop 1200B can include method step 1204B which illustrates enhancing at least one body region (e.g., either making more full or less full a user's jowls, should that user have indicated via input that his jowls were a region of interest, or enhancing a person's upper body should that user have indicated via input that his upper body was a region of interest).

IV. Time-Lapsing Mirror

Figure 1C:
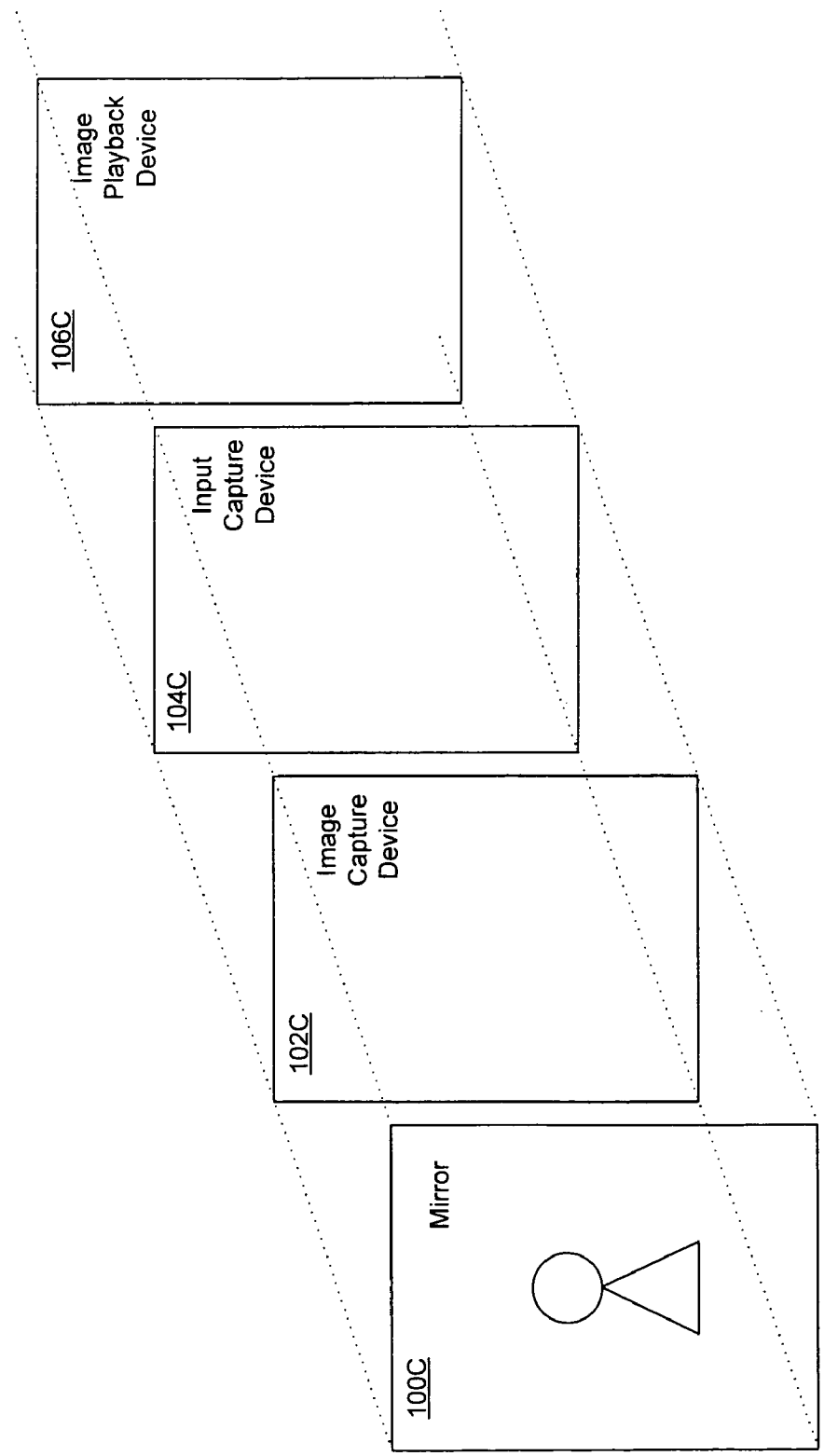
FIG. 1C shows a partial view of a system that may serve as an illustrative environment of and/or for subject matter technologies.

With reference to the figures, and with reference now to FIG. 1C, shown is a partial view of a system that may serve as an illustrative environment of and/or for subject matter technologies. Depicted are mirror 100C, image capture device 102C, input capture device 104C, and image playback device 106C. In one exemplary implementation, mirror 100C can be a plane mirror, a convex mirror, and/or a concave mirror. Examples of such mirrors may include bathroom, hall, and/or handheld mirrors. In another exemplary implementation, mirror 100C can be a partially silvered mirror. In some exemplary implementations, mirror 100C can be a physical mirror. In other exemplary implementations, mirror 100C can be a digital mirror and/or a projection mirror. In yet other implementations, mirror 100C can be a combination of one or more physical mirrors and/or one or more digital mirrors and/or one or more projection mirrors. In some implementations, image playback device 106C may present various types of time-lapse information in addition or in the alternative to image information, such as height and/or weight information. In some implementations, presentations of information may be in the form of various modalities including but not limited to graphs, tables, audio (speech, music, sound), text, email (e.g. a weekly digest), et cetera.

Continuing to refer to FIG. 1C, illustrated is image playback device 106C proximate to mirror 100C. One exemplary implementation of image playback device 106C proximate to mirror 100C includes but is not limited to image playback device 106C integral with physical mirror 100C. Another exemplary implementation of image playback device 106C proximate to mirror 100C includes but is not limited to image playback device (106C) operably coupled with physical mirror 100C (e.g., as used herein, proximate may mean operationally proximate—able to work and interact together either directly or through intermediate components—as well as and/or in addition to physically proximate and/or mechanically proximate). Yet another exemplary implementation of image playback device 106C proximate to mirror 100C includes but is not limited to image playback device 106C in physical communication with physical mirror 100C. One exemplary implementation of image playback device 106C in physical communication with physical mirror 100C includes but is not limited to image playback device 106C connected with a frame connected with said physical mirror 100C. In some implementations, image playback device 106C can be a light generation device (e.g., a plasma display and/or a liquid crystal display), an image presentation device (e.g., a direct projection to the eye retinal display), and/or a laser device (e.g., a laser diode device).

Referring now to FIG. 2C, depicted is a partial view of a system that may serve as an illustrative environment of and/or for subject matter technologies. Illustrated is that image sorting engine 200C interfaces with image capture device 102C. Shown is that image sorting engine 200C interfaces with image storage device_1 202C, image storage device_2 204C, and image storage device_3 206C. In one exemplary implementation, image sorting engine 200C receives images from image capture device 102C and sorts the received images into one or more of image storage device_1 202C, image storage device_2 204C, and image storage device_3 206C based on pattern recognition algorithms. For example, in an implementation where image capture device 102C is capturing three-dimensional (3-D) images of a human subject, image sorting engine 200C may utilize 3-D image processing routines to sort various recognized captured images into image storage device_1 202C, image storage device_2 204C, and image storage device_3 206C (e.g., where images of a first person are sorted to image storage device_1 202C, images of a second person are sorted to image storage device_2 204C, and images of a third person are sorted to image storage device_3 206C). Those skilled in the art will appreciate that, as used herein, sorting can include categorization, ordering, and/or other operations such as those described herein.

Continuing to refer to FIG. 2C, in one implementation, image capture device 102C can include at least one image representation device located to capture a field of view of mirror 100C. For example, an active photo-detector array completely and/or partially in identity with a display portion of mirror 100C or a lensed image capture system oriented such that it could capture all or part of an image reflected from mirror 100C. In another exemplary implementation, image capture device 102C can include at least two image representation devices located to capture a field of view of mirror 100C. For example, two or more camera systems positioned to capture stereo imagery such that 3-D imaging techniques may be applied. The image capture devices described herein can be positioned substantially anywhere an image of mirror 100C can be captured, such as behind mirror 100C in order to catch transmitted images through a partially silvered mirror, to the sides and/or above and/or below a mirror, and/or positioned and/or oriented to the front of a mirror in order to record images reflected from a mirror. In some implementations, the image capture devices may also be positioned such that they reside behind where a user would be expected to stand when viewing mirror 100C.

With reference now to FIG. 3C, illustrated is a partial view of a system that may serve as an illustrative environment of and/or for subject matter technologies. Shown is captured input storage device 300C exchanging signals with input capture device 104C. Depicted is image recognition engine 302C exchanging signals with captured input storage device 300C, image sorting engine 200C, image storage device_1 202C, image storage device_2 204C, and image storage device_3 206C. In one exemplary implementation, a user (e.g., a human user) touches and/or circles a region of an image in mirror 100C and asks that the system show a time-lapse presentation of the region over some interval of time. For example, a human user touching a skin lesion on his/her image and asking that the system show the mole over the last three months. In response, in one implementation captured input storage device 300C captures both the region of the image touched as well as the request for the time-lapse presentation of the mole (in some implementations, the request is typed such as via touch screen entry to a menu driven system, while in other implementations, the request is spoken such as via voice recognition input driven system). Thereafter, in one implementation, image recognition engine 302C interacts with image sorting engine 200C to determine where images associated with the person whose input has been captured are stored. For example, if the person in the mirror's previously captured images had been stored in image storage device_3 206C, then image sorting engine 200C would inform image recognition engine 302C of that fact. Thereafter, image recognition engine 302C would know the storage location of that person's image.

Figure 4C:
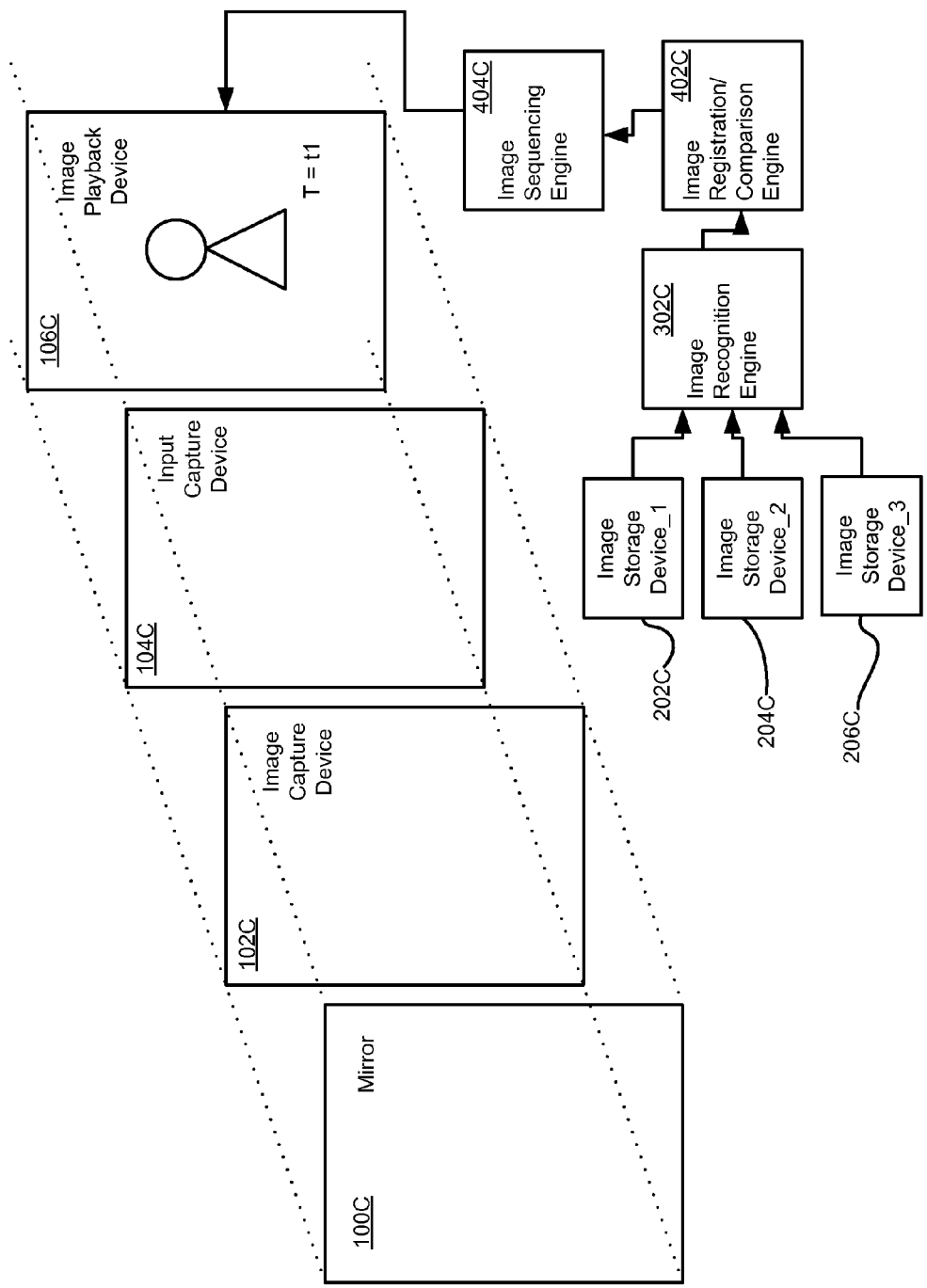
FIG. 4C shows a partial view of a system that may serve as an illustrative environment of and/or for subject matter technologies.

Referring now to FIG. 4C, shown is a partial view of a system that may serve as an illustrative environment of and/or for subject matter technologies. Depicted is image recognition engine 302C interfaced with image sorting engine 200C, image storage device_1 202C, image storage device_2 204C, and image storage device_3 206C. Illustrated is image recognition engine 302C interfaced with image registration/comparison engine 402C. Shown is image registration/comparison engine 402C interfaced with image sequencing engine 404C. In one exemplary implementation, image recognition engine 302C retrieves time-sequenced images from one or more of image storage device_1 202C, image storage device_2 204C, and image storage device_3 206C. Thereafter, image registration/comparison engine 402C uses some relatively stable image feature(s), such as anatomical landmarks (e.g., bony regions or a center part of some defined anatomical feature), to encompass and or localize a region of interest where some feature of interest resides, to provide proper alignment. Image sequencing engine 404 then presents the aligned images in a time sequenced fashion such that the changes in the region of interest can be viewed over time. For instance, a time-lapse presentation of how a mole has grown over the last few months.

In some implementations, instead of or as an addition to the foregoing, image registration/comparison engine 402C compares a specified feature (e.g., hair length or jowl size) against a reference value and presents information (e.g., an alert) when the specified feature exceeds the reference value by some defined amount. As a specific example, a user might instruct the system to alert her if her hair has grown more than 8 millimeters beyond some reference length. If her hair did exceed the threshold beyond the reference length, the system would present a display indicating that event, and perhaps suggesting that a haircut was needed.

Figure 5C:
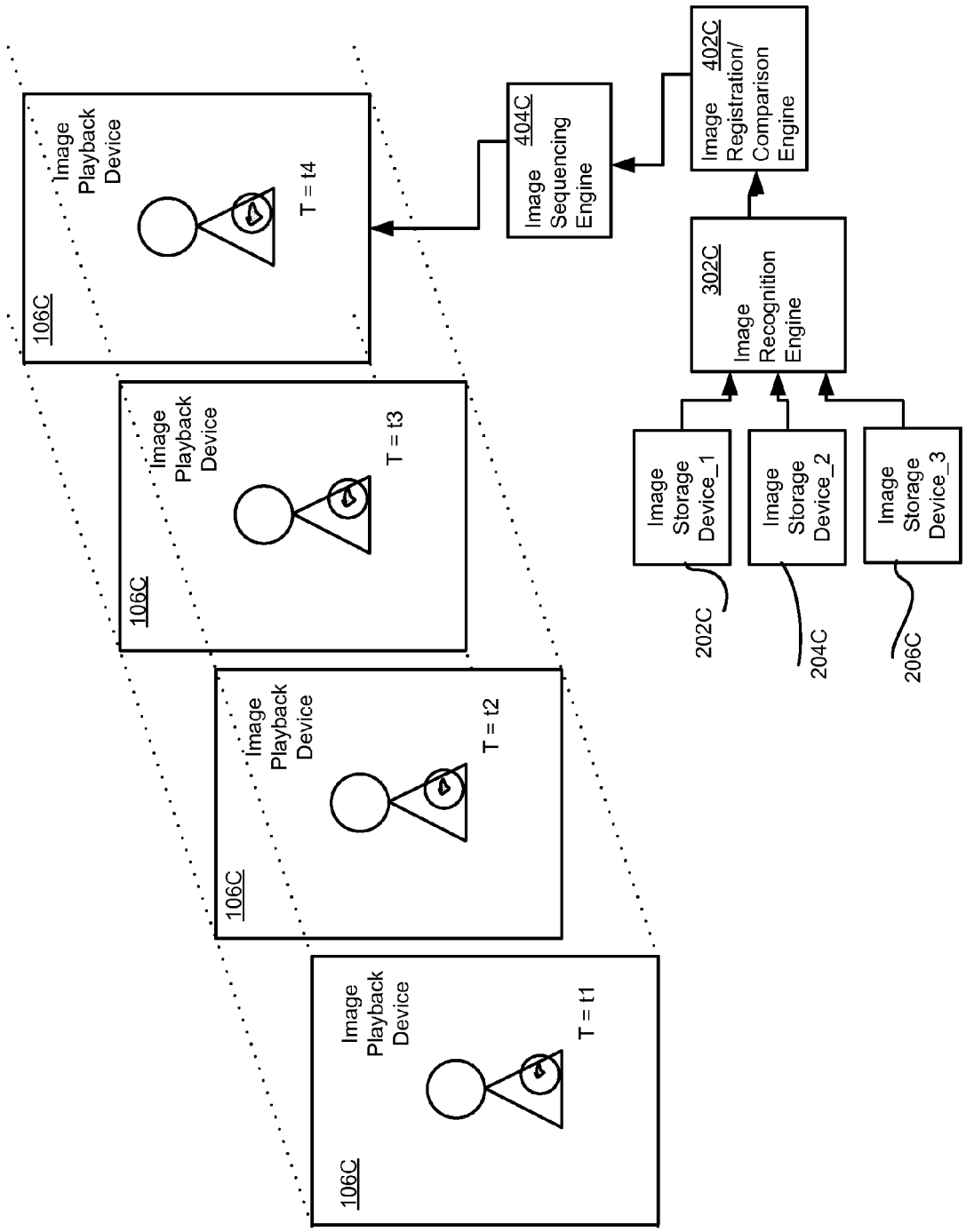
FIG. 5C depicts a partial view of a system that may serve as an illustrative environment of and/or for subject matter technologies.

With reference now to FIG. 5C, depicted is a partial view of a system that may serve as an illustrative environment of and/or for subject matter technologies. Illustrated is the system presenting four (4) time sequenced views showing the growth of lesion within a skin region over time. Depicted is that the lesion is dark with an irregular border and growing, such as, for example, a melanoma region. Other things could be like depicted, like hair length, jowl size, etc.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 6C:
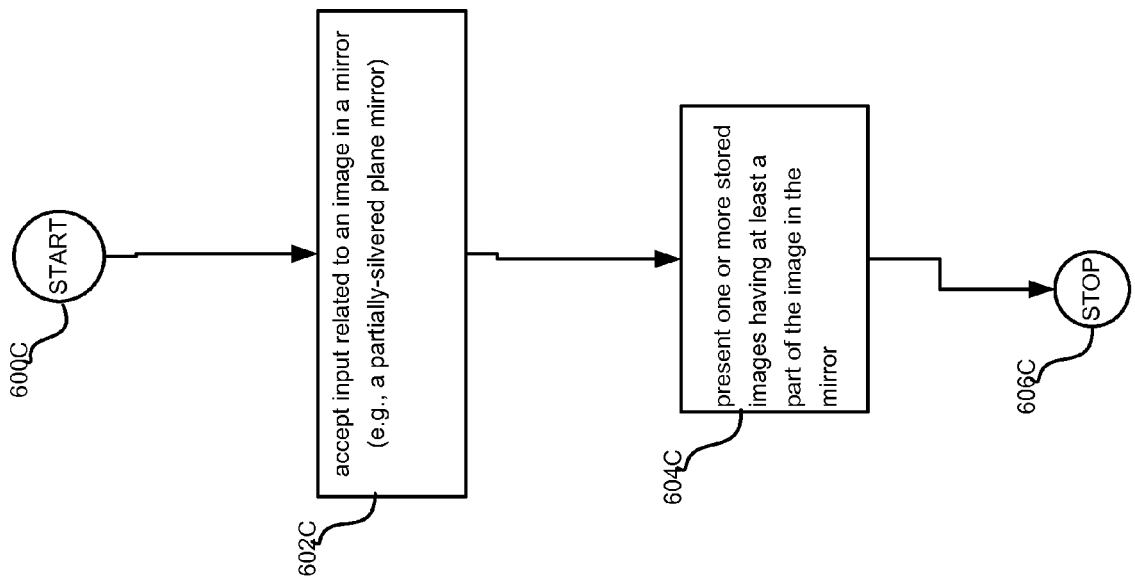
FIG. 6C illustrates a high-level logic flowchart of a process.

Referring now to FIG. 6C, illustrated is a high-level logic flowchart of a process. Method step 600C shows the start of the process. Method step 602C shows accepting input related to an image in a mirror (e.g., via captured input storage device 300C and/or its supporting components). Method step 604C depicts presenting one or more stored images having at least a part of the image in the mirror (e.g., such as shown/described in relation to FIG. 5C). Method step 606C shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view of a mirror. For example, in a hand-held mirror implementation, a user might zoom in on a region of an image and then ask to see a time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the un-zoomed field of view, in some implementations the use of anchor points will allow coordination between the zoomed and unzoomed views. In addition, the inventors further point out that while examples set forth herein focus on anatomy and/or anatomical change for sake of clarity, the systems described herein can actually track and/or show a time lapse of substantially any object that may be reflected in the mirror.

With reference now to FIG. 7C, shown is a high-level logic flowchart depicting alternate implementations of the high-level logic flowchart of FIG. 6C. Depicted is that in various alternate implementations, method step 602C includes method step 700C and/or method step 702C. Method step 700C shows accepting touch input to a mirror surface proximate to the at least a part of the image in the mirror (e.g., via input capture device 104C capturing input when a user's finger is proximate to an image in mirror 100C) Method step 702C depicts accepting input of at least one of a user touching herself, a user gesturing, or a user speaking in relation to the at least a part of the image in the mirror (e.g., via input capture device 104C capturing input when a user's gestures or pointing relative to at least a part of an image in mirror 100C and/or the user speaking a command in relation to at least a part of an image in mirror 100C).

Referring now to FIG. 8C, depicted is a high-level logic flowchart depicting alternate implementations of the high-level logic flowchart of FIG. 7C. Depicted is that in one alternate implementation, method step 700C includes method step 800C and/or method step 802C. Method step 800C shows detecting input to a touch screen device associated with the mirror (e.g. via mirror 100C and/or input capture device 104C and/or one or more of their supporting components). Method step 802C depicts detecting input to a cursor device associated with the mirror (e.g. via mirror 100C and/or input capture device 104C and/or one or more of their supporting components).

With reference now to FIG. 9C, illustrated is a high-level logic flowchart depicting alternate implementations of the high-level logic flowchart of FIG. 6C. Depicted is that in various alternate implementations, method step 604C includes method step 900C, and/or method steps 902C-906C, and/or method steps 912C-914C. Method step 900C shows one alternate implementation of locating one or more images having the at least a part of the image in the mirror. For example, locating the one or more images via image sorting engine 200C, captured input storage device 300C, image recognition engine 302C, and/or one or more of image storage devices 202C-206C.

Continuing to refer to FIG. 9C, method steps 902C-906C depict another alternate embodiment. Method step 902C illustrates identifying one or more anatomical landmarks demarcating the at least a part of the image in the mirror (e.g., via image sorting engine 200C and/or image recognition engine 302C). Method step 904C shows obtaining one or more images having the one or more anatomical landmarks (e.g., via image recognition engine 302C and/or image registration/comparison engine 402C). Method step 906C depicts presenting the one or more images having the one or more anatomical landmarks (e.g., via image playback device 106C and/or image sequencing engine 404C).

Continuing to refer to FIG. 9C, method steps 912C-914C illustrate yet another alternate embodiment. Method step 912C shows tracking a specified feature having a state (e.g., via image registration/comparison engine 402C and/or its supporting components). Method step 914C depicts presenting the one or more stored images when a change in the state exceeds a selected tolerance value (e.g., via image registration/comparison engine 402C and/or image sequencing engine 404C and/or their supporting components).

Referring now to FIG. 10C, shown is a high-level logic flowchart depicting alternate implementations of the high-level logic flowchart of FIG. 9C. Depicted is that in various alternate implementations, method step 906C includes method step 1000C and/or method step 1002C. Method step 1000C illustrates registering at least a portion of the one or more images having the one or more anatomical landmarks with the image in the mirror (e.g., via image registration/comparison engine 402C). Method step 1002C shows sequencing at least a portion of the one or more images having the one or more anatomical landmarks (e.g., via image sequencing engine 404C).

Figure 11C:
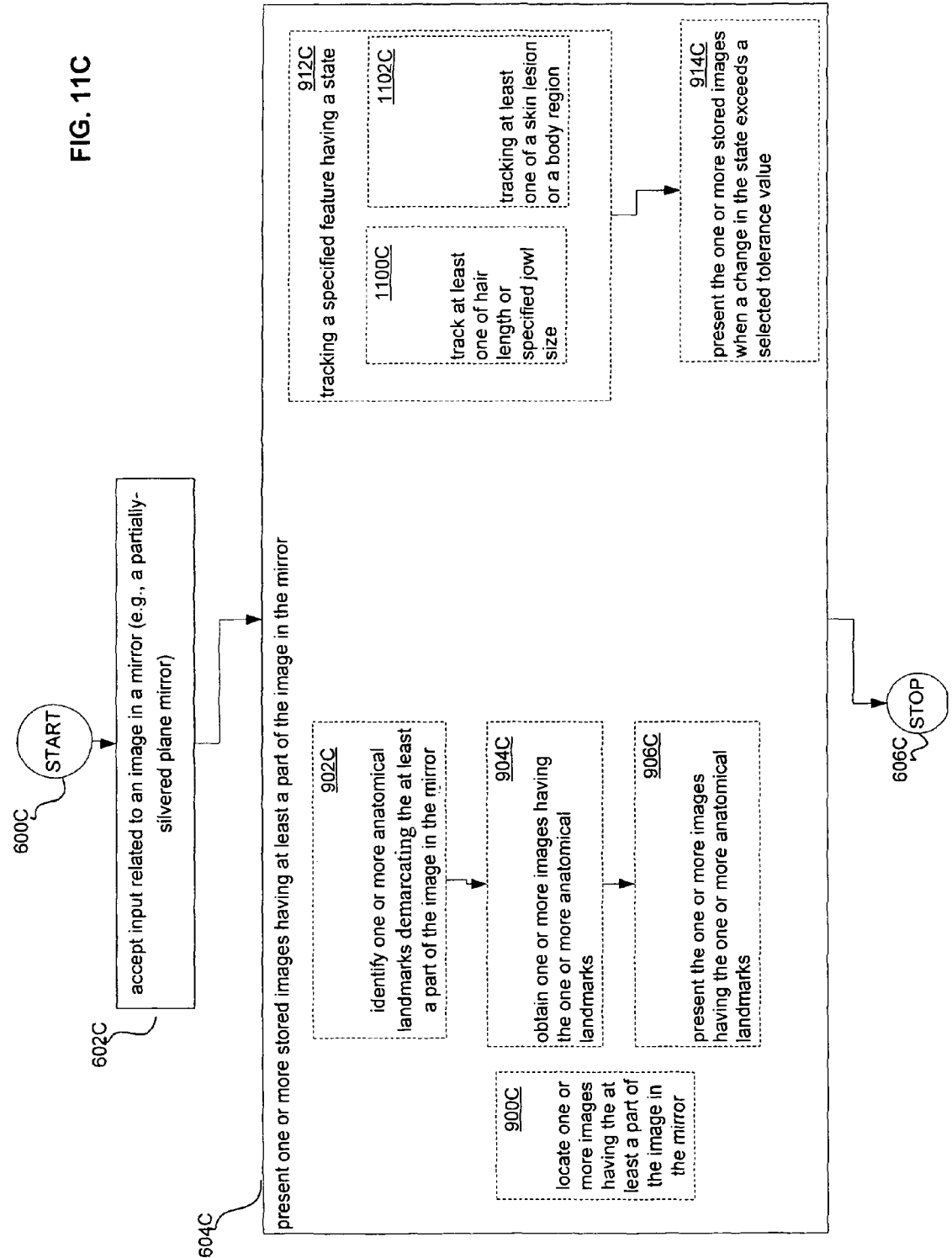
FIG. 11C depicts a high-level logic flowchart depicting alternate implementations of the high-level logic flowchart of FIG. 9C.

With reference now to FIG. 11C, depicted is a high-level logic flowchart depicting alternate implementations of the high-level logic flowchart of FIG. 9C. Illustrated is that in various alternate implementations, method step 912C includes method step 1100C and/or method step 1102C. Method step 1100C illustrates tracking at least one of hair length or jowl size (e.g., via image registration/comparison engine 402C and/or its supporting components). Method step 1102C shows tracking at least one of a skin lesion or a body region (e.g., via image recognition engine 302C and/or image registration/comparison engine 402C and/or their supporting components), which the inventors point out is helpful in a handheld mirror implementation.

Referring now to FIG. 12C, illustrated is a high-level logic flowchart depicting an alternate implementation of the high-level logic flowchart of FIG. 9C. Shown is that in one alternate implementation, method step 914C includes method step 1200C. Method step 1200C shows presenting an image having the state in conjunction with an image whose state exceeds the selected tolerance value (e.g., via image recognition engine 302C and/or image registration/comparison engine 402C and/or image sequencing engine 404C and/or their supporting components).

The invention claimed is:

1. A system comprising:
an image reception device configured to receive one or more surgically-related enhancement requests related to an image, wherein the one or more surgically-related enhancement requests related to the image are associated with a patient-owned and/or patient-controlled apparatus that includes:
a light reflecting structure;
a data presentation device proximate to said light reflecting structure;
an image enhancement engine operably couplable to said data presentation device;
and
at least one image capture device operably couplable with said image enhancement engine, wherein said at least one image capture device includes:
at least one image representation capture device sufficient to be located to capture a field of view of said light reflecting structure; and
said at least one image representation capture device alignable relative to a field of view of said light reflecting structure;
an image modification engine operably coupled with said image reception device configured to receive the one or more surgically-related enhancement requests related to the image; and
an image modification input device configured to receive one or more surgically-related modification inputs associated with the image, said image modification input device operably couplable with said image modification engine.

2. The system of claim 1, wherein said light reflecting structure further comprises:
at least one of a plane mirror, a convex mirror, or a concave mirror.

3. The system of claim 1, wherein said light reflecting structure further comprises:
a partially silvered mirror.

4. The system of claim 1, wherein said data presentation device proximate to said light reflecting structure further comprises:
said data presentation device integral with said light reflecting structure.

5. The system of claim 1, wherein said data presentation device proximate to said light reflecting structure further comprises:
said data presentation device operably coupled with said light reflecting structure.

6. The system of claim 1, wherein said data presentation device proximate to said light reflecting structure further comprises:
said data presentation device in physical communication with said light reflecting structure.

7. The system of claim 6, wherein said data presentation device in physical communication with said light reflecting structure further comprises:
said data presentation device connected with a housing connected with said light reflecting structure.

8. The system of claim 1, further comprising:
at least one image storage device operably couplable with said data presentation device.

9. The system of claim 1, further comprising:
at least one image transmission device operably couplable with an input capture device.

10. The system of claim 1, wherein said at least one image representation capture device sufficient to be located to capture a field of view of said light reflecting structure further comprises:
at least one image representation capture device located to capture a field of view of said light reflecting structure and/or at least one image representation capture device having instructions as to how to place the image representation capture device to capture a field of view of said light reflecting structure.

11. The system of claim 1, wherein said at least one image representation capture device alignable relative to a field of view of said light reflecting structure further comprises:
at least two image representation capture devices alignable relative to a field of view of said light reflecting structure.

12. The system of claim 1, further comprising:
at least one input capture device operably couplable with said data presentation device.

13. The system of claim 1, further comprising:
at least one image registration engine operably couplable with said data presentation device.

14. The system of claim 1, wherein said at least one image representation capture device alignable relative to a field of view of said light reflecting structure further comprises:
said at least one image representation capture device aligned relative to a field of view of said light reflecting structure.

15. A system comprising:
circuitry for receiving one or more surgically-related enhancement requests related to an image, wherein the one or more surgically-related enhancement requests related to the image are associated with a patient-owned or patient-controlled apparatus that includes:
a light reflecting structure;
a data presentation device proximate to said light reflecting structure;
an image enhancement engine operably couplable to said data presentation device; and
at least one image capture device operably couplable with said image enhancement engine, wherein said at least one image capture device includes:
at least one image representation capture device sufficient to be located to capture a field of view of said light reflecting structure; and
said at least one image representation capture device alignable relative to a field of view of said light reflecting structure; and
circuitry for modifying the image responsive to one or more surgically-related modification inputs associated with the image.

16. The system of claim 15, wherein said circuitry for modifying the image in response to one or more surgically-related modification inputs associated with the image comprises:
 circuitry for presenting a representation of the one or more surgically-related enhancement requests related to the image; and
 circuitry for accepting the one or more surgically-related modification inputs associated with the image.

17. The system of claim 15, further comprising:
 circuitry for transmitting one or more modification/enhancement instructions associated with a surgeon and/or one or more modified/enhanced images associated with a surgeon to the patient-owned or patient-controlled apparatus responsive to said circuitry for modifying the image responsive to the one or more surgically-related modification inputs associated with the image.

18. The system of claim 15, wherein the patient-owned or patient-controlled apparatus further comprises:
 circuitry for accepting input related to an image of a light reflecting surface; and
 circuitry for presenting one or more enhanced images related to at least a part of the image of the light reflecting surface.

19. The system of claim 18, wherein said circuitry for accepting input related to an image of a light reflecting surface further comprises:
 circuitry for accepting touch input to a surface proximate to the at least a part of the image of the light reflecting surface.

20. The system of claim 19, wherein said circuitry for accepting touch input to a surface proximate to the at least a part of the image of the light reflecting surface further comprises:
 circuitry for detecting input to a touch sensitive device associated with the light reflecting surface.

21. The system of claim 18, wherein said circuitry for accepting input related to an image of a light reflecting surface further comprises:
 circuitry for accepting input of at least one of a user touching herself, a user gesturing, or a user speaking in relation to the at least a part of the image of the light reflecting surface.

22. The system of claim 18, wherein said circuitry for presenting one or more enhanced images related to at least a part of the image of the light reflecting surface further comprises:
 circuitry for obtaining one or more images having the at least a part of the image of the light reflecting surface.

23. The system of claim 18, wherein said circuitry for presenting one or more enhanced images related to at least a part of the image of the light reflecting surface further comprises:
 circuitry for identifying one or more anatomical landmarks demarcating the at least a part of the image of the light reflecting surface;
 circuitry for enhancing at least a part of one or more images having the one or more anatomical landmarks; and
 circuitry for presenting one or more enhanced versions of the one or more images having the one or more anatomical landmarks.

24. The system of claim 23, wherein said circuitry for presenting one or more enhanced versions of the one or more images having the one or more anatomical landmarks further comprises:
 circuitry for registering at least a portion of the one or more enhanced versions of the one or more images having the one or more anatomical landmarks with the image of the light reflecting surface.

25. The system of claim 23, wherein said circuitry for presenting one or more enhanced versions of the one or more images having the one or more anatomical landmarks further comprises:
 circuitry for at least one of sequencing or presenting at least a portion of the one or more enhanced versions of the one or more images having the one or more anatomical landmarks.

26. The system of claim 23, wherein said circuitry for enhancing at least a part of the one or more images having the one or more anatomical landmarks further comprises:
 circuitry for enhancing a specified feature having a state.

27. The system of claim 26, wherein said circuitry for enhancing a specified feature having a state further comprises:
 circuitry for enhancing at least one skin feature.

28. The system of claim 26, wherein said circuitry for enhancing a specified feature having a state further comprises:
 circuitry for enhancing at least one body region.

29. The system of claim 15, wherein said at least one image representation capture device alignable relative to a field of view of said light reflecting structure further comprises:
 said at least one image representation capture device aligned relative to a field of view of said light reflecting structure.

* * * * *

UNITED STATES PATENT AND TRADEMARK OFFICE
CERTIFICATE OF CORRECTION

PATENT NO. : 7,952,537 B2
APPLICATION NO. : 12/660030
DATED : May 31, 2011
INVENTOR(S) : Allen et al.

It is certified that error appears in the above-identified patent and that said Letters Patent is hereby corrected as shown below:

On the Title Page

Item (60) at Column 2, approximately Lines 13-14, "No. 12/286,457, filed Sep. 30, 2008" should read --No. 12/286,547, filed Sep. 29, 2008--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*